(12) United States Patent
Wagner et al.

(10) Patent No.: US 10,779,922 B2
(45) Date of Patent: Sep. 22, 2020

(54) PAUSE VALVE AND SWIVEL ASSEMBLIES FOR ORAL IRRIGATOR HANDLE

(71) Applicant: WATER PIK, INC., Fort Collins, CO (US)

(72) Inventors: Robert Wagner, Firestone, CO (US); Kurt Taylor, Fort Collins, CO (US); Christina McClard, Fort Collins, CO (US)

(73) Assignee: WATER PIK, INC., Fort Collins, CO (US)

( * ) Notice: Subject to any disclaimer, the term of this patent is extended or adjusted under 35 U.S.C. 154(b) by 297 days.

(21) Appl. No.: 15/844,262

(22) Filed: Dec. 15, 2017

(65) Prior Publication Data
US 2018/0168785 A1    Jun. 21, 2018

Related U.S. Application Data

(60) Provisional application No. 62/435,054, filed on Dec. 15, 2016.

(51) Int. Cl.
*A61C 17/02* (2006.01)
*A61C 17/028* (2006.01)
(Continued)

(52) U.S. Cl.
CPC ........ *A61C 17/0202* (2013.01); *A61C 17/028* (2013.01); *A61C 17/0217* (2013.01); *A61C 1/0061* (2013.01); *A61M 39/1055* (2013.01)

(58) Field of Classification Search
CPC ..... A61C 17/00; A61C 17/02; A61C 17/0202; A61C 17/0205; A61C 17/0208;
(Continued)

(56) References Cited

U.S. PATENT DOCUMENTS

| 555,588 A | 3/1896 | Spencer |
| 1,278,225 A | 9/1918 | Schamberg |
(Continued)

FOREIGN PATENT DOCUMENTS

| CA | 851479 | 9/1970 |
| CH | 655237 | 4/1986 |
(Continued)

OTHER PUBLICATIONS

US RE27,274 E, 01/1972, Mattingly (withdrawn)
(Continued)

*Primary Examiner* — Samchuan C Yao
*Assistant Examiner* — Danielle Roman
(74) *Attorney, Agent, or Firm* — Dorsey & Whitney LLP

(57) ABSTRACT

An oral irrigator handle through which fluid flows to a tip is described. Fluid flows from a fluidically connected hose to the tip during irrigate mode, and fluid flow may be interrupted by selecting a pause mode. The handle includes a mechanically controlled actuator for selecting the pause mode. The actuator may be operably connected to a shuttle valve that is positioned to block fluid flow to the tip during pause mode but not during irrigate mode. The handle may also include a swivel assembly. The swivel assembly prevents rotational movement of either the handle or the hose from being transmitted to the other, such that rotation of the handle will not affect the position of the hose.

16 Claims, 51 Drawing Sheets

(51) Int. Cl.
*A61M 39/10* (2006.01)
*A61C 1/00* (2006.01)

(58) Field of Classification Search
CPC ............ A61C 17/0217; A61C 17/0211; A61C 17/024; A61C 17/028; A61C 17/005; A61C 17/14; A61C 17/036; A61C 17/032; A61C 17/16; A61C 15/00; A61C 1/0061; A61M 35/003; A61M 39/1055; A61M 39/24; A61H 9/00; A61H 9/0007; A61H 9/0021; A61H 13/00; A61H 13/005; A61H 2201/0153; A61H 2201/0157; A61H 2201/1238
USPC .......................................... 251/343, 344, 347
See application file for complete search history.

(56) References Cited

U.S. PATENT DOCUMENTS

| | | |
|---|---|---|
| 1,452,258 A | 4/1923 | Smith |
| 1,464,419 A | 8/1923 | Gill |
| 1,480,310 A | 1/1924 | Smith |
| 1,498,267 A | 6/1924 | Hachman |
| 1,602,742 A | 10/1926 | Bennet |
| 1,650,686 A | 11/1927 | Binks |
| 1,669,889 A | 5/1928 | Andrews et al. |
| 1,681,320 A | 8/1928 | Bergl et al. |
| 1,933,454 A | 10/1933 | Sidney |
| 1,940,111 A | 12/1933 | Austin |
| D93,019 S | 8/1934 | Hose |
| 1,977,782 A | 10/1934 | Roy |
| 2,107,686 A | 2/1938 | Bramsen et al. |
| 2,124,747 A * | 7/1938 | Pieper .................... A61C 17/00 604/249 |
| 2,171,292 A * | 8/1939 | Pieper ................ A61C 17/0202 604/249 |
| D159,872 S | 8/1950 | Skold |
| 2,531,730 A | 11/1950 | Henderson |
| 2,595,666 A | 5/1952 | Hutson |
| 2,669,233 A | 2/1954 | Friend |
| 2,709,227 A | 5/1955 | Foley et al. |
| 2,733,713 A | 2/1956 | Kabnick |
| 2,783,919 A | 3/1957 | Ansell |
| 2,794,437 A | 6/1957 | Tash |
| 2,870,932 A | 1/1959 | Davis |
| 2,984,452 A | 5/1961 | Hooper |
| 3,089,490 A | 5/1963 | Goldberg |
| 3,096,913 A | 7/1963 | Jousson |
| 3,144,867 A | 8/1964 | Trupp et al. |
| D202,041 S | 8/1965 | Burzlaff |
| 3,209,956 A | 10/1965 | McKenzie |
| 3,216,619 A | 11/1965 | Richards et al. |
| 3,225,759 A | 12/1965 | Drapen et al. |
| 3,227,158 A | 1/1966 | Mattingly |
| 3,266,623 A | 8/1966 | Poferl |
| 3,297,558 A | 1/1967 | Hillquist |
| D208,778 S | 10/1967 | Koch |
| D209,202 S | 11/1967 | Fulton et al. |
| D209,203 S | 11/1967 | Mattingly et al. |
| D209,204 S | 11/1967 | St. Clair et al. |
| D209,395 S | 11/1967 | Gilbert |
| D210,018 S | 1/1968 | Mattingly et al. |
| D210,019 S | 1/1968 | Johnson et al. |
| 3,370,214 A | 2/1968 | Aymar |
| 3,391,696 A | 7/1968 | Woodward |
| 3,393,673 A | 7/1968 | Mattingly et al. |
| 3,393,676 A * | 7/1968 | Kummer ................ A61C 17/02 433/28 |
| 3,400,999 A | 9/1968 | Goldstein |
| 3,418,552 A | 12/1968 | Holmes |
| 3,420,228 A | 1/1969 | Kalbfeld |
| 3,425,410 A | 2/1969 | Cammack |
| 3,453,969 A | 7/1969 | Mattingly |
| 3,465,751 A | 9/1969 | Powers |
| 3,467,083 A | 9/1969 | Mattingly |
| 3,467,286 A | 9/1969 | Ostrowsky |
| D215,920 S | 11/1969 | McCarty et al. |
| 3,487,828 A | 1/1970 | Troy |
| 3,489,268 A | 1/1970 | Meierhoefer |
| 3,495,587 A | 2/1970 | Freedman |
| 3,496,933 A | 2/1970 | Lloyd |
| 3,499,440 A | 3/1970 | Gibbs |
| 3,500,824 A | 3/1970 | Gilbert |
| 3,501,203 A | 3/1970 | Falk |
| 3,502,072 A | 3/1970 | Stillman |
| 3,517,669 A | 6/1970 | Buono et al. |
| D218,270 S | 8/1970 | Soper |
| 3,522,801 A | 8/1970 | Robinson |
| 3,532,221 A | 10/1970 | Kaluhiokalani et al. |
| 3,536,065 A | 10/1970 | Moret |
| 3,537,444 A | 11/1970 | Garn |
| 3,538,950 A | 11/1970 | Porteners |
| 3,547,110 A | 12/1970 | Balamuth |
| 3,561,433 A | 2/1971 | Kovach |
| D220,334 S | 3/1971 | Mackay et al. |
| 3,570,525 A | 3/1971 | Borsum |
| 3,572,375 A | 3/1971 | Rosenberg |
| 3,578,884 A | 5/1971 | Jacobson |
| D220,996 S | 6/1971 | Irons |
| 3,583,609 A | 6/1971 | Oppenheimer |
| 3,590,813 A | 7/1971 | Roszyk |
| 3,608,548 A | 9/1971 | Lewis |
| D222,862 S | 1/1972 | Cook |
| 3,636,947 A | 1/1972 | Balamuth |
| 3,651,576 A | 3/1972 | Massa |
| 3,669,101 A | 6/1972 | Kleiner |
| 3,703,170 A | 11/1972 | Ryckman, Jr. |
| 3,718,974 A | 3/1973 | Buchtel et al. |
| 3,747,595 A | 7/1973 | Grossan |
| 3,768,472 A | 10/1973 | Hodosh et al. |
| 3,771,186 A | 11/1973 | Moret et al. |
| 3,783,364 A | 1/1974 | Gallanis et al. |
| 3,809,506 A | 5/1974 | Malcosky |
| 3,809,977 A | 5/1974 | Balamuth et al. |
| 3,811,432 A | 5/1974 | Moret |
| 3,820,532 A | 6/1974 | Eberhardt et al. |
| 3,827,147 A | 8/1974 | Condon |
| 3,837,166 A | 9/1974 | Hiraoka |
| 3,840,795 A | 10/1974 | Roszyk et al. |
| 3,847,145 A | 11/1974 | Grossan |
| 3,851,643 A * | 12/1974 | Musy .................. A61C 17/028 601/162 |
| 3,854,209 A | 12/1974 | Franklin et al. |
| 3,863,628 A | 2/1975 | Vit |
| 3,871,560 A | 3/1975 | Crippa |
| 3,874,506 A | 4/1975 | Hill et al. |
| 3,912,125 A | 10/1975 | Acklin |
| 3,943,628 A | 3/1976 | Kronman et al. |
| 3,959,883 A | 6/1976 | Walls et al. |
| 3,973,558 A | 8/1976 | Stouffer et al. |
| 3,977,084 A | 8/1976 | Sloan |
| 4,001,526 A | 1/1977 | Olson |
| 4,004,302 A | 1/1977 | Hori |
| 4,007,739 A | 2/1977 | Bron et al. |
| 4,013,227 A | 3/1977 | Herrera |
| 4,015,336 A * | 4/1977 | Johnson ................ A61C 17/08 433/95 |
| 4,052,002 A | 10/1977 | Stouffer et al. |
| D246,667 S | 12/1977 | Mackay et al. |
| D246,668 S | 12/1977 | Mackay et al. |
| 4,060,870 A | 12/1977 | Cannarella |
| 4,075,761 A | 2/1978 | Behne et al. |
| 4,078,558 A | 3/1978 | Woog et al. |
| 4,094,311 A | 6/1978 | Hudson |
| 4,108,167 A | 8/1978 | Hickman et al. |
| 4,108,178 A | 8/1978 | Betush |
| 4,109,650 A | 8/1978 | Peclard |
| 4,122,845 A | 10/1978 | Stouffer et al. |
| 4,133,971 A | 1/1979 | Boyd et al. |
| 4,135,501 A | 1/1979 | Leunissan |
| 4,141,352 A | 2/1979 | Ebner et al. |
| 4,144,646 A | 3/1979 | Takemoto et al. |
| 4,149,315 A | 4/1979 | Page, Jr. et al. |

(56) References Cited

U.S. PATENT DOCUMENTS

| | | |
|---|---|---|
| 4,154,375 A | 5/1979 | Bippus |
| 4,160,383 A | 7/1979 | Rauschenberger |
| 4,171,572 A | 10/1979 | Nash |
| 4,182,038 A | 1/1980 | Fleer |
| 4,200,235 A | 4/1980 | Monschke |
| 4,201,200 A | 5/1980 | Hubner |
| 4,210,380 A | 7/1980 | Brzostek |
| 4,215,476 A | 8/1980 | Armstrong |
| 4,219,618 A | 8/1980 | Leonard |
| 4,227,878 A | 10/1980 | Lohn |
| 4,229,634 A | 10/1980 | Hickman et al. |
| 4,236,889 A | 12/1980 | Wright |
| D258,097 S | 2/1981 | Wistrand |
| 4,248,589 A | 2/1981 | Lewis |
| 4,249,899 A | 2/1981 | Davis |
| 4,257,458 A | 3/1981 | Kondo et al. |
| 4,262,799 A | 4/1981 | Perrett |
| 4,266,934 A | 5/1981 | Pernot |
| 4,276,023 A | 6/1981 | Phillips et al. |
| 4,276,880 A | 7/1981 | Malmin |
| 4,302,186 A | 11/1981 | Cammack et al. |
| 4,303,064 A | 12/1981 | Buffa |
| 4,303,070 A | 12/1981 | Ichikawa et al. |
| 4,306,862 A | 12/1981 | Knox |
| 4,315,741 A | 2/1982 | Reichl |
| 4,319,568 A | 3/1982 | Tregoning |
| 4,331,422 A | 5/1982 | Heyman |
| 4,337,040 A | 6/1982 | Cammack et al. |
| 4,340,365 A | 7/1982 | Pisanu |
| 4,340,368 A | 7/1982 | Lococo |
| D266,117 S | 9/1982 | Oberheim |
| 4,353,694 A | 10/1982 | Pelerin |
| 4,363,626 A | 12/1982 | Schmidt et al. |
| 4,365,376 A | 12/1982 | Oda et al. |
| 4,370,131 A | 1/1983 | Banko |
| 4,374,354 A | 2/1983 | Petrovic et al. |
| 4,382,167 A | 5/1983 | Maruyama et al. |
| 4,382,786 A | 5/1983 | Lohn |
| D270,000 S | 8/1983 | Ketler |
| 4,396,011 A | 8/1983 | MacK et al. |
| 4,412,823 A | 11/1983 | Sakai et al. |
| 4,416,628 A | 11/1983 | Cammack |
| 4,442,830 A | 4/1984 | Markau |
| 4,442,831 A | 4/1984 | Trenary |
| 4,452,238 A | 6/1984 | Kerr |
| 4,454,866 A | 6/1984 | Fayen |
| 4,512,769 A | 4/1985 | Kozam et al. |
| 4,517,962 A | 5/1985 | Heckele |
| 4,531,912 A | 7/1985 | Schuss et al. |
| 4,531,913 A | 7/1985 | Taguchi |
| 4,534,340 A | 8/1985 | Kerr et al. |
| 4,552,130 A | 11/1985 | Kinoshita |
| 4,561,214 A | 12/1985 | Inoue |
| D283,374 S | 4/1986 | Cheuk-Yiu |
| 4,585,415 A | 4/1986 | Hommann |
| 4,591,777 A | 5/1986 | McCarty et al. |
| 4,592,728 A | 6/1986 | Davis |
| 4,602,906 A | 7/1986 | Grunenfelder |
| 4,607,627 A | 8/1986 | Leber et al. |
| 4,613,074 A | 9/1986 | Schulze |
| 4,619,009 A | 10/1986 | Rosenstatter |
| 4,619,612 A | 10/1986 | Weber et al. |
| 4,629,425 A | 12/1986 | Detsch |
| 4,636,198 A | 1/1987 | Stade |
| 4,642,037 A | 2/1987 | Fritchman |
| 4,644,937 A | 2/1987 | Hommann |
| 4,645,488 A | 2/1987 | Matukas |
| 4,647,831 A | 3/1987 | O'Malley et al. |
| 4,648,838 A | 3/1987 | Schlachter |
| 4,650,475 A | 3/1987 | Smith et al. |
| 4,655,198 A | 4/1987 | Hommann |
| 4,669,453 A | 6/1987 | Atkinson et al. |
| 4,672,953 A | 6/1987 | DiVito |
| 4,673,396 A | 6/1987 | Urbaniak |
| D291,354 S | 8/1987 | Camens |
| 4,716,352 A | 12/1987 | Hurn et al. |
| 4,749,340 A | 6/1988 | Ikeda et al. |
| 4,770,632 A | 9/1988 | Ryder et al. |
| D298,565 S | 11/1988 | Kohler, Jr. et al. |
| 4,783,321 A | 11/1988 | Spence |
| 4,787,845 A | 11/1988 | Valentine |
| 4,787,847 A | 11/1988 | Martin et al. |
| 4,798,292 A | 1/1989 | Hauze |
| 4,803,974 A | 2/1989 | Powell |
| 4,804,364 A | 2/1989 | Dieras et al. |
| 4,810,148 A | 3/1989 | Aisa et al. |
| 4,818,229 A | 4/1989 | Vasile |
| 4,820,152 A | 4/1989 | Warrin et al. |
| 4,821,923 A | 4/1989 | Skorka |
| 4,824,368 A | 4/1989 | Hickman |
| 4,826,431 A | 5/1989 | Fujimura et al. |
| 4,827,551 A | 5/1989 | Maser et al. |
| 4,832,683 A | 5/1989 | Idemoto et al. |
| 4,854,869 A | 8/1989 | Lawhorn |
| 4,861,340 A | 8/1989 | Smith et al. |
| 4,862,876 A | 9/1989 | Lih-Sheng |
| 4,869,720 A | 9/1989 | Chernack |
| 4,880,382 A | 11/1989 | Moret et al. |
| 4,886,452 A | 12/1989 | Lohn |
| 4,900,252 A | 2/1990 | Liefke et al. |
| 4,902,225 A | 2/1990 | Lohn |
| 4,903,687 A | 2/1990 | Lih-Sheng |
| 4,906,187 A | 3/1990 | Amadera |
| 4,907,744 A | 3/1990 | Jousson |
| 4,915,304 A | 4/1990 | Campani |
| 4,925,450 A | 5/1990 | Imonti et al. |
| 4,928,675 A | 5/1990 | Thornton |
| 4,930,660 A | 6/1990 | Porteous |
| 4,941,459 A | 7/1990 | Mathur |
| 4,950,159 A | 8/1990 | Hansen |
| 4,958,629 A | 9/1990 | Peace et al. |
| 4,958,751 A | 9/1990 | Curtis et al. |
| 4,959,199 A | 9/1990 | Brewer |
| 4,961,698 A | 10/1990 | Vlock |
| 4,966,551 A | 10/1990 | Betush |
| 4,969,874 A | 11/1990 | Michel et al. |
| 4,973,246 A | 11/1990 | Black |
| 4,973,247 A | 11/1990 | Varnes et al. |
| 4,973,250 A | 11/1990 | Milman |
| 4,975,054 A | 12/1990 | Esrock |
| 4,979,503 A | 12/1990 | Chernack |
| 4,979,504 A | 12/1990 | Mills |
| 4,989,590 A | 2/1991 | Baum et al. |
| 4,998,880 A | 3/1991 | Nerli |
| 5,013,241 A | 5/1991 | Von Gutfeld et al. |
| 5,014,884 A | 5/1991 | Wunsch |
| 5,019,054 A | 5/1991 | Clement et al. |
| 5,027,798 A | 7/1991 | Primiano |
| 5,029,576 A | 7/1991 | Evans, Sr. |
| 5,033,617 A | 7/1991 | Hartwein et al. |
| 5,033,961 A | 7/1991 | Kandler et al. |
| D318,918 S | 8/1991 | Hartwein |
| 5,046,486 A | 9/1991 | Grulke et al. |
| 5,049,071 A | 9/1991 | Davis et al. |
| 5,060,825 A | 10/1991 | Palmer et al. |
| 5,061,180 A | 10/1991 | Wiele |
| 5,062,795 A | 11/1991 | Woog |
| 5,064,168 A | 11/1991 | Raines et al. |
| D322,314 S | 12/1991 | Ohbayashi |
| 5,071,346 A | 12/1991 | Domaas |
| 5,082,115 A | 1/1992 | Hutcheson |
| 5,082,443 A | 1/1992 | Lohn |
| 5,085,317 A | 2/1992 | Jensen et al. |
| 5,086,756 A | 2/1992 | Powell |
| 5,095,893 A | 3/1992 | Rawden, Jr. |
| 5,098,291 A | 3/1992 | Curtis et al. |
| 5,098,676 A | 3/1992 | Brooks, Jr. |
| 5,100,319 A | 3/1992 | Baum |
| 5,117,871 A | 6/1992 | Gardner et al. |
| 5,125,835 A | 6/1992 | Young |
| 5,127,831 A | 7/1992 | Bab |
| 5,142,723 A | 9/1992 | Lustig et al. |
| 5,150,841 A | 9/1992 | Silvenis et al. |
| 5,172,810 A | 12/1992 | Brewer |

(56) References Cited

U.S. PATENT DOCUMENTS

| | | |
|---|---|---|
| 5,173,273 A | 12/1992 | Brewer |
| 5,183,035 A | 2/1993 | Weir |
| 5,197,458 A | 3/1993 | Ito et al. |
| 5,197,460 A | 3/1993 | Ito et al. |
| 5,199,871 A | 4/1993 | Young |
| 5,203,697 A | 4/1993 | Malmin |
| 5,203,769 A | 4/1993 | Clement et al. |
| 5,204,004 A | 4/1993 | Johnston et al. |
| 5,208,933 A | 5/1993 | Lustig et al. |
| 5,215,193 A | 6/1993 | Dennis |
| 5,218,956 A | 6/1993 | Handler et al. |
| 5,220,914 A | 6/1993 | Thompson |
| 5,228,646 A | 7/1993 | Raines |
| 5,230,624 A | 7/1993 | Wolf et al. |
| 5,232,687 A | 8/1993 | Geimer |
| 5,235,968 A | 8/1993 | Woog |
| 5,241,714 A | 9/1993 | Barry |
| 5,246,367 A | 9/1993 | Ito et al. |
| 5,252,064 A | 10/1993 | Baum et al. |
| D341,200 S | 11/1993 | Yoshimoto |
| 5,257,933 A | 11/1993 | Jousson |
| 5,261,448 A | 11/1993 | Furuya et al. |
| D341,943 S | 12/1993 | Si-Hoe |
| 5,267,586 A | 12/1993 | Jankavaara |
| 5,269,684 A | 12/1993 | Fischer |
| 5,281,137 A | 1/1994 | Jousson |
| 5,281,139 A | 1/1994 | Frank et al. |
| 5,282,745 A | 2/1994 | Wiltrout et al. |
| 5,286,192 A | 2/1994 | Dixon |
| 5,286,201 A | 2/1994 | Yu |
| 5,295,832 A | 3/1994 | Evans |
| 5,297,962 A | 3/1994 | O'Connor et al. |
| D346,212 S | 4/1994 | Hosl |
| 5,301,381 A | 4/1994 | Klupt |
| 5,302,123 A | 4/1994 | Bechard |
| 5,317,691 A | 5/1994 | Traeger |
| 5,321,865 A | 6/1994 | Kaeser |
| 5,323,770 A | 6/1994 | Ito et al. |
| 5,331,704 A | 7/1994 | Rosen et al. |
| 5,344,317 A | 9/1994 | Pacher et al. |
| 5,346,677 A | 9/1994 | Risk |
| D351,892 S | 10/1994 | Wolf et al. |
| 5,360,338 A | 11/1994 | Waggoner |
| 5,368,548 A | 11/1994 | Jousson |
| 5,370,534 A | 12/1994 | Wolf et al. |
| D354,168 S | 1/1995 | Hartwein |
| D354,559 S | 1/1995 | Knute |
| 5,378,149 A | 1/1995 | Stropko |
| 5,380,201 A | 1/1995 | Kawata |
| D356,864 S | 3/1995 | Woog |
| 5,399,089 A | 3/1995 | Eichman et al. |
| D358,883 S | 5/1995 | Vos |
| 5,456,672 A | 10/1995 | Diederich et al. |
| 5,465,445 A | 11/1995 | Yeh |
| 5,467,495 A | 11/1995 | Boland et al. |
| 5,468,148 A | 11/1995 | Ricks |
| 5,470,305 A | 11/1995 | Arnett et al. |
| 5,474,450 A | 12/1995 | Chronister |
| 5,474,451 A | 12/1995 | Dalrymple et al. |
| 5,476,379 A | 12/1995 | Disel |
| 5,484,281 A | 1/1996 | Renow et al. |
| 5,487,877 A | 1/1996 | Choi |
| 5,490,779 A | 2/1996 | Malmin |
| 5,505,916 A | 4/1996 | Berry, Jr. |
| D369,656 S | 5/1996 | Vos |
| D370,125 S | 5/1996 | Craft et al. |
| 5,525,058 A | 6/1996 | Gallant et al. |
| 5,526,841 A | 6/1996 | Detsch et al. |
| 5,540,587 A | 7/1996 | Malmin |
| 5,547,374 A | 8/1996 | Coleman |
| D373,631 S | 9/1996 | Maeda et al. |
| 5,554,014 A | 9/1996 | Becker |
| 5,554,025 A | 9/1996 | Kinsel |
| 5,556,001 A | 9/1996 | Weissman et al. |
| 5,564,629 A | 10/1996 | Weissman et al. |
| D376,893 S | 12/1996 | Gornet |
| D377,091 S | 12/1996 | Scott, Sr. |
| 5,613,259 A | 3/1997 | Craft et al. |
| 5,616,028 A | 4/1997 | Hafele et al. |
| 5,626,472 A | 5/1997 | Pennetta |
| 5,634,791 A | 6/1997 | Matsuura et al. |
| 5,636,987 A | 6/1997 | Serfaty |
| 5,640,735 A | 6/1997 | Manning |
| D382,407 S | 8/1997 | Craft et al. |
| 5,653,591 A | 8/1997 | Loge |
| 5,659,995 A | 8/1997 | Hoffman |
| 5,667,483 A | 9/1997 | Santos |
| D386,576 S | 11/1997 | Wang et al. |
| 5,683,192 A | 11/1997 | Kilfoil |
| 5,685,829 A | 11/1997 | Allen |
| 5,685,851 A | 11/1997 | Murphy et al. |
| 5,697,784 A | 12/1997 | Hafele et al. |
| D388,612 S | 1/1998 | Stutzer et al. |
| D388,613 S | 1/1998 | Stutzer et al. |
| D389,091 S | 1/1998 | Dickinson |
| 5,709,545 A | 1/1998 | Johnston et al. |
| D390,934 S | 2/1998 | McKeone |
| 5,716,007 A | 2/1998 | Nottingham et al. |
| 5,718,668 A | 2/1998 | Arnett et al. |
| 5,746,595 A | 5/1998 | Ford |
| 5,749,726 A | 5/1998 | Kinsel |
| 5,759,502 A | 6/1998 | Spencer et al. |
| 5,779,471 A | 7/1998 | Tseng et al. |
| 5,779,654 A | 7/1998 | Foley et al. |
| 5,795,153 A | 8/1998 | Rechmann |
| 5,796,325 A | 8/1998 | Lundell et al. |
| 5,833,065 A | 11/1998 | Burgess |
| 5,836,030 A | 11/1998 | Hazeu et al. |
| D402,744 S | 12/1998 | Zuege |
| 5,851,079 A | 12/1998 | Horstman et al. |
| D403,511 S | 1/1999 | Serbinski |
| D406,334 S | 3/1999 | Rosenthal et al. |
| 5,876,201 A | 3/1999 | Wilson et al. |
| D408,511 S | 4/1999 | Allen et al. |
| 5,901,397 A | 5/1999 | Häfele et al. |
| 5,934,902 A | 8/1999 | Abahusayn |
| D413,975 S | 9/1999 | Maeda |
| D416,999 S | 11/1999 | Miyamoto |
| D417,082 S | 11/1999 | Classen et al. |
| 5,993,402 A | 11/1999 | Sauer et al. |
| 6,030,215 A | 2/2000 | Ellion et al. |
| 6,038,960 A | 3/2000 | Fukushima et al. |
| 6,039,180 A | 3/2000 | Grant |
| 6,047,429 A | 4/2000 | Wu |
| D424,181 S | 5/2000 | Caplow |
| D425,615 S | 5/2000 | Bachman et al. |
| D425,981 S | 5/2000 | Bachman et al. |
| 6,056,548 A | 5/2000 | Neuberger et al. |
| 6,056,710 A | 5/2000 | Bachman et al. |
| D426,633 S | 6/2000 | Bachman et al. |
| 6,089,865 A | 7/2000 | Edgar |
| 6,116,866 A | 9/2000 | Tomita et al. |
| 6,120,755 A | 9/2000 | Jacobs |
| 6,124,699 A | 9/2000 | Suzuki et al. |
| D434,500 S | 11/2000 | Pollock et al. |
| 6,159,006 A | 12/2000 | Cook et al. |
| 6,164,967 A | 12/2000 | Sale et al. |
| D435,905 S | 1/2001 | Bachman et al. |
| D437,049 S | 1/2001 | Hartwein |
| 6,193,512 B1 | 2/2001 | Wallace |
| 6,193,932 B1 | 2/2001 | Wu et al. |
| 6,199,239 B1 | 3/2001 | Dickerson |
| 6,200,134 B1 | 3/2001 | Kovac |
| D439,781 S | 4/2001 | Spore |
| 6,217,835 B1 | 4/2001 | Riley et al. |
| D441,861 S | 5/2001 | Hafliger |
| 6,233,773 B1 | 5/2001 | Karge et al. |
| 6,234,205 B1 | 5/2001 | D'Amelio et al. |
| 6,237,178 B1 | 5/2001 | Krammer et al. |
| 6,247,929 B1 | 6/2001 | Bachman et al. |
| 6,280,190 B1 | 8/2001 | Hoffman |
| D448,236 S | 9/2001 | Murray |
| 6,293,792 B1 | 9/2001 | Hanson |
| D449,884 S | 10/2001 | Tobin et al. |

(56) References Cited

U.S. PATENT DOCUMENTS

| | | |
|---|---|---|
| D453,453 S | 2/2002 | Lun |
| D455,201 S | 4/2002 | Jones |
| D455,203 S | 4/2002 | Jones |
| 6,363,565 B1 | 4/2002 | Paffrath |
| D457,949 S | 5/2002 | Krug |
| D464,799 S | 10/2002 | Crossman et al. |
| 6,468,482 B1 | 10/2002 | Frieze et al. |
| 6,475,173 B1 | 11/2002 | Bachman et al. |
| 6,485,451 B1 | 11/2002 | Roberts et al. |
| 6,497,375 B1 | 12/2002 | Srinath et al. |
| 6,497,572 B2 | 12/2002 | Hood et al. |
| 6,502,584 B1 | 1/2003 | Fordham |
| D470,660 S | 2/2003 | Schaber |
| 6,532,837 B1 | 3/2003 | Magussen, Jr. |
| 6,558,344 B2 | 5/2003 | McKinnon et al. |
| 6,561,808 B2 | 5/2003 | Neuberger et al. |
| D475,346 S | 6/2003 | McCurrach et al. |
| D476,743 S | 7/2003 | D'Silva et al. |
| 6,589,477 B1 | 7/2003 | Frieze et al. |
| 6,602,071 B1 | 8/2003 | Ellion et al. |
| 6,632,091 B1 | 10/2003 | Cise et al. |
| D482,451 S | 11/2003 | Page et al. |
| 6,640,999 B2 | 11/2003 | Peterson |
| 6,647,577 B2 | 11/2003 | Tam |
| 6,659,674 B2 | 12/2003 | Carlucci et al. |
| 6,663,386 B1 | 12/2003 | Moelsgaard |
| 6,669,059 B2 | 12/2003 | Mehta |
| D484,971 S | 1/2004 | Hartwein |
| 6,681,418 B1 | 1/2004 | Bierend |
| D486,573 S | 2/2004 | Callaghan et al. |
| 6,689,078 B1 | 2/2004 | Rehkemper et al. |
| 6,699,208 B2 | 3/2004 | Bachman et al. |
| 6,719,561 B2 | 4/2004 | Gugel et al. |
| D489,183 S | 5/2004 | Akahori et al. |
| 6,739,782 B1 | 5/2004 | Rehkemper et al. |
| 6,740,053 B2 | 5/2004 | Kaplowitz |
| D490,899 S | 6/2004 | Gagnon |
| D491,728 S | 6/2004 | Jimenez |
| D492,996 S | 7/2004 | Rehkemper et al. |
| 6,761,324 B2 | 7/2004 | Chang |
| 6,766,549 B2 | 7/2004 | Klupt |
| D495,142 S | 8/2004 | Berde |
| D495,143 S | 8/2004 | Berde |
| 6,779,216 B2 | 8/2004 | Davies et al. |
| 6,783,004 B1 | 8/2004 | Rinner |
| 6,783,505 B1 | 8/2004 | Lai |
| 6,796,796 B2 | 9/2004 | Segal |
| 6,808,331 B2 | 10/2004 | Hall et al. |
| D498,643 S | 11/2004 | Pryor |
| 6,814,259 B1 | 11/2004 | Foster et al. |
| D499,885 S | 12/2004 | Xi |
| 6,835,181 B2 | 12/2004 | Hippensteel |
| D500,599 S | 1/2005 | Callaghan |
| 6,836,917 B2 | 1/2005 | Blaustein et al. |
| 6,837,708 B2 | 1/2005 | Chen et al. |
| 6,884,069 B2 | 4/2005 | Goldman |
| 6,902,337 B1 | 6/2005 | Kuo |
| 6,907,879 B2 | 6/2005 | Drinan et al. |
| D509,585 S | 9/2005 | Kling et al. |
| D513,638 S | 1/2006 | Pan |
| D515,215 S | 2/2006 | Wang |
| D522,652 S | 6/2006 | Massey |
| 7,080,980 B2 | 7/2006 | Klupt |
| D529,661 S | 10/2006 | Schmidt |
| D530,010 S | 10/2006 | Luettgen et al. |
| 7,117,555 B2 | 10/2006 | Fattori et al. |
| D532,570 S | 11/2006 | Vizcarra |
| 7,131,838 B2 | 11/2006 | Suzuki et al. |
| D533,720 S | 12/2006 | Vu |
| 7,147,468 B2 | 12/2006 | Snyder et al. |
| D538,474 S | 3/2007 | Sheppard et al. |
| D548,334 S | 8/2007 | Izumi |
| D550,097 S | 9/2007 | Lepoitevin |
| D553,980 S | 10/2007 | VerWeyst |
| 7,276,035 B2 | 10/2007 | Lu |
| 7,314,456 B2 | 1/2008 | Shaw |
| D565,175 S | 3/2008 | Boyd et al. |
| 7,344,510 B1 | 3/2008 | Yande |
| D565,713 S | 4/2008 | Gao |
| 7,367,803 B2 | 5/2008 | Egeresi |
| D574,952 S | 8/2008 | Boyd et al. |
| 7,414,337 B2 | 8/2008 | Wilkinson et al. |
| D577,198 S | 9/2008 | Jimenez |
| D577,814 S | 9/2008 | Seki et al. |
| D581,279 S | 11/2008 | Oates |
| 7,455,521 B2 | 11/2008 | Fishburne, Jr. |
| 7,469,440 B2 | 12/2008 | Boland et al. |
| D585,132 S | 1/2009 | Pukall |
| D588,262 S | 3/2009 | Pukall |
| 7,500,584 B2 | 3/2009 | Schutz |
| D590,492 S | 4/2009 | Powell |
| D592,748 S | 5/2009 | Boulton |
| D595,136 S | 6/2009 | Canamasas Puigbo |
| D601,694 S | 10/2009 | Rocklin |
| D601,697 S | 10/2009 | Sobeich et al. |
| D603,708 S | 11/2009 | Handy |
| D608,430 S | 1/2010 | Slothower |
| 7,670,141 B2 | 3/2010 | Thomas et al. |
| 7,677,888 B1 | 3/2010 | Halm |
| D613,550 S | 4/2010 | Picozza et al. |
| D621,949 S | 8/2010 | Seki et al. |
| D622,928 S | 9/2010 | Griebel |
| D623,376 S | 9/2010 | Griebel |
| D625,406 S | 10/2010 | Seki et al. |
| 7,814,585 B1 | 10/2010 | Reich |
| D629,884 S | 12/2010 | Stephens |
| 7,857,623 B2 | 12/2010 | Grez |
| 7,862,536 B2 | 1/2011 | Chen et al. |
| 7,959,597 B2 | 6/2011 | Baker et al. |
| D640,872 S | 7/2011 | Nanda |
| D648,539 S | 11/2011 | Wai |
| D651,409 S | 1/2012 | Papenfu |
| D651,805 S | 1/2012 | Hay |
| D653,340 S | 1/2012 | Goerge et al. |
| 8,113,832 B2 | 2/2012 | Snyder et al. |
| D655,380 S | 3/2012 | Taylor |
| D658,381 S | 5/2012 | Gebski |
| D658,538 S | 5/2012 | Korzeniowski |
| 8,220,726 B2 | 7/2012 | Qiu et al. |
| D666,912 S | 9/2012 | Kawai |
| 8,256,979 B2 | 9/2012 | Hilscher et al. |
| D668,339 S | 10/2012 | Luoto |
| D669,169 S | 10/2012 | Washington et al. |
| 8,297,534 B2 | 10/2012 | Li et al. |
| D670,373 S | 11/2012 | Taylor et al. |
| D670,958 S | 11/2012 | Picozza et al. |
| D671,637 S | 11/2012 | Gebski et al. |
| D672,018 S | 12/2012 | Bucher |
| 8,366,024 B2 | 2/2013 | Leber et al. |
| 8,403,577 B2 | 3/2013 | Khoshnevis |
| 8,403,665 B2 | 3/2013 | Thomas et al. |
| 8,408,483 B2 | 4/2013 | Boyd et al. |
| 8,418,300 B2 | 4/2013 | Miller et al. |
| D686,311 S | 7/2013 | Mori |
| D694,378 S | 11/2013 | Bates |
| D694,398 S | 11/2013 | Taylor |
| D700,343 S | 2/2014 | Liu |
| D702,819 S | 4/2014 | Garland |
| D702,821 S | 4/2014 | Garland |
| D707,350 S | 6/2014 | Woodard |
| D709,183 S | 7/2014 | Kemlein |
| D714,929 S | 10/2014 | Kim et al. |
| D714,930 S | 10/2014 | Kim et al. |
| D717,412 S | 11/2014 | Bucher |
| D717,427 S | 11/2014 | Kim |
| D718,855 S | 12/2014 | Kim et al. |
| D723,387 S | 3/2015 | Fath |
| D725,770 S | 3/2015 | Kim et al. |
| D731,640 S | 6/2015 | Kim et al. |
| D735,305 S | 7/2015 | Obara |
| D740,936 S | 10/2015 | Kim et al. |
| D745,329 S | 12/2015 | Ong |
| D746,975 S | 1/2016 | Schenck |
| D747,464 S | 1/2016 | Taylor |

(56) References Cited

U.S. PATENT DOCUMENTS

| | | | |
|---|---|---|---|
| D754,330 S | 4/2016 | Kim et al. |
| D756,122 S | 5/2016 | Taylor |
| D764,051 S | 8/2016 | Wang |
| D766,423 S | 9/2016 | Kim et al. |
| D772,396 S | 11/2016 | Kim et al. |
| D772,397 S | 11/2016 | Kim et al. |
| D774,651 S | 12/2016 | Kaib |
| D776,253 S | 1/2017 | Li |
| D782,326 S | 3/2017 | Fath |
| D782,656 S | 3/2017 | Au |
| D786,422 S | 5/2017 | Au |
| 9,642,677 B2 | 5/2017 | Luettgen et al. |
| D788,907 S | 6/2017 | Kim |
| D798,440 S | 9/2017 | Kim |
| D802,119 S | 11/2017 | Kim |
| D809,650 S | 2/2018 | Kim |
| 2002/0090252 A1 | 7/2002 | Hall et al. |
| 2002/0108193 A1 | 8/2002 | Gruber |
| 2002/0119415 A1 | 8/2002 | Bailey |
| 2002/0152565 A1 | 10/2002 | Klupt |
| 2003/0060743 A1 | 3/2003 | Chang |
| 2003/0098249 A1 | 5/2003 | Rollock |
| 2003/0162146 A1 | 8/2003 | Shortt et al. |
| 2003/0204155 A1 | 10/2003 | Egeresi |
| 2003/0213075 A1 | 11/2003 | Hui et al. |
| 2004/0045107 A1 | 3/2004 | Egeresi |
| 2004/0076921 A1 | 4/2004 | Gofman et al. |
| 2004/0122377 A1 | 6/2004 | Fischer et al. |
| 2004/0126730 A1 | 7/2004 | Panagotacos |
| 2004/0180569 A1 | 10/2004 | Chiou |
| 2004/0209222 A1 | 10/2004 | Snyder |
| 2005/0049620 A1 | 3/2005 | Chang |
| 2005/0064371 A1 | 3/2005 | Soukos et al. |
| 2005/0101894 A1 | 5/2005 | Hippensteel |
| 2005/0102773 A1 | 5/2005 | Obermann et al. |
| 2005/0144745 A1 | 7/2005 | Russell |
| 2005/0177079 A1 | 8/2005 | Pan |
| 2005/0271531 A1 | 12/2005 | Brown et al. |
| 2006/0008373 A1 | 1/2006 | Schutz |
| 2006/0010624 A1 | 1/2006 | Cleland |
| 2006/0026784 A1 | 2/2006 | Moskovich et al. |
| 2006/0057539 A1 | 3/2006 | Sodo |
| 2006/0078844 A1 | 4/2006 | Goldman et al. |
| 2006/0079818 A1 | 4/2006 | Yande |
| 2006/0207052 A1 | 9/2006 | Tran |
| 2007/0082316 A1 | 4/2007 | Zhadanov et al. |
| 2007/0082317 A1 | 4/2007 | Chuang |
| 2007/0113360 A1 | 5/2007 | Tsai |
| 2007/0202459 A1 | 8/2007 | Boyd et al. |
| 2007/0203439 A1 | 8/2007 | Boyd et al. |
| 2007/0254260 A1 | 11/2007 | Alden |
| 2008/0189951 A1 | 8/2008 | Molema et al. |
| 2008/0213719 A1 | 9/2008 | Giniger et al. |
| 2008/0253906 A1 | 10/2008 | Strong |
| 2009/0070949 A1 | 3/2009 | Sagel et al. |
| 2009/0071267 A1 | 3/2009 | Mathus et al. |
| 2009/0082706 A1 | 3/2009 | Shaw |
| 2009/0124945 A1 | 5/2009 | Reich et al. |
| 2009/0139351 A1 | 6/2009 | Reichmuth |
| 2009/0163839 A1 | 6/2009 | Alexander |
| 2009/0188780 A1 | 7/2009 | Watanabe |
| 2009/0281454 A1 | 11/2009 | Baker et al. |
| 2010/0010524 A1 | 1/2010 | Barrington |
| 2010/0015566 A1 | 1/2010 | Shaw |
| 2010/0049177 A1 | 2/2010 | Boone, III et al. |
| 2010/0190132 A1 | 7/2010 | Taylor et al. |
| 2010/0239998 A1 | 9/2010 | Snyder et al. |
| 2010/0261134 A1 | 10/2010 | Boyd et al. |
| 2010/0261137 A1 | 10/2010 | Boyd et al. |
| 2010/0326536 A1 | 12/2010 | Nan |
| 2010/0330527 A1 | 12/2010 | Boyd et al. |
| 2011/0027749 A1 | 2/2011 | Syed |
| 2011/0076090 A1 | 3/2011 | Wu et al. |
| 2011/0097683 A1 | 4/2011 | Boyd et al. |
| 2011/0139826 A1 | 6/2011 | Hair et al. |
| 2011/0144588 A1 | 6/2011 | Taylor et al. |
| 2011/0184341 A1 | 7/2011 | Baker et al. |
| 2011/0307039 A1 | 12/2011 | Cornell |
| 2012/0021374 A1 | 1/2012 | Cacka et al. |
| 2012/0045730 A1 | 2/2012 | Snyder et al. |
| 2012/0064480 A1 | 3/2012 | Hegemann |
| 2012/0077145 A1 | 3/2012 | Tsurukawa |
| 2012/0141952 A1 | 6/2012 | Snyder et al. |
| 2012/0179118 A1 | 7/2012 | Hair |
| 2012/0189976 A1 | 7/2012 | McDonough et al. |
| 2012/0266396 A1 | 10/2012 | Leung |
| 2012/0277663 A1 | 11/2012 | Millman et al. |
| 2012/0277677 A1 | 11/2012 | Taylor et al. |
| 2012/0277678 A1 | 11/2012 | Taylor et al. |
| 2012/0279002 A1 | 11/2012 | Sokol et al. |
| 2012/0295220 A1 | 11/2012 | Thomas et al. |
| 2013/0089832 A1 | 4/2013 | Lee |
| 2013/0295520 A1 | 11/2013 | Hsieh |
| 2014/0106296 A1 | 4/2014 | Woodard et al. |
| 2014/0193774 A1 | 7/2014 | Snyder et al. |
| 2014/0259474 A1 | 9/2014 | Sokol et al. |
| 2014/0272769 A1 | 9/2014 | Luettgen et al. |
| 2014/0272782 A1 | 9/2014 | Luettgen et al. |
| 2014/0352088 A1 | 12/2014 | Wu |
| 2015/0004559 A1 | 1/2015 | Luettgen et al. |
| 2015/0147717 A1 | 5/2015 | Taylor et al. |
| 2015/0173850 A1 | 6/2015 | Garrigues et al. |
| 2015/0182319 A1 | 7/2015 | Wagner et al. |
| 2016/0100921 A1 | 4/2016 | Ungar |
| 2016/0151133 A1 | 6/2016 | Luettgen et al. |
| 2017/0049530 A1 | 2/2017 | Cacka |
| 2017/0209246 A1 | 7/2017 | Williams et al. |
| 2017/0239132 A1 | 8/2017 | Luettgen et al. |
| 2017/0252251 A1 | 9/2017 | Williams et al. |

FOREIGN PATENT DOCUMENTS

| | | |
|---|---|---|
| CN | 204049908 | 12/2014 |
| DE | 1466963 | 5/1969 |
| DE | 2019003 | 11/1971 |
| DE | 2409752 | 9/1975 |
| DE | 2545936 | 4/1977 |
| DE | 2714876 | 10/1978 |
| DE | 2910982 | 2/1980 |
| DE | 3101941 A1 | 8/1982 |
| DE | 3346651 | 7/1985 |
| EP | 0023672 | 7/1980 |
| EP | 0515983 | 2/1992 |
| EP | 1825827 | 8/2007 |
| FR | 2556954 | 6/1985 |
| FR | 2654627 | 5/1991 |
| GB | 838564 | 6/1960 |
| GB | 1182031 | 2/1970 |
| GB | 1456322 A | 11/1976 |
| GB | 2018605 | 10/1979 |
| JP | 2-134150 | 5/1990 |
| JP | 2009-39455 | 2/2009 |
| KR | 20100028231 A | 3/2010 |
| KR | 20120126265 | 11/2012 |
| WO | WO95/016404 | 6/1995 |
| WO | WO01/10327 | 2/2001 |
| WO | WO04/021958 | 3/2004 |
| WO | WO04/039205 | 5/2004 |
| WO | WO2004/060259 | 7/2004 |
| WO | WO2004/062518 | 7/2004 |
| WO | WO2008/070730 | 6/2008 |
| WO | WO2008/157585 | 12/2008 |
| WO | WO2013/124691 | 8/2013 |

OTHER PUBLICATIONS

International Search Report dated May 24, 2018, in PCT Application No. PCT/US2017/066831, 5 pages.

Written Opinion dated May 24, 2018, in PCT Application No. PCT/US2017/066731, 7 pages.

The Right Tool, Electron Fusion Devices, Inc., 2 pages, at least as early as Feb. 1991.

Japanese Packaging, 2 pages, at least as early as Dec. 2002.

(56) References Cited

OTHER PUBLICATIONS

Japanese Instruction Brochure, 20 pages, at least as early as Dec. 2002.
Brochure: Woog International, "You have a 98% chance of getting gum disease. Unless you read this.", Lancaster, Pennsylvania, 5 pages, Feb. 1987.
Brochure: Woog International, "We put the control of home dental care back into the hands of the professional", Lancaster, Pennsylvania, 2 pages, Feb. 1987.
Brochure: Woog International, "Products at a Glance: Home Dental Care System" Woog Orajet, 3 pages, at least as early as Dec. 18, 1998.
Website: http://www.just4teeth.com/product/Panasonic/Panasonic_Portable_Irrigator.htm, 2 pages, at least as early as Jun. 20, 2003.
Website: http://www.videodirectstore.com/store/merchant.mv?Screen=Prod&Product_Code=EW1' . . . , 2 pages, at least as early as Jun. 20, 2003.
Website: http://products.consumerguide.com/cp/family/review/index.cfm/id/18742, 2 pages, at least as early as Jun. 20, 2003.
Website: http://www.racekarteng.com/images/walbroparts.gif and http://www.muller.net/mullermachine/docs/walbro1.html, 4 pages, at least as early as Jun. 20, 2003.
European Search Report, EPO Application No. 07250799.9, dated Jul. 5, 2007.
European Search Report, EPO Application No. 07252693.2, 14 pages, dated Apr. 28, 2008.
European Examination Report, EPO Application No. 07250799.9, dated Feb. 5, 2009.
International Search Report, Application No. PCT/US2010/028180, 2 pages, dated May 18, 2010.
International Search Report, PCT/US2010/060800, 2 pages, dated Feb. 11, 2011.
International Search Report, PCT/US2011/052795, 10 pages, dated Jan. 17, 2012.
Waterpik SinuSense Website: http://www.insightsbyapril.com/2012/03/waterpik-natural-remedy-for-sinus.html, 8 pages, retrieved on May 31, 2012.
Website: https://www.waterpik.com/about-us/, 3 pages.
Waterpik WP 350W Oral Irrigator. Dentist.net. Copyright date 2013. Date accessed: Mar. 30, 2017, 2 pages <http://www.dentalhoo.com/waterpik-wp350.asp>.
IPik Portable Oral Irrigator. AliExpress. Date reviewed: Oct. 5, 2016. <https://www.allexpress.com/ . . . e-Oral-Care-Product-Nasal-Irrigator-Tooth-Flosser-Water/1525541997. html?aff_platform=aaf&cpt=1490913714609&sk=yfAeyJa&aff_trace_key=c5a300c4f02e46d08c042f5292e1762f-1490913714609-07517-yfAeyJa>, 18 pages.
Brite Leafs Professional Portable 2-in-1 Nasal Sinus & Oral Irrigator. Brite Leafs. Copyright date 2012, <http://www.briteleafs.com/product6.html> , 1 page.
Ali Express. Date reviewed: Jan. 12, 2017. <https://www.aliexpress.com/item/Cordless-Water-Floss-Portable-Oral-Irrigator-Dental-Water-Flosser-Waterpic-Whatpick-Dental-Water-Pic-Whater-Pick/32769416341.html?spm=2114.40010308.4.75.Owuzfj>.
Suvo. "Helical Gears vs Spur Gears—Advantages and Disadvantages Compared." Brighthub Engineering, Aug. 18, 2010, www.brighthubengineering.com/manufacturing-technology/33535-helical-gears-vs-spur-gears/., 7 pages.
Waterpik ADA Accepted WP-663, posted at amazon.com, earliest date reviewed on Feb. 6, 2014, [online], acquired on Feb. 12, 2018. Available from Internet, <URL: https://www.amazon.com/Waterpik-Accepted-WP-663-Aquarius-Flosser/dp/B072JFVXSY/ref=cm_cr_arp_d_product_top?ie=UTF8&th=1> (Year: 2014).
Waterpik Classic Professional Water Flosser, WP-72, posted at amazon.com, earliest date reviewed on Mar. 5, 2016, [online], acquired on Feb. 23, 2018. Available from Internet, <URL: https://www.amazon.com/Waterpik-Classic-Professional-Flosser-WP-72/dp/B00HFQQOU6/ref=cm_cr_arp_d_product_top?ie=UTF8> (Year: 2016).

* cited by examiner

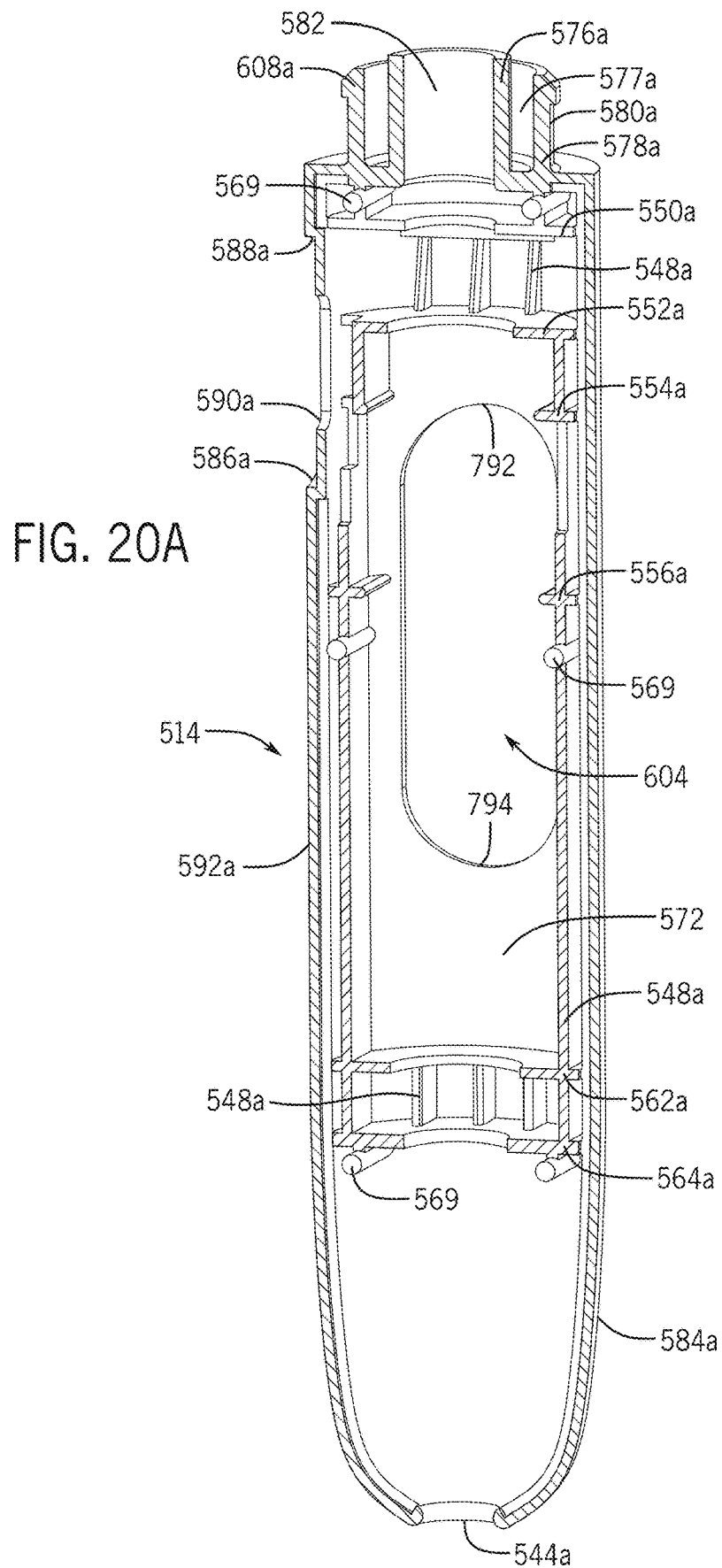

PAUSE VALVE AND SWIVEL ASSEMBLIES FOR ORAL IRRIGATOR HANDLE

CROSS REFERENCE TO RELATED APPLICATIONS

This application claims the benefit of priority pursuant to 35 U.S.C. § 119(e) of U.S. provisional application No. 62/435,054 filed 15 Dec. 2016 entitled "Pause valve and swivel assemblies for oral irrigator handle," which is hereby incorporated herein by reference in its entirety.

TECHNICAL FIELD

The present disclosure relates to health and personal hygiene equipment and more particularly, to oral irrigators.

BACKGROUND

Oral irrigators, or water flossers, typically are used to clean a user's teeth and gums by discharging a pressurized fluid stream into a user's oral cavity. The fluid impacts the teeth and gums to remove debris. Often, the oral irrigator includes a fluid supply, such as a reservoir, that is fluidically connected by a hose and pump to an oral irrigator tip, often through a handle. Some oral irrigators include actuators to pause fluid flow through the handle without turning off power to the irrigator. But these often include electrical circuitry within the handle and in close proximity to fluid conduits, which creates a safety hazard. Oral irrigators with such electrical actuators are also expensive to manufacture.

A user of an oral irrigator often rotates either the handle or the tip relative to the handle in order to direct the fluid to a desired location as well as to hold the handle in a comfortable position. However, the hose can become tangled as the user moves the handle to different positions and orientations with respect to the reservoir in a base unit. The tangles can reduce the effective length of the hose and can hinder storage of the handle in the base unit, both of which make the oral irrigator difficult to use.

The information included in this Background section of the specification, including any references cited herein and any description or discussion thereof, is included for technical reference purposes only and is not to be regarded as subject matter by which the scope of the invention as defined in the claims is to be bound.

SUMMARY

The technology disclosed herein relates to an oral irrigator handle. Fluid flows from a hose through the handle to an attached tip during irrigate mode. The handle includes a pause actuator that engages a flow restrictor to effect a pause mode, which allows a user to interrupt fluid flow to the tip without removing his or her hand from the handle and without turning off power to the oral irrigator. The pause mode is mechanically controlled without electrical components. The handle also includes a swivel assembly fluidically coupled to the hose. The swivel assembly minimizes or prevents translation of rotational movement of the handle and the hose relative to the other.

In one exemplary embodiment of the handle disclosed herein, the handle includes a housing, a fluid inlet into the housing, a fluid outlet from the housing, and a pause valve assembly positioned between the fluid inlet and the fluid outlet and capable of interrupting fluid flow through the handle. Fluid can flow into the housing through a hose and out of the housing through an attached tip. The pause valve assembly can include a shuttle valve, which is received in a valve housing, and a pause actuator. In one embodiment, the shuttle valve is coupled to the pause actuator by a retaining ring and selective movement of the actuator is translated to the shuttle valve.

In some embodiments, the shuttle valve can be positioned to restrict the flow of fluid through the pause valve assembly when the pause mode is selected with the pause actuator. The shuttle valve does not block fluid flow through the handle when the irrigate mode is selected with the pause actuator.

One embodiment includes a handle with a pause switch assembly connected to the handle. The pause switch assembly includes an actuator slidably connected to the handle and movable between a first position and a second position, and a shuttle valve operably connected to the actuator and positioned between the handle inlet and the handle outlet. During operation of the pause switch, movement of the actuator from the first position to the second position slides the shuttle valve from an irrigate position to a paused position and, in the paused position, the shuttle valve prevents fluid entering an inlet of the handle from reaching an outlet of the handle.

Another embodiment of the present disclosure includes a handle for an irrigating device. The handle includes a housing in fluid communication with a fluid source. The housing may have a housing inlet and a housing outlet, a tip removably connected to the housing and in fluid communication with the housing inlet, and a pause control connected to the housing and configured to selectively interrupt fluid flow from the handle outlet to the handle inlet. The pause control includes a switch movable along a longitudinal axis of the housing between a first position and a second position and a shuttle valve connected to the switch. Movement of the switch from the first position to the second position slides the shuttle valve from an open position to a closed position. In the open position the fluid flows uninterrupted from the handle inlet to the tip and in the closed position the fluid flow is blocked between the handle inlet and the tip.

In another embodiment of the present disclosure, a handle for an oral irrigator includes a swivel assembly received within the housing and fluidically coupled to the tip, and a hose connected to and fluidically coupled to the swivel assembly. The swivel assembly minimizes or prevents translation of rotational movement of the handle or the hose relative to the other.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. A more extensive presentation of features, details, utilities, and advantages of the present invention as defined in the claims is provided in the following written description of various embodiments of the invention and illustrated in the accompanying drawings.

BRIEF DESCRIPTION OF THE DRAWINGS

FIG. 20A is a rear isometric view of a first shell of the handle of FIG. 18.

DETAILED DESCRIPTION

An oral irrigator handle through which fluid flow can be interrupted is disclosed herein. In irrigate mode, fluid flows from a hose into valve components within the handle housing, and out a fluidically connected tip. Fluid flow is interrupted in a pause mode by a mechanically controlled flow restriction valve that is safe and convenient for the user. Fluid flow may be controlled by a pause valve assembly. In one exemplary embodiment, manually operating a pause actuator of a pause valve assembly slides a shuttle valve, via a coupled retaining ring, to a position atop a poppet support assembly that blocks fluid flow through the handle.

An oral irrigator handle having a swivel assembly is also disclosed herein. The swivel assembly is positioned within the handle housing and allows the hose to rotate 360 degrees relative to the handle, such that as a user moves the handle in various directions and/or rotates the handle, the handle can spin with respect to the hose, reducing the chance that the hose will get tangled, bent, or pinched.

Components of the Oral Irrigator

Figure 1:
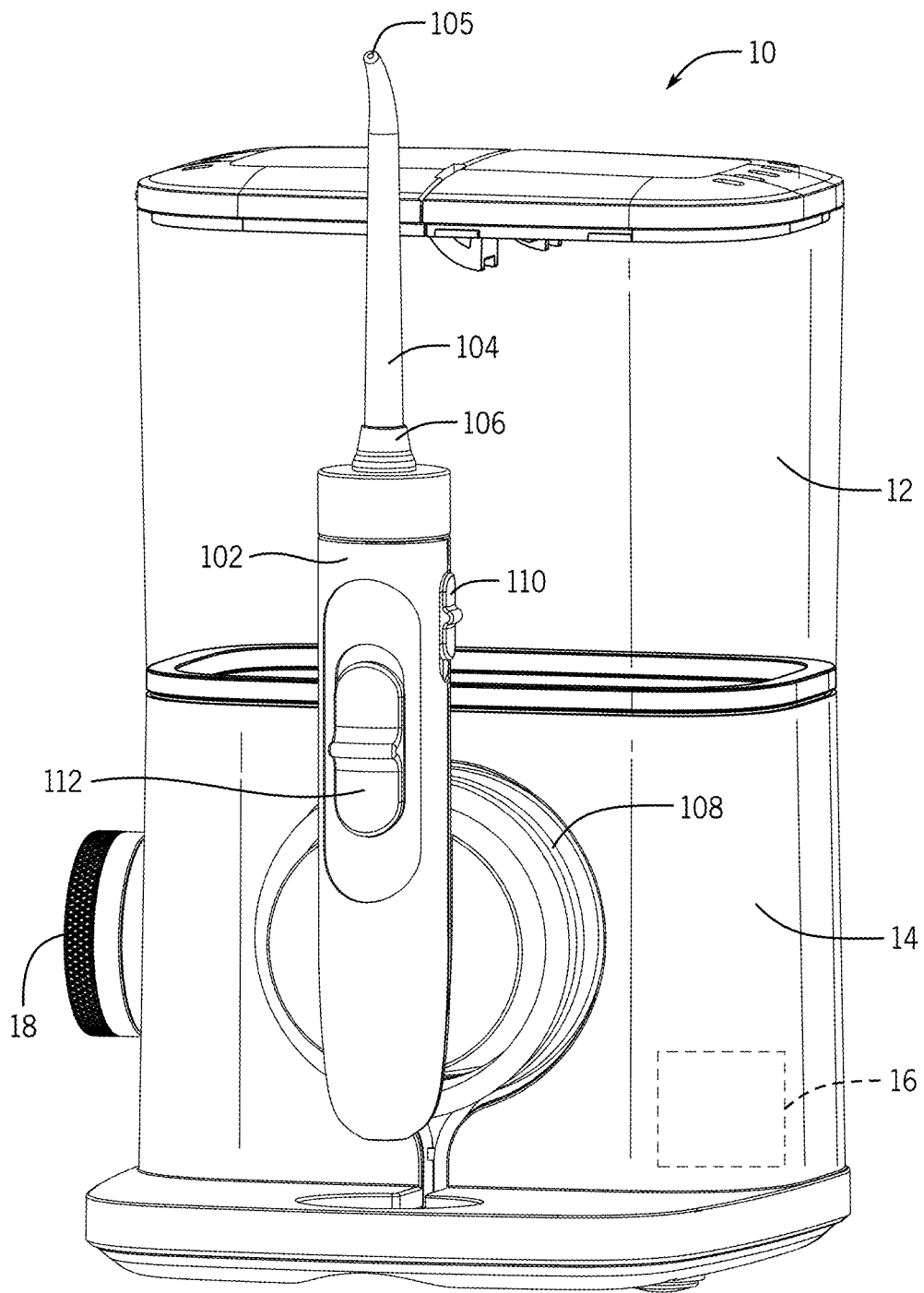
FIG. 1 is a front right isometric view of an oral irrigator, including a handle, in pause mode, for an oral irrigator connected to a hose connectable to a base unit.
Figure 2A:
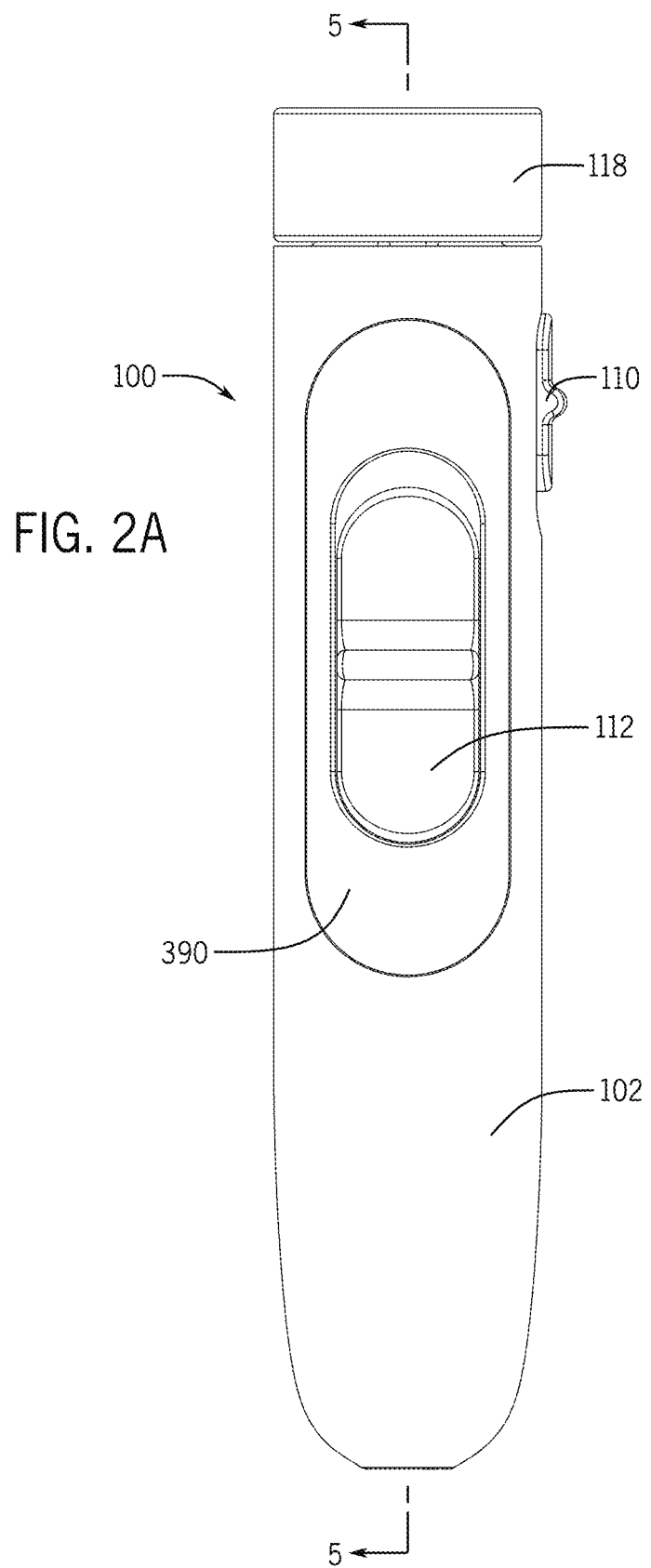
FIG. 2A is a front elevation view of the handle of FIG. 1.
Figure 2B:
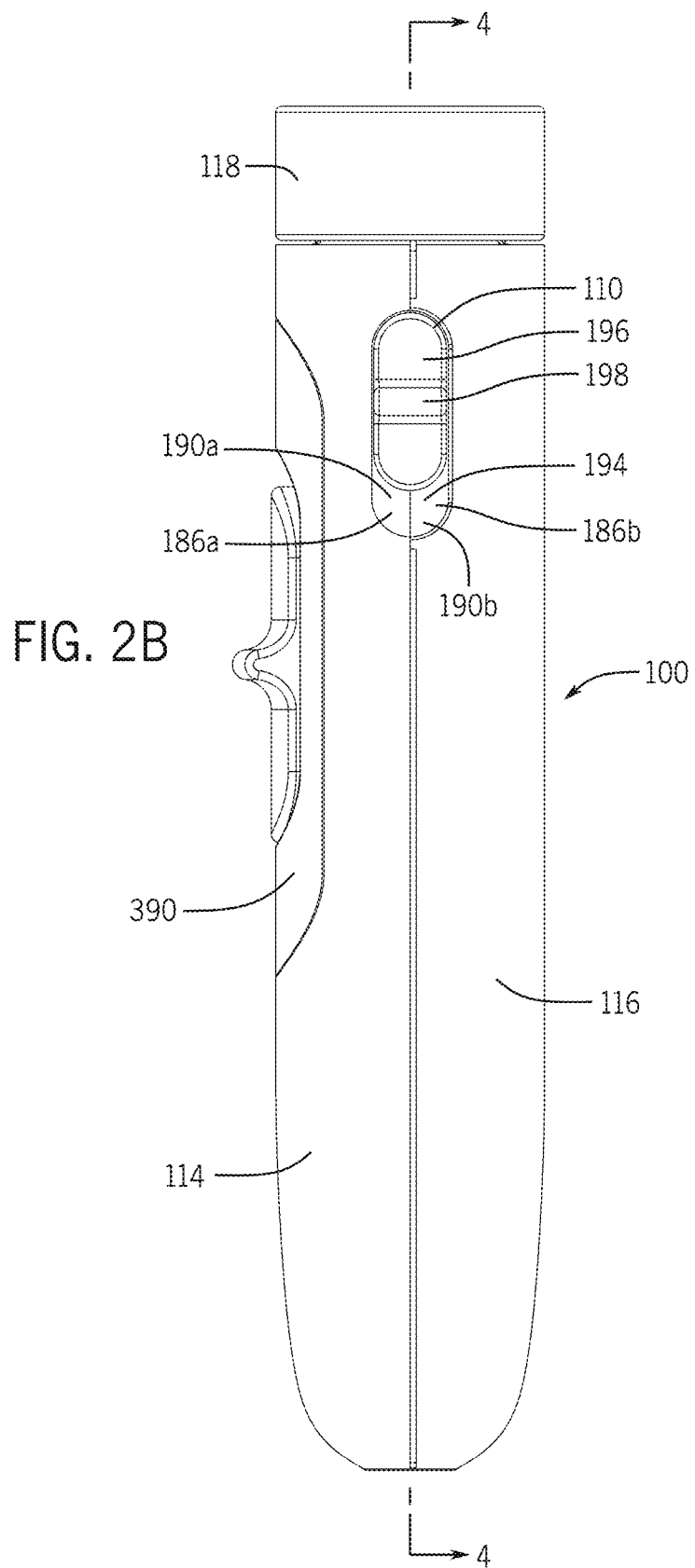
FIG. 2B is a right elevation view of the handle of FIG. 1.
Figure 3:
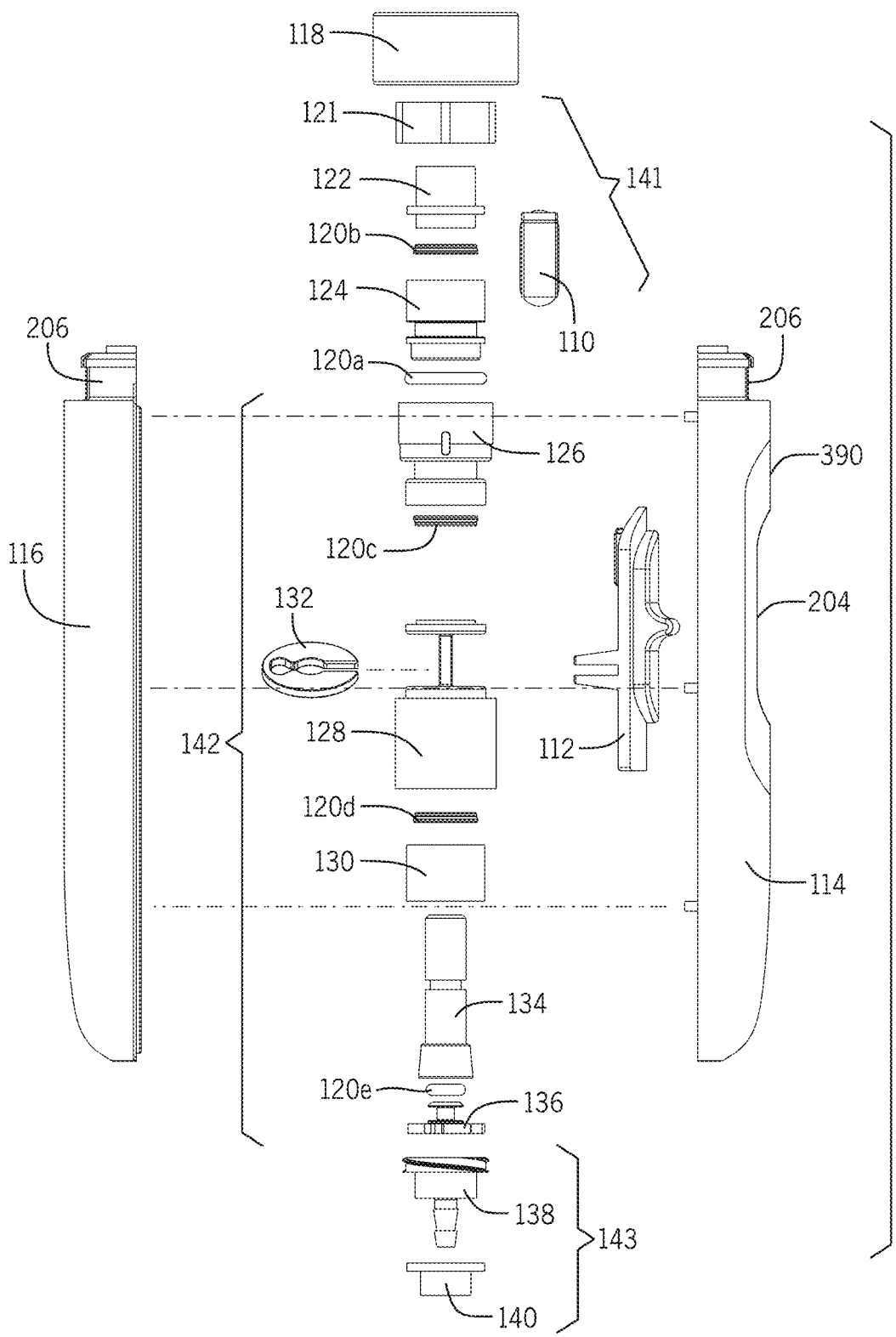
FIG. 3 is an exploded view of the handle of FIG. 1.

Turning to the figures, an oral irrigator will now be discussed in more detail. FIG. 1 illustrates an isometric view of an oral irrigator including a handle with each of a pause valve assembly and a swivel assembly. FIGS. 2A and 2B are elevation views of the handle of FIG. 1.

With reference to FIG. 1, the oral irrigator 10 may include a handle 100, a reservoir 12, a base 14, and a hose 108, all of which may be interconnected together. The base 14 may include a pump 16 fluidically connected to the reservoir 12 that pumps fluid from the reservoir 12 to a tip 104. A control 18 is coupled to the base 14 and configured to vary a flow rate or a fluid pressure produced by the pump 16, and/or may activate a particular mode, e.g., a cleaning mode, produced by the pump 16. The base 14 and pump 16 may be similar to the base and pump illustrated in U.S. Publication No. 2015/0004559 entitled "Oral Irrigator with Integrated Lid and Base," filed on Mar. 13, 2014, which is incorporated herein by reference in its entirety. In other embodiments, the handle may enclose the pump and other components and connect directly to the reservoir. In these embodiments, the handle may form a main housing for the device.

The Handle

With reference to FIGS. 1-2B, the handle 100 is fluidically connected to the pump 16 and a fluid source, such as the reservoir 12, by the hose 108. The handle 100 may generally include a housing 102, a handle collar 118, a tip 104, a tip eject mechanism 141, a backflow valve body 124, a pause valve assembly 142, and a swivel assembly 143, each of which are discussed in turn below.

As noted, the hose 108 fluidically connects the handle 100 to the reservoir 12. However, in instances where the irrigator is a handheld unit, the hose 108 may be omitted or may be varied as the reservoir 12 may be directly connected to the handles as shown in U.S. Publication No. 2008/0008979, entitled "Oral Irrigator," filed on Jul. 7, 2006 and incorporated by reference herein in its entirety.

The handle 100 is also fluidically connected to a removable tip 104, which is configured to be inserted into a user's mouth and to expel fluid against a user's teeth, gums, tongue, etc. The tip 104 may be inserted into the handle 100 through a handle collar 118. A tip eject button 110 can selectively release the tip 104 from the handle 100. Liquid from the fluid source can be expelled through a tip outlet 105 in the tip 104 when the tip 104 is connected to the handle 100. In some examples, the tip outlet 105 portion of the tip 104 may be shaped as a nozzle or may include a nozzle or other attachment connected thereto.

As described in more detail below, the handle 100 may include a pause actuator 112. The pause actuator 112 can selectively interrupt the flow of liquid from the fluid source to the tip 104.

With reference to FIGS. 2A-5B, an exemplary embodiment of the handle housing 102 will now be discussed in more detail. The handle housing 102 may be an integrated component or, as shown in FIGS. 2A-5A, may include a first shell 114 and a second shell 116 coupled together (e.g., through ultrasonic welding, fasteners, adhesive, or the like). Each of the first and second shells 114, 116 may be constructed of a rigid material that resists deformation, such as a hard plastic, but it should be noted that various other materials may be used as well. Additionally, the handle housing 102 may include an aesthetically pleasing shape that may conform to a user's hand and may include one or more gripping elements.

Figure 4:
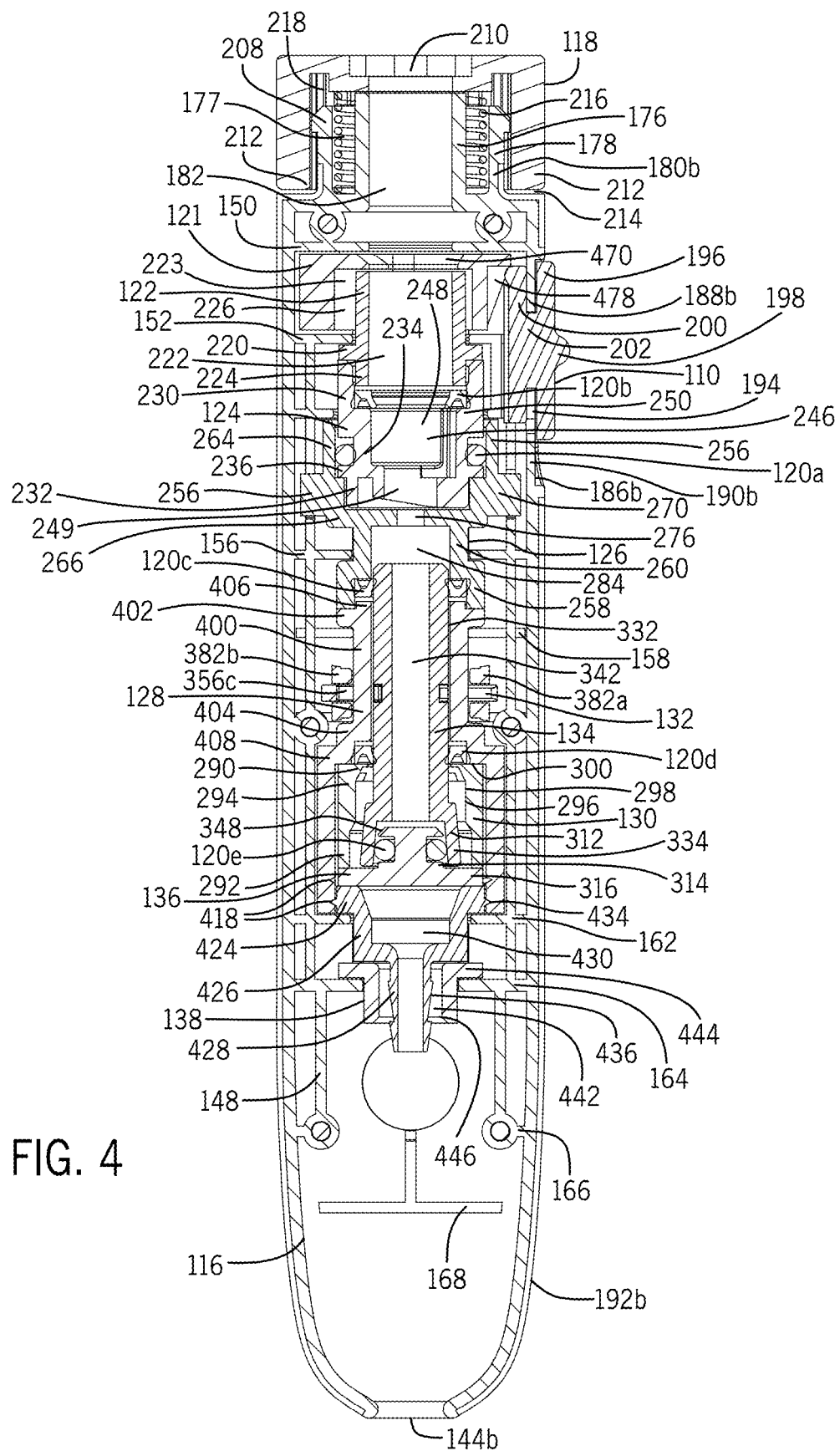
FIG. 4 is an elevation view in cross section of one embodiment of the handle of FIG. 1 along line 4-4 in FIG. 1.
Figure 5A:
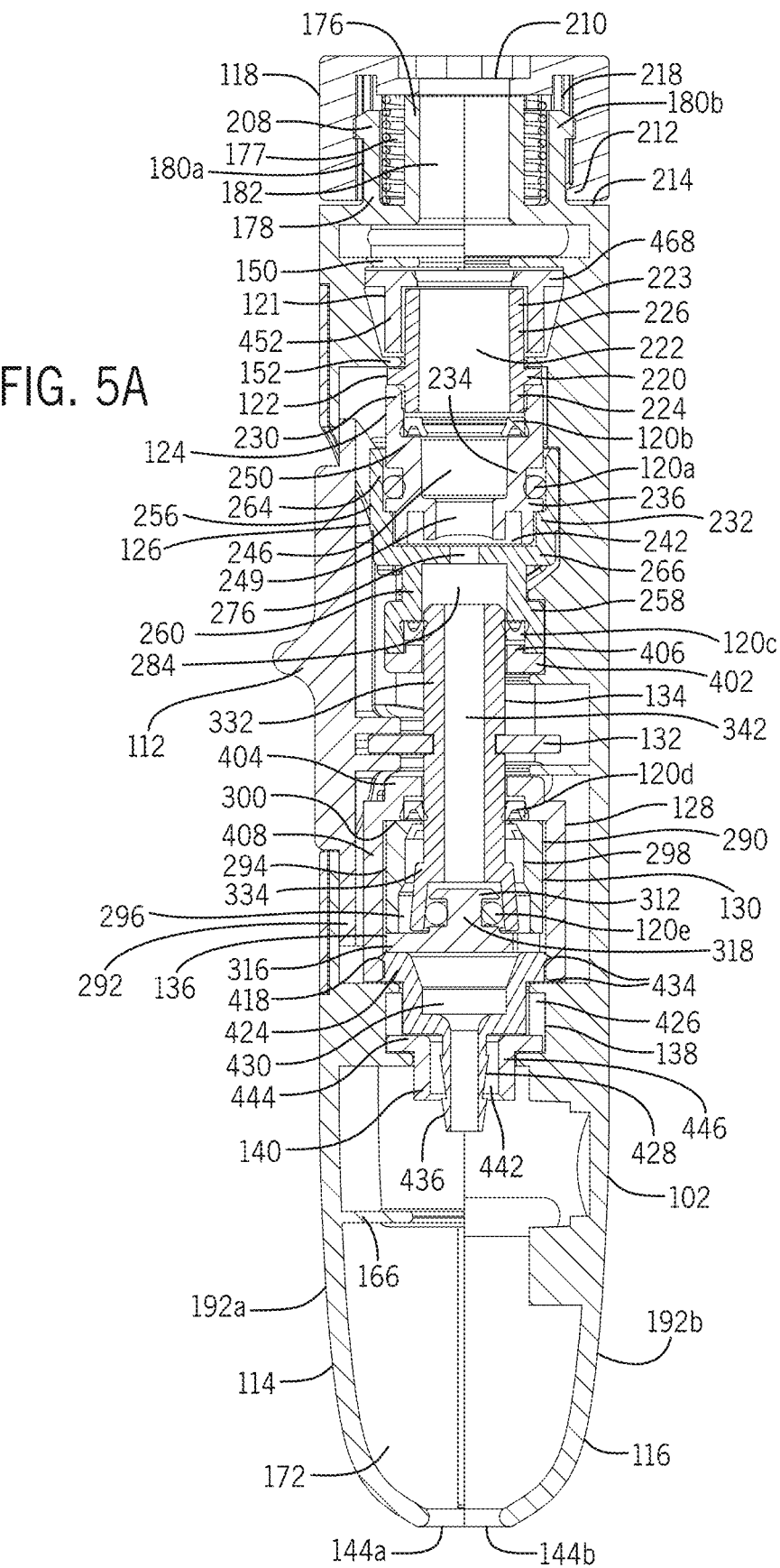
FIG. 5A is an elevation view in cross section of the handle of FIG. 1 along line 5-5 in FIG. 1.
Figure 5B:
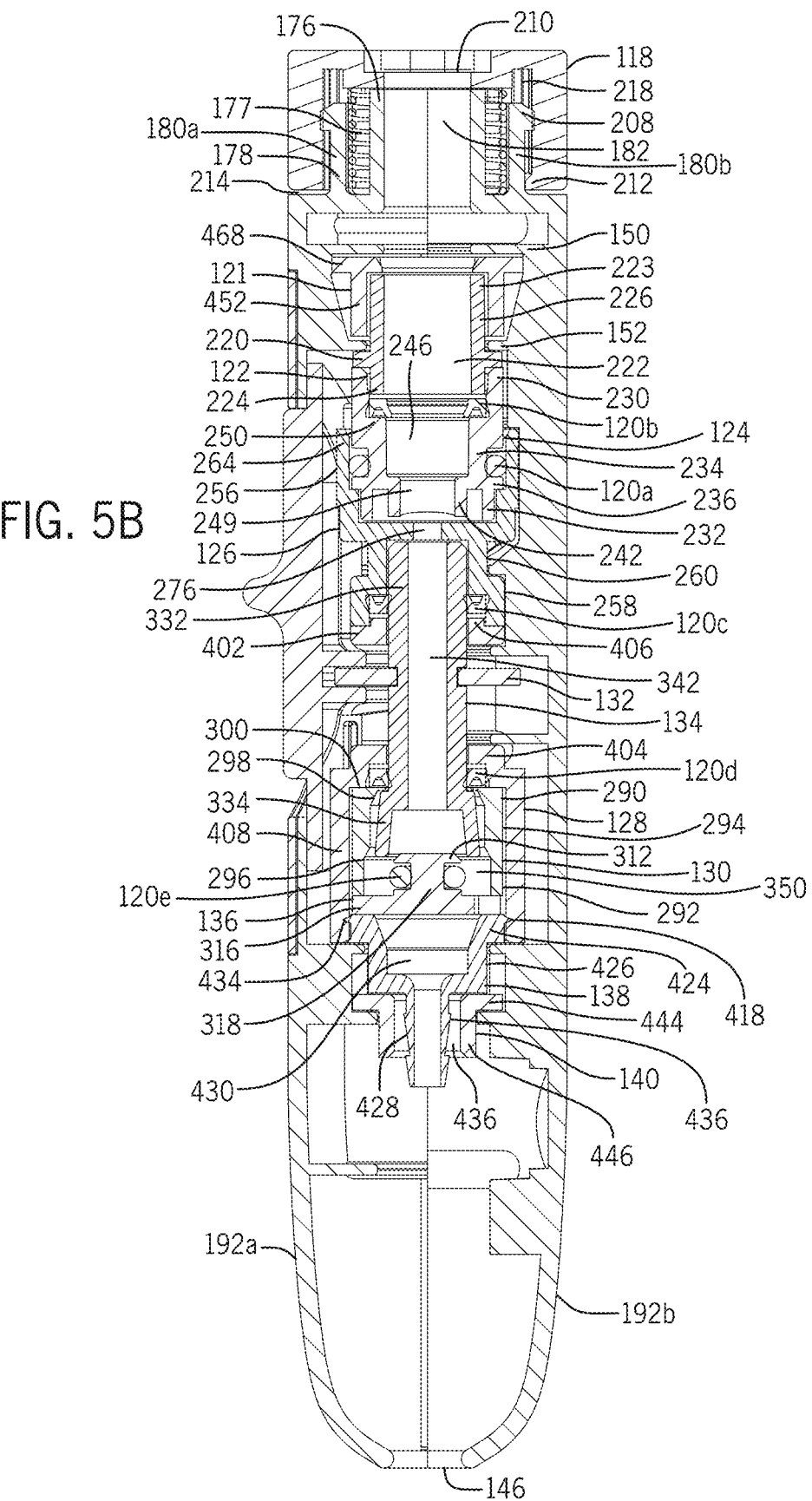
FIG. 5B is an elevation view in cross section of the handle of FIG. 1 along line 5-5 in FIG. 1, in irrigate mode.
Figure 6A:
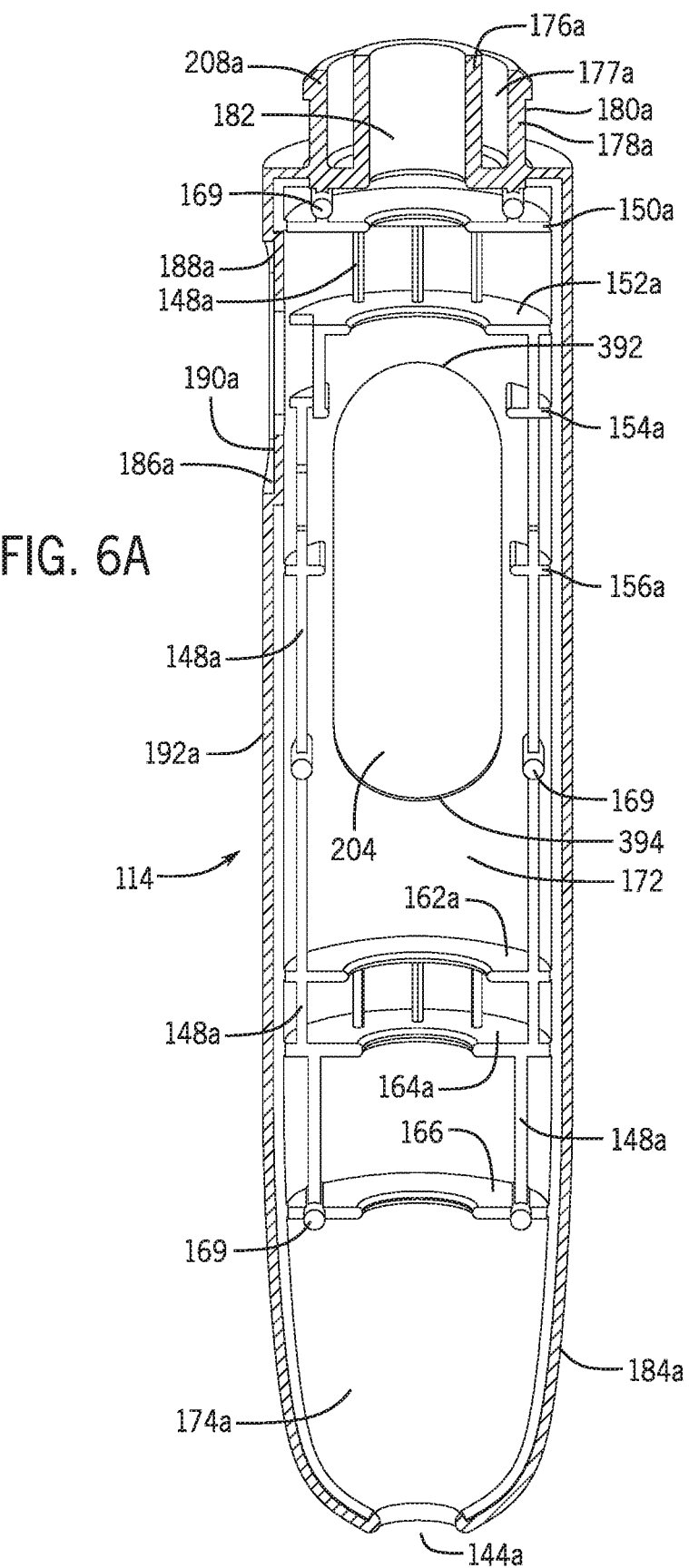
FIG. 6A is a rear isometric view of a first shell of the handle of FIG. 4.
Figure 6B:
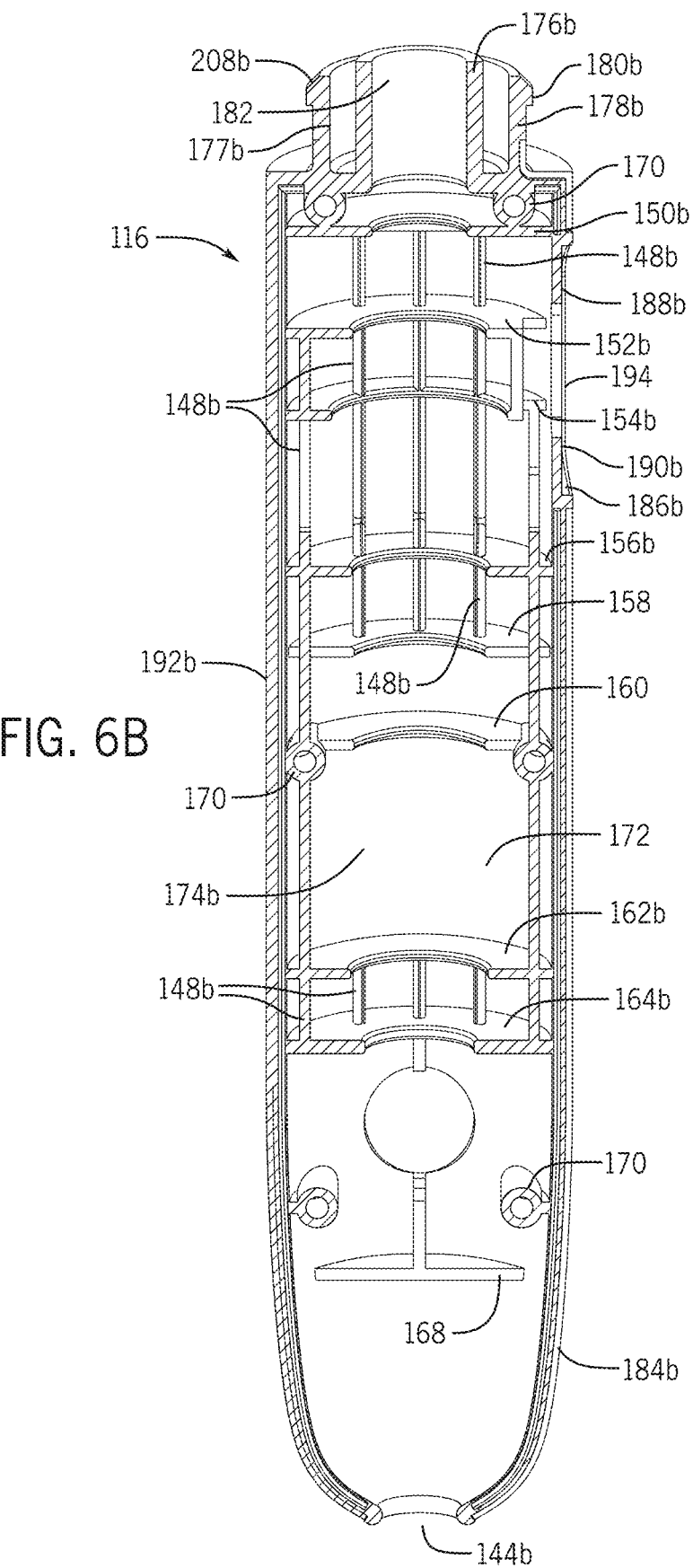
FIG. 6B is a front isometric view of a second shell of the handle of FIG. 4.

As shown in FIGS. 3-6B, each of the first and second shells 114, 116 may be comprised of a neck 180a, 180b and shell body 192a, 192b. With reference to FIGS. 6A and 6B, the bodies 192a, 192b of the first and second shells 114, 116, respectively, together define a handle cavity 172 in which components of the handle 100, such as the tip eject mechanism 141, pause valve assembly 142, swivel assembly 143, and a portion of the hose 108, may reside. The first shell 114 may include first, second, third, fourth, seventh, eighth, and ninth ledges 150a, 152a, 154a, 156a, 162a, 164a, and 166, respectively, for aligning, receiving, retaining, and/or supporting the tip eject mechanism 141, valve assembly 142, swivel assembly 143, hose 108, or other components of the handle 100 within the handle cavity 172 (see FIGS. 5A and 5B). The ledges 150a, 152a, 154a, 156a, 162a, 164a, and 166 generally extend in a horizontal plane with respect to a longitudinal axis of the handle 100, and radially inwardly from an interior wall 174a of the first shell 114 within the handle cavity 172.

The second shell 116 may include first, second, third, fourth, fifth, sixth, seventh, eighth, and tenth ledges 150b, 152b, 154b, 156b, 158, 160, 162b, 164b, and 168, respectively, for aligning, receiving, retaining, and/or supporting the tip eject mechanism 141, valve assembly 142, swivel assembly 143, hose 108, or other components of the handle 100 within the handle cavity 172 (see FIGS. 4, 5A, and 5B). As in the first shell 114, the ledges 150b, 152b, 154b, 156b, 158, 160, 162b, 164b, and 168 of the second shell 116 generally extend in a horizontal plane with respect to the longitudinal axis of the handle 100, and radially inwardly from an interior wall 174b of the second shell 116 within the handle cavity 172.

Some ledges 150a, 152a, 154a, 156a, 162a, 164a of the first shell 114 may align with a mating ledge 150b, 152b, 154b, 156b, 162b, 164b, respectively, of the second shell 116 when the handle 100 is assembled.

The depth of the ledges 150a, 150b, 152a, 152b, 154a, 154b, 156a, 156b, 158, 160, 162a, 162b, 164a, 164b, 166, and 168 may be the same or different, and the depth of a given shelf may vary along the width (the lateral dimension) of that shelf. Some of the ledges 150a, 150b, 152a, 152b, 154b, 156b, 158, 160, 162a, 162b, 164a, 164b, and 166 may be shaped as arcs. When the first shell 114 and second shell 116 are assembled to form the housing 102, mating ledges 150a, 150b, 152a, 152b, 162a, 162b, 164a, 164b may align to form generally circular apertures for receiving portions of components such as the pause valve assembly 142.

The bodies 192a, 192b of the first and second shells 114, 116 may also include a plurality of vertical support walls 148a, 148b for supporting the ledges 150a, 150b, 152a, 152b, 154a, 154b, 156a, 156b, 158, 160, 162a, 162b, 164a, 164b, 166, and 168. The vertical support walls 148a, 148b may also help to align, receive, retain, and/or support the tip eject mechanism 141, the valve assembly 142, the swivel assembly 143, the hose 108, or other components of the handle 100 within the handle cavity 172. The vertical support walls 148a, 148b may be as deep as the ledges 150a, 150b, 152a, 152b, 154a, 154b, 156a, 156b, 158, 160, 162a, 162b, 164a, 164b, 166, and 168 they abut, or may be less deep.

With further reference to FIGS. 6A and 6B, one or more pegs 169 may extend from the interior wall 174 of one of the shells 114, 116 (e.g., in the depicted embodiment, the first shell 114) proximate the first and ninth ledges 152a, 166, respectively, and between the fourth and seventh ledges 156a, 162a, respectively, adjacent a vertical support wall 148a. Each peg 169 may extend into the handle cavity 172 beyond a plane defined by a circumferential edge of the exterior wall 184b of the second shell 116. Each peg 169 may be adapted to mate with a corresponding boss defining holes 170 proximate the first, sixth, and tenth ledges 150b, 160, and 168, respectively, of the opposing shell 114,116 (e.g., in the depicted embodiment, the second shell 116). The pegs 169 and the holes 170 may be dimensioned such that each peg 169 will relatively snugly fit within its corresponding hole 170. The friction resulting from this fit may resist decoupling of the shells 114, 116. Alternatively and/or additionally, the first and second shells 114, 116 may be joined using glue, epoxy, fasteners, sonic welding, any other known method for joining two items, or by a combination of known methods.

As depicted in FIGS. 2B, 4, 6A, and 6B, the outer surface of the exterior walls 184a, 184b of the first and second shells 114, 116 may each define a C-shaped depression 186a, 186b with respective upper surfaces 188a, 188b and lower surfaces 190a, 190b. When the handle housing 102 is assembled, opposing depressions 186a, 186b define a pocket 186 surrounding an opening 194.

With reference again to FIG. 6A, the first shell 114 may also include a pause actuator aperture 204 for receiving a pause actuator 112 and a recessed pause actuator frame 390. The pause actuator aperture 204 may have an upper portion 392 and a lower portion 394. In the depicted embodiment, both the pause actuator aperture 204 and the pause actuator frame 390 are oval-shaped, but may be any shape. By placing the pause actuator 112 on the handle 100, the user may more easily change settings or pause the fluid flow while using an oral irrigator that is fluidically connected to the handle 100.

With reference to FIGS. 4-6B, the body 192a, 192b of each of the first and second shell 114, 116 may terminate in a semicircular hose cut-out 144a, 144b. When the first and second shells 114, 116 are assembled to form the housing 102, the cut-outs 144a, 144b together define a substantially circular aperture 146 through which the hose 108 passes.

With reference to FIGS. 3-6B, the neck 180a, 180b of each of the first and second shell 114, 116, respectively, includes an interior wall 176a, 176b and an exterior wall 178a, 178b. The interior and exterior walls 176a, 176b, 178a, 178b may be generally semicylindrical in shape such that when the first and second shells 114, 116 are assembled to form the housing 102, the interior and exterior walls 176a, 176b, 178a, 178b form generally concentric cylinders with an annular recess 177a, 177b defined therebetween for receiving a spring 216. The exterior walls 178a, 178b may be continuous or may have one or more interruptions or gaps 206 near the midpoint of the width of each of the first and second shell 114, 116. The exterior walls 178a, 178b may include a lip 208a, 208b and the interior walls 176a, 176b may extend beyond the plane of the lips 208a, 208b. When the first and second shells 114, 116 are assembled, the interior walls 176a, 176b define a cylindrical tip cavity 182 configured to receive a tip 104.

The handle 100 may include a generally circular handle collar 118. The interior surface may be ribbed and may define a tip-receiving aperture 210 for receiving the tip 104. The diameter of the internal surface may be the same as the internal diameter of the interior walls of the neck 180a, 180b. The spring 216 may be positioned in or under the handle collar 118, such as by being inserted into an annular well 218 defined in the handle collar 118 or molded into the handle collar 118 (see FIG. 4).

Tip Eject Mechanism

With reference to FIGS. 3-5B, 7A, and 7B, the tip eject mechanism 141 of the handle 100 will now be discussed in more detail. The tip eject mechanism 141 aids in the insertion and removal of a tip 104. The tip eject mechanism 141 is substantially similar to the tip eject mechanism described in U.S. patent application Ser. No. 14/555,339, which is incorporated by reference in its entirety herein. The tip eject mechanism 141 or tip release assembly comprises a cylindrical valve cap 122, a latch 121, and a tip eject button 110.

The tip eject button 110 is configured to mechanically initiate the release of a tip 104 from the handle 100, such as by sliding the button 110 upward toward the tip outlet 105. The tip eject button 110 may be formed with an exterior slider portion 196 and an interior slider portion 200 that are separated from each other by a neck 202. The exterior slider portion 196 may be substantially obround in shape and may include a tab grip 198, which may help a user's fingers or hand to more easily operate the tip eject button 110 and prevent the user's finger or hand from slipping off the tip eject button 110. An upper end of the interior slider portion 200 may include a nose 201 that projects radially inward therefrom. The exterior slider portion 196 may be approximately the same length as the interior slider portion 200, as in the embodiment depicted in FIGS. 7A and 7B, or may be shorter than or longer than the interior slider portion 200. The lateral and longitudinal dimensions of the neck 202 are smaller than the related dimensions of the exterior and interior slider portions 196, 200 such that a circumferential channel is formed between the exterior and interior slider portions 196, 200 about the neck 202.

The valve cap 122 may receive at least a portion of a tip 104 and help provide a secure connection between the tip and the handle 100. The valve cap 122 may include a body 226 having an upper end 223 and a lower end 224, and a circumferential rim 220 near the lower end 224. The interior of the valve cap 122 may define a tip cavity 222 for receiving a tip 104.

The latch 121 is configured to releasably engage a tip 104 to both secure it to the handle 100 and aid in removing the tip 104 from the handle 100. The latch 121 may comprise a latch body 452 to which spring legs 454 are attached via a neck 456. The spring legs 454 extend laterally apart from each other on opposing sides of the neck 456 along a side of the latch body 452 opposite the tip eject button 110. The neck 456 separates the spring legs 454 from the latch body 452 such that a gap 458 is formed between each of the spring legs 454 and the latch body 452. In the exemplary embodiment shown, the outer wall 460 of the latch body 452 opposite each of the spring legs 454 is curved such that the gaps 458 widen toward their open ends away from the neck 456. Each spring leg 454 may terminate in a foot 462. The outer surface of each foot 462 may have a bulbous projection 464 outward along the width. Each spring leg 454 may be flexible, deformable, and/or resilient such that it returns to its original shape and configuration after being compressed.

Figure 7A:
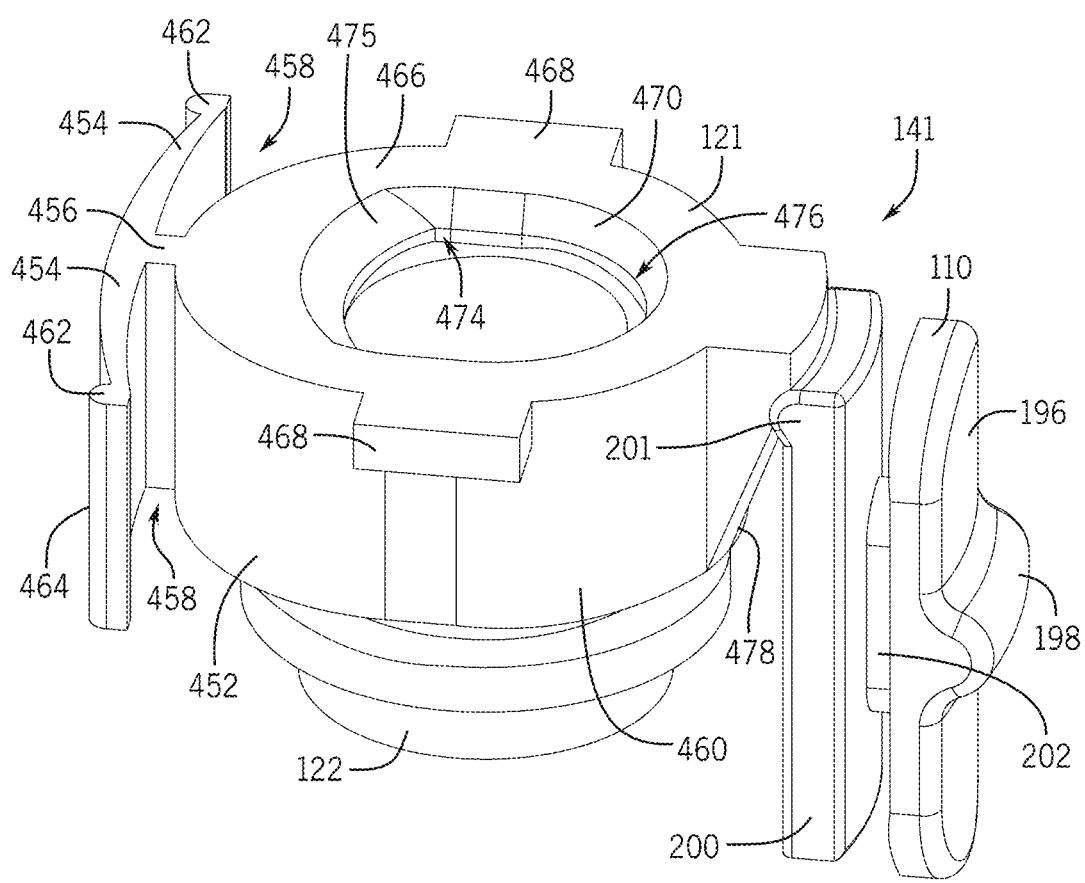
FIG. 7A is a front isometric view of a tip eject mechanism of the handle of FIG. 4.
Figure 7B:
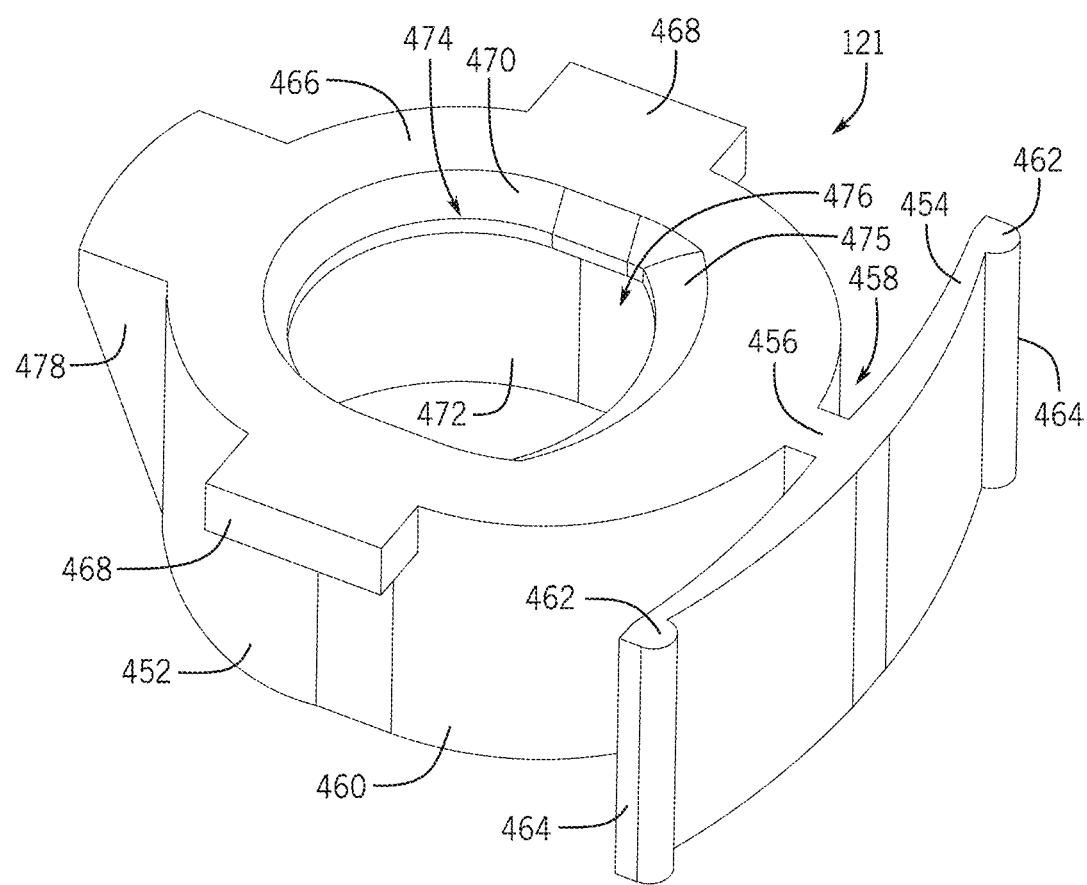
FIG. 7B is a rear top isometric view of a latch of the tip eject mechanism of FIG. 7A.
Figure 8A:
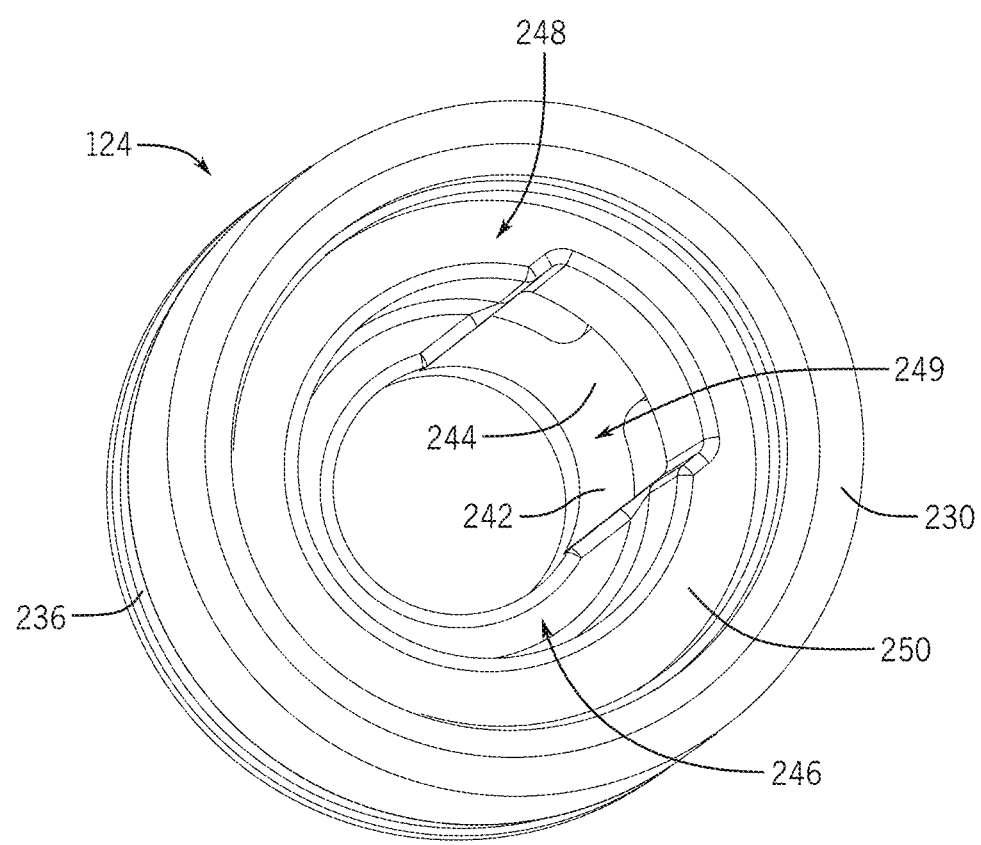
FIG. 8A is a front top isometric view of a backflow valve housing of the handle of FIG. 4.
Figure 8B:
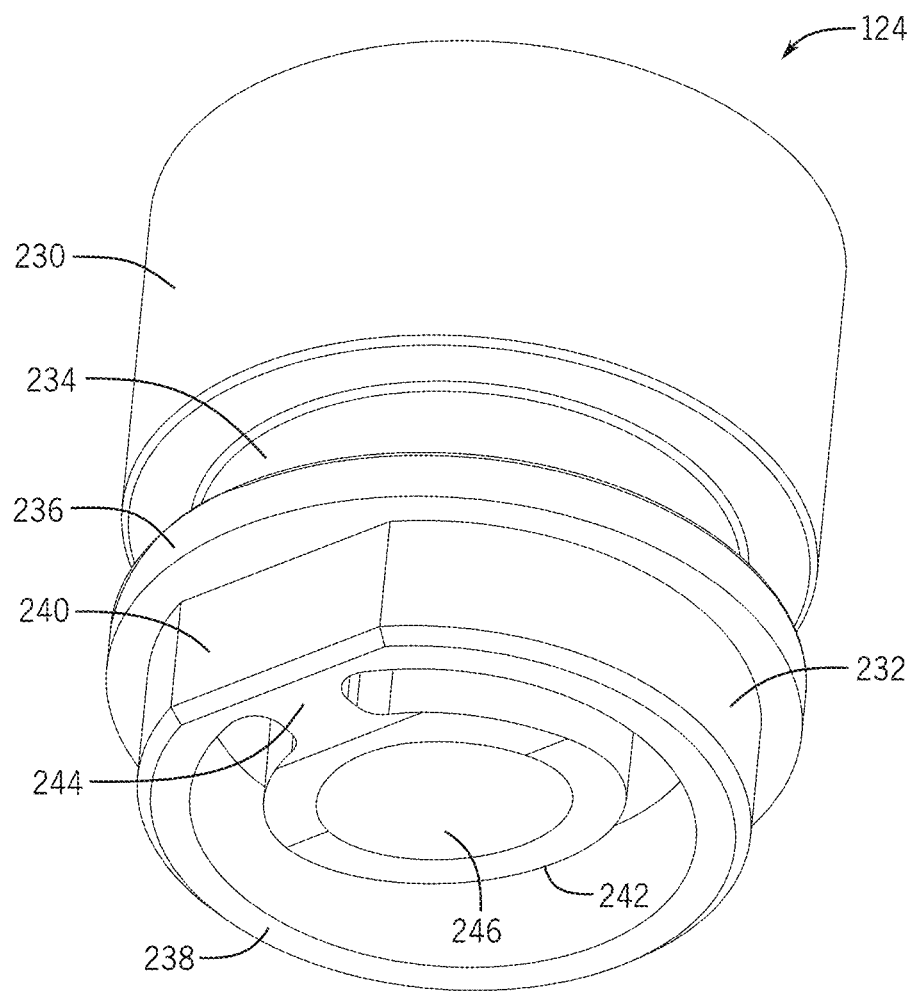
FIG. 8B is a rear bottom left isometric view of the backflow valve housing of FIG. 8A.

As depicted in FIGS. 7A and 7B, a top surface 466 of the latch body 452 comprises ledges 468 that are laterally opposed to each other and which extend radially outward and partially around the perimeter of the latch body 452 on the sides between the spring legs 454 and the tip eject button 110. The ledges 468 extend laterally away from the latch body 452 and have a width sufficient to interface with flat surfaces of the housing 100 and thereby prevent rotation of the latch body 452.

The latch body 452 also comprises an interior lip 470 that extends generally radially inward above an interior wall 472. The interior lip 470 may be chamfered, as depicted in FIGS. 7A and 7B, or may be smooth and may define a tip-receiving aperture 474 for receiving the tip 104. The perimeter defined by the interior lip 470 may be an irregular oval or bell shape, as depicted in FIGS. 7A and 7B, or may be any other shape. The shape of the perimeter may be complementary to the tip 104 that is received in the tip-receiving aperture 474. A locking edge 475 of the interior lip 470 may be positioned adjacent to the spring legs 454. The locking edge 475 may extend radially outward beyond the surface of the interior wall 472 in order to engage a corresponding groove formed within a tip 104 and thereby retain the tip 104 within the latch body 452.

The interior walls 472 of the latch body 452 may define a valve cap cavity 476, which is configured to receive the upper end 223 of the body 226 of the valve cap 122. A cross-sectional area of the valve cap cavity 476 may thus be greater than a cross-sectional area of the tip-receiving aperture 474. The valve cap cavity 476 may be substantially obround in shape and thus oblong as compared to the circular shape of the body 226 of the valve cap 122.

The latch body 452 also includes a chamfered wall 478 on the outside sidewall opposite the neck 456 and spring legs 454. The chamfered wall 478 may include an opening between two chamfered legs or it may be solid.

Backflow Valve

With reference to FIGS. 3-5B, 8A, and 8B, the handle 100 may include a backflow valve body 124 for enclosing or supporting a reed valve (not shown). The backflow valve body 124 may include a generally cylindrical top end 230 and a bottom end 232 separated by a generally cylindrical neck 234 and an annular rim 236. The external diameter of the top end 230 may be approximately the same as the external diameter of the rim 236, and both diameters may be greater than the external diameter of the bottom end 238, which in turn may be greater than the external diameter of the neck 234. A sealing member 120a, such as an O-ring, may be received in the neck 234.

The interior of the backflow valve body 124 may define a valve cavity 246 having an upper portion 248 and a lower portion 249. A sealing member 120b, such as a U-cup, may be received in an upper portion 248 of the valve cavity 246 above and adjacent to a ledge 250 positioned about midway along the height of the top end 230 of the backflow valve body 124.

The bottom end 232 of the backflow valve body 124 includes a bottom edge 238 that includes a keyed feature 240. The bottom edge 238 also includes a flap support 242 for supporting or securing an optional reed valve (not shown). The flap support 242 may be formed as a generally circular ring having a diameter narrower than the upper portion 248 of the valve cavity 246 and may be connected to the bottom edge 238 via a bridge 244. The flap support 242 may be angled such that only a portion, for example the portion adjacent to the bridge 244, is in the same plane as the bottom edge 238 of the bottom end 232 of the backflow valve body 124 and the remainder of the flap support 242 is angled inward and upward toward the valve cavity 246 such that it does not reach the plane of the bottom edge 238.

Pause Valve Assembly

Figure 9A:
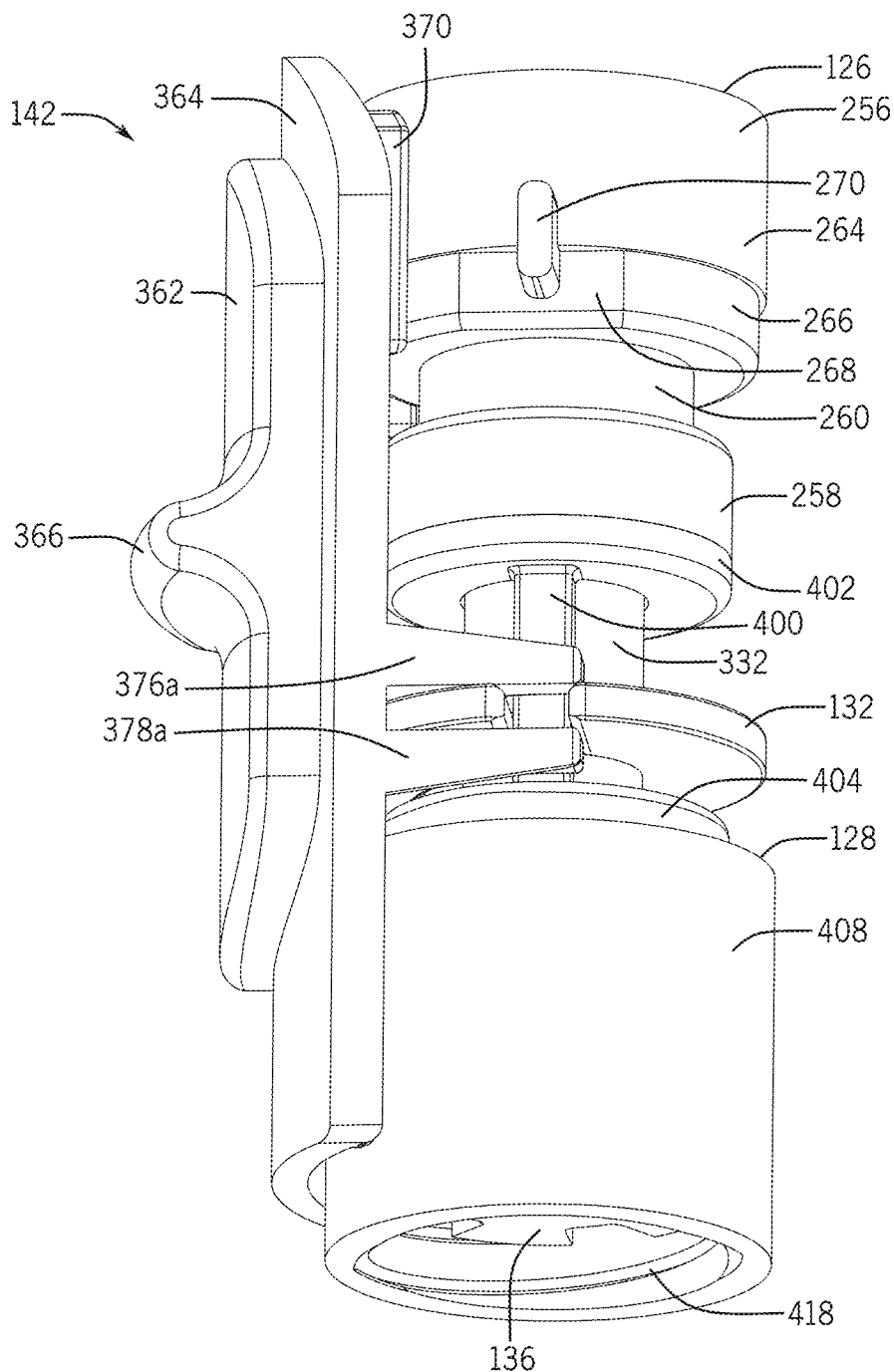
FIG. 9A is a right isometric view of a pause valve assembly of the handle of FIG. 4.
Figure 9B:
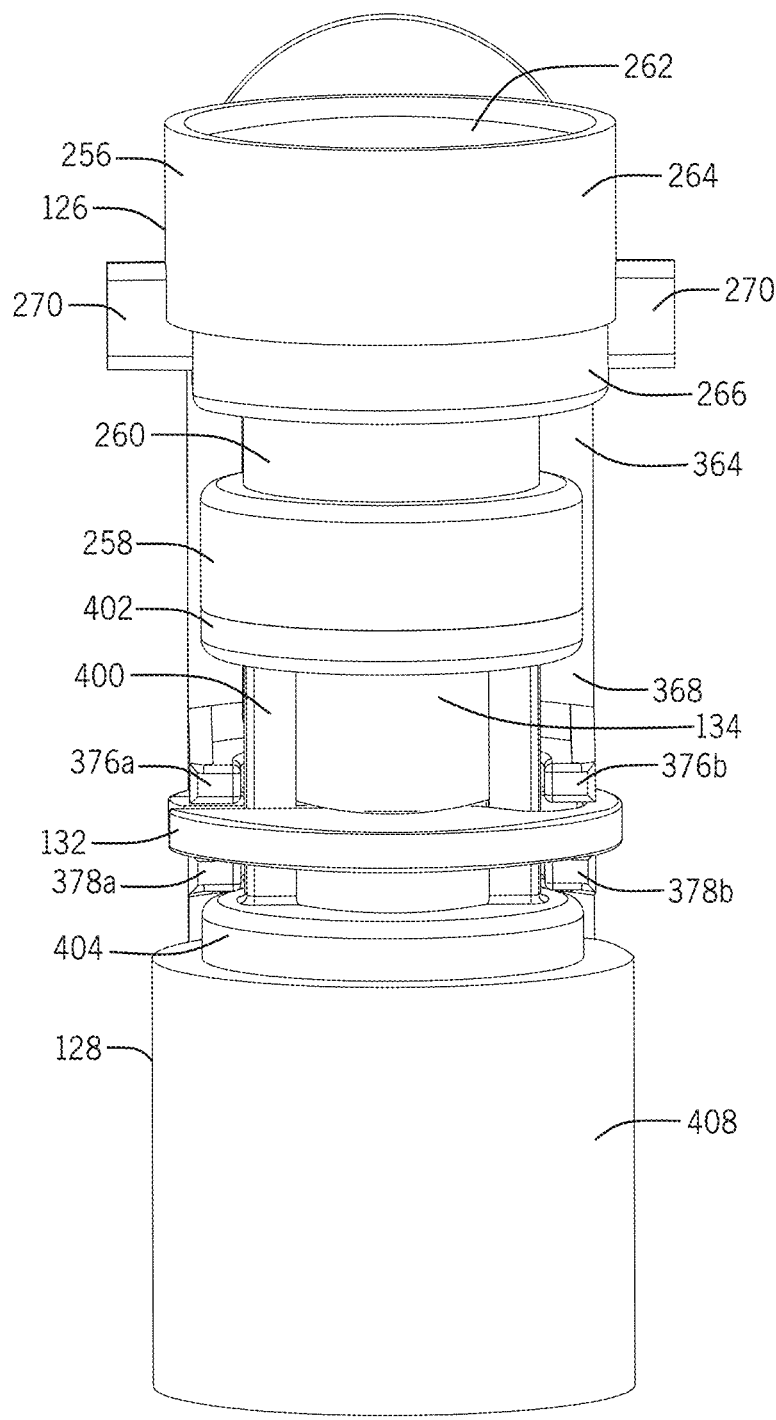
FIG. 9B is a rear isometric view of the pause valve assembly of FIG. 9A.

With reference to FIGS. 9A and 9B, the pause valve assembly 142 will now be discussed in more detail. The pause valve assembly 142 allows a user to interrupt fluid flow to the tip 104 without removing his or her hand from the handle 100 and without turning off power to the oral irrigator 10. The pause valve assembly 142 may include an upper valve body 126, a lower valve body 128, a shuttle valve 134 received within the upper and lower valve bodies 126, 128, a shuttle retainer 130 and a poppet assembly 136 (e.g., a valve seal or sealing assembly), both received within the lower valve body 128, and a pause actuator 112 operably connected to the shuttle valve 134 by a retaining ring 132 such that selective movement of the actuator 112 also moves the shuttle valve 134 within the upper and lower valve bodies 126, 128. The various components of the pause valve assembly 142 will now be discussed in more detail.

With reference to FIGS. 3-5B, 9A, 9B, and 11A-C, the upper valve body 126 fluidically connects the chamber 124 and the lower valve body 128. The upper valve body 126 may include a head 256 and a base 258 connected by a neck 260. Each of the head 256, base 258, and neck 260 may be generally cylindrical and define a valve cavity 262 therethrough. The head 256 may include an upper portion 264 and a lower portion 266, and the lower portion 266 may define a chord segment 268 that interrupts the outer cylindrical surface of the lower portion 266. The external diameter of the upper portion 264 may be slightly greater than the external diameter of the lower portion 266. The external diameters of the both the upper and lower portions 264, 266 of the head 256 may be generally greater than the external diameter of the base 258, which in turn may be greater than the external diameter of the neck 260.

Figure 11A:
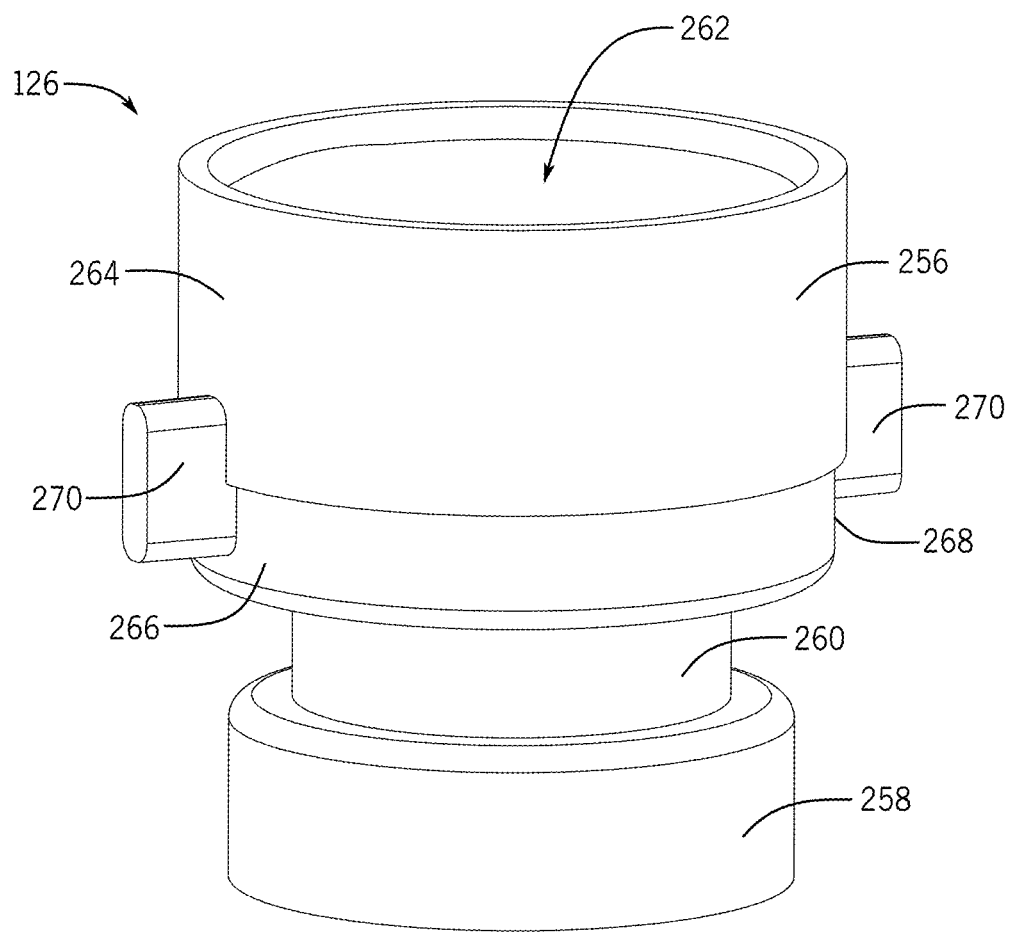
FIG. 11A is a front left isometric view of an upper valve body of the pause valve assembly of FIG. 9A.
Figure 11B:
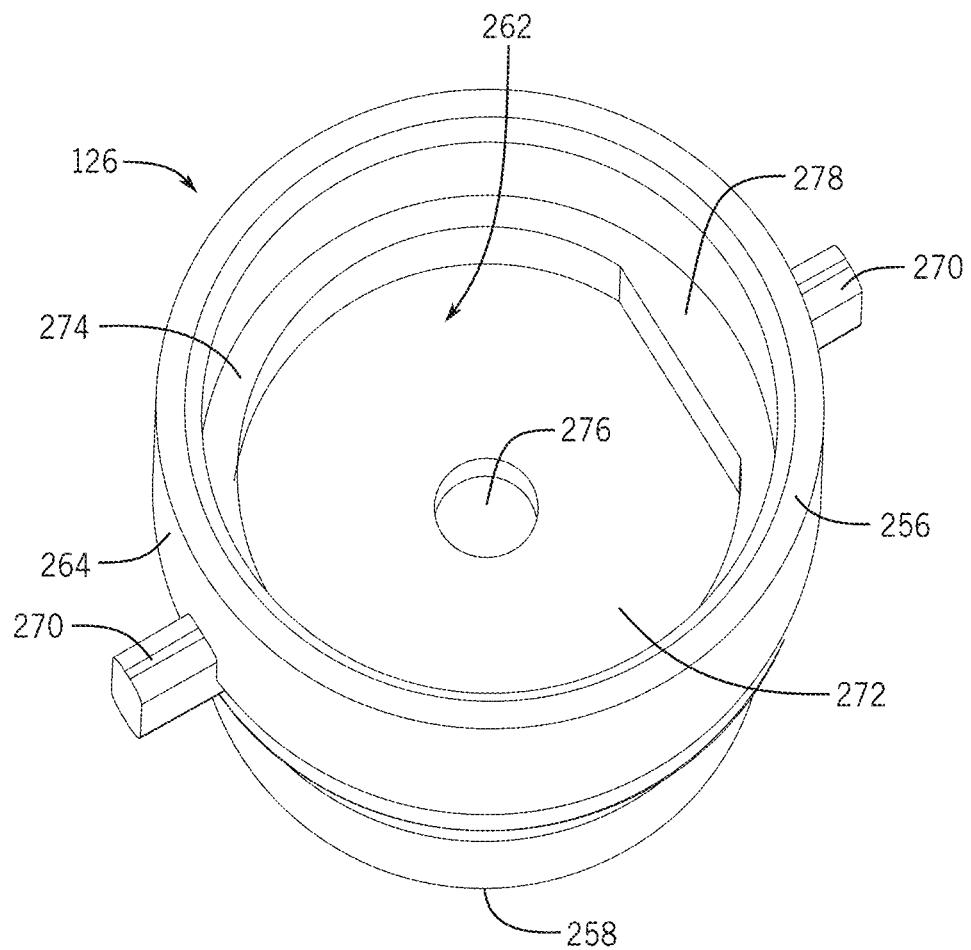
FIG. 11B is a front top isometric view of the upper valve body of FIG. 11A.
Figure 11C:
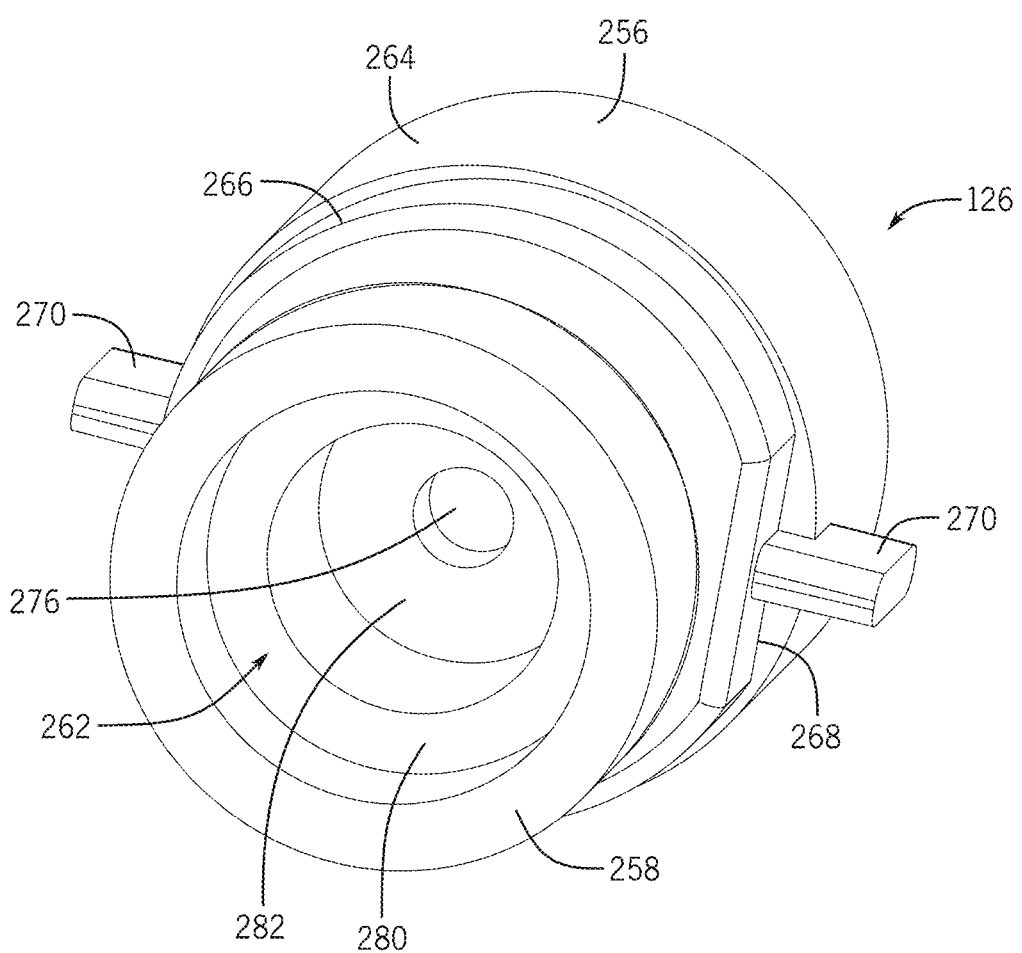
FIG. 11C is a bottom right isometric view of the upper valve body of FIG. 11A.
Figure 12A:
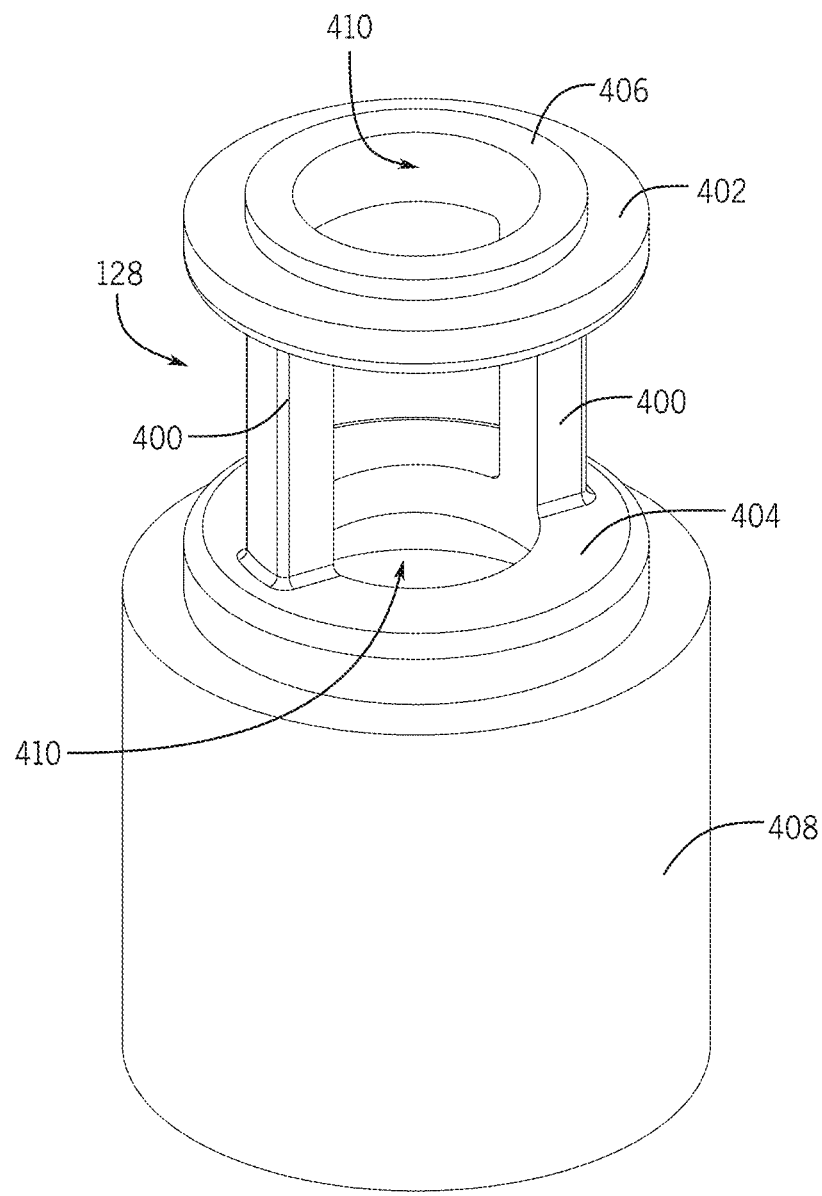
FIG. 12A is front top isometric view of a lower valve body of the pause valve assembly of FIG. 9A.
Figure 12B:
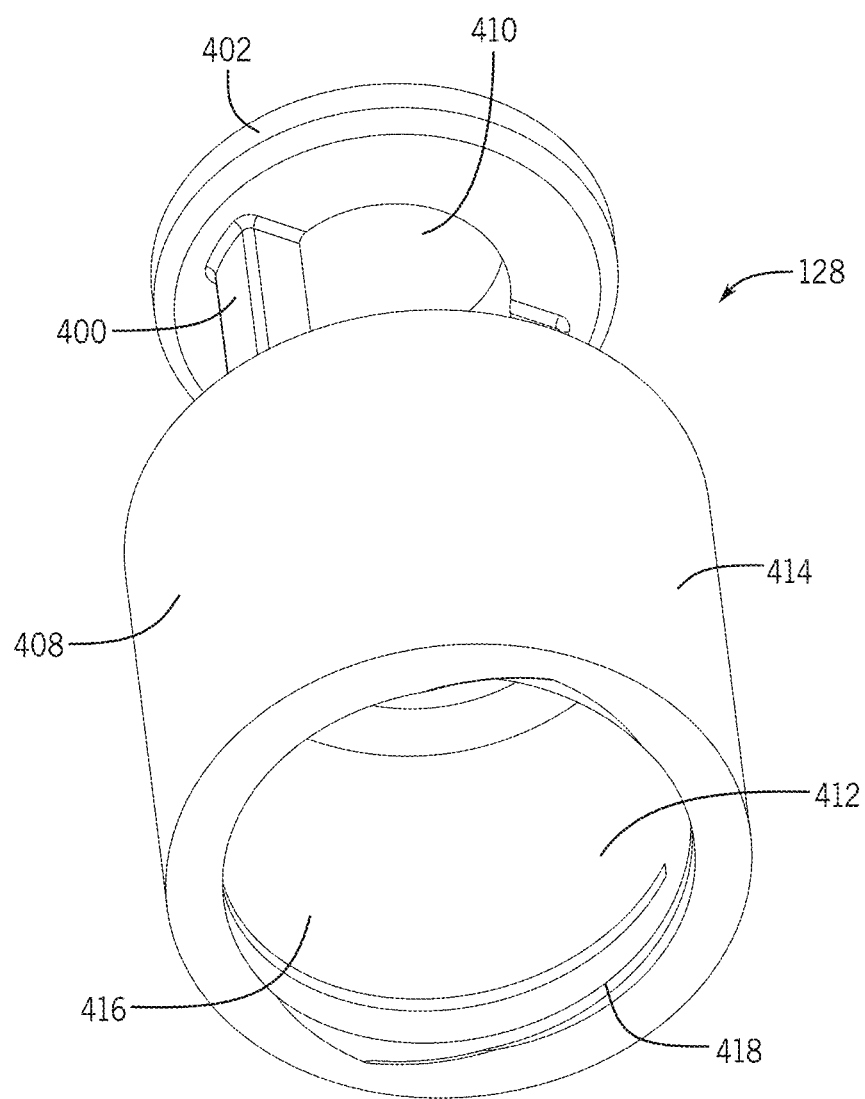
FIG. 12B is a front bottom isometric view of a lower valve body of the pause valve assembly of FIG. 9A.
Figure 13:
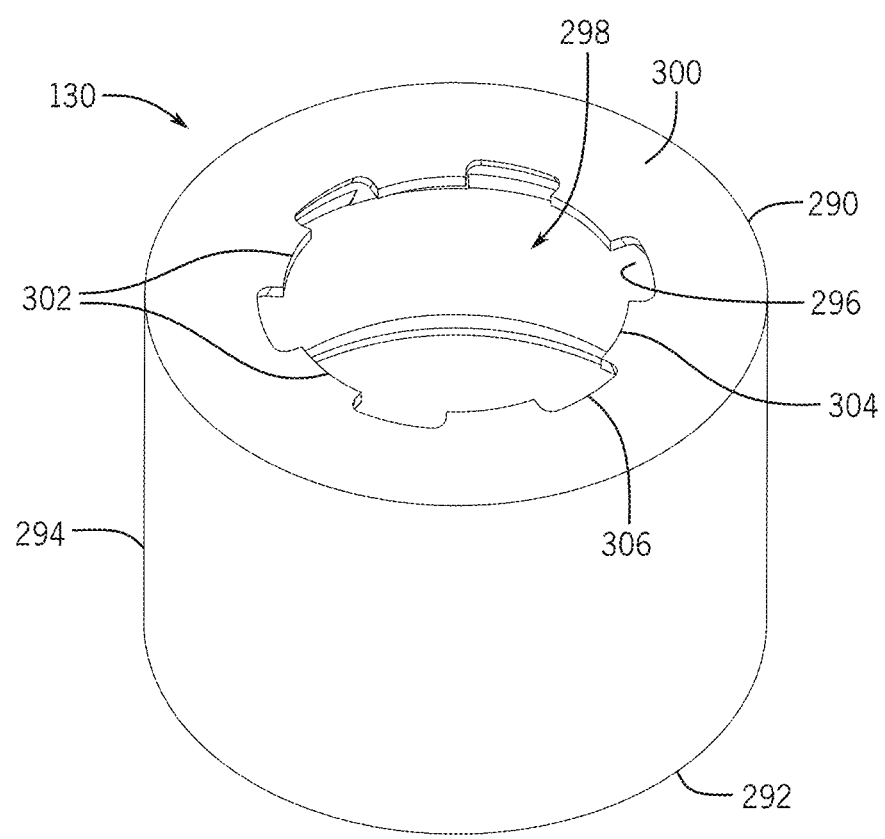
FIG. 13 is a front top isometric view of a shuttle retainer of the pause valve assembly of FIG. 9A.
Figure 14:
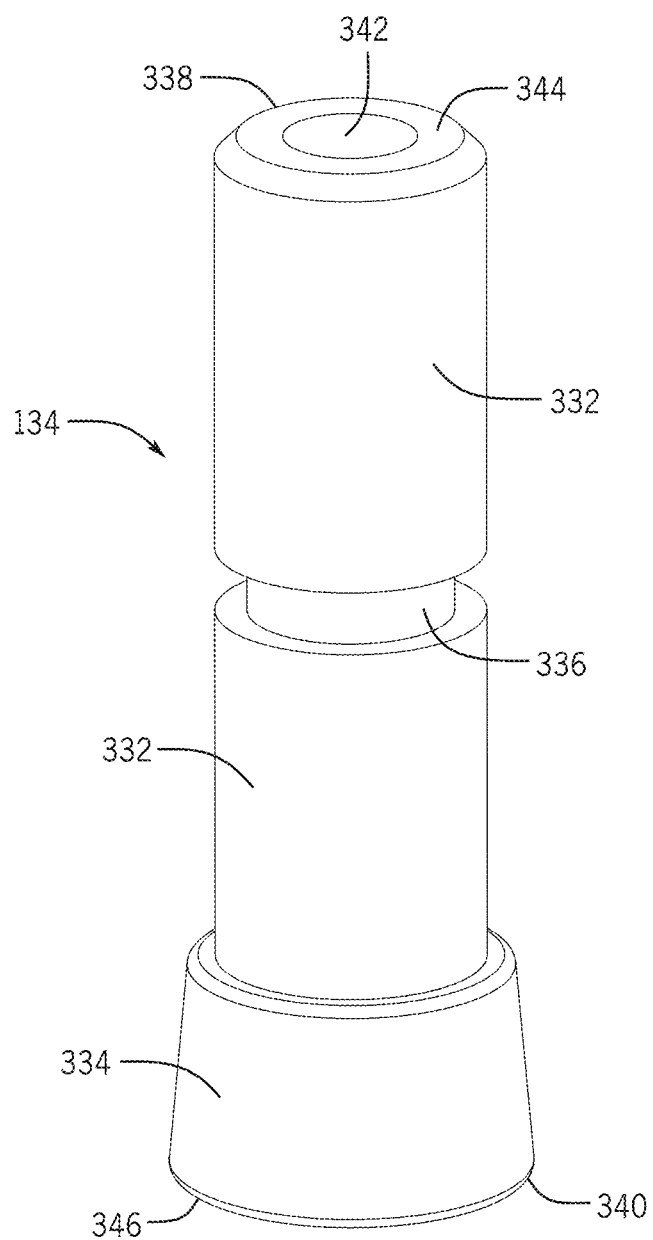
FIG. 14 is a front isometric view of a shuttle valve of the pause valve assembly of FIG. 9A.

One or more, such as two, arms 270 may extend laterally from the head 256 near the interface between the head upper and lower portions 264, 266. The arms 270 are positioned to engage and act as a track for the pause actuator 112 to move along. When two arms 270 are present, as shown in FIG. 11A-C, they may be positioned approximately 180 degrees apart from each other on the head 256. The arms 270 may be obround in cross-sectional shape as shown in FIG. 11A or may be other shapes.

As shown in FIG. 11B, the portion of the valve cavity 262 adjacent to the lower portion 266 of the head 256 may include a floor 272 and a shelf 274. A flow aperture 276 may be defined in the floor 272 and the flow aperture 276 may have a diameter less than the diameter of any of the head 256, neck 260, and base 258. The shelf 274 may include a keyed feature 278 positioned corresponding to the chord segment 268 of the lower portion 266 of the head 256.

As shown in FIG. 11C, a shelf wall 280 may extend below a bottom surface 282 of the floor 272 of the head 256 near the interface between the base 258 and neck 260 to define a narrowed diameter portion of the valve cavity 262. A sealing member 120c, such as U-cup, may be positioned on the shelf wall 280.

With reference to FIGS. 3-5B, 9A, 9B, 12A, and 12B, a lower valve body 128 operably connects the upper valve body 126 and the valve base 138. The lower valve body 128 may include two or more arms 400 connecting an upper plate 402 and a lower plate 404, a lip 406 defined on top of the upper plate 402, and a skirt 408 positioned below the lower plate 404. In the depicted embodiment, two cuboidal arms 400 are present and they are positioned opposite from each other across each of the upper and lower plates 402, 404. Each of the lip 406, upper plate 402, and lower plate 406 may be ring-shaped such that they define respective circular openings 410. The skirt 408 may be cylindrical in shape with a skirt cavity 412 defined therethrough. The skirt 408 may include an outer skirt wall 414 and an inner skirt wall 416. The inner skirt wall 416 may define the skirt cavity 412 and may include one or more tracks 418 formed as grooves or threading. A track 418 may extend approximately 360° around the interior skirt wall 416 in an uneven plane such that the ends of the track 418 do not meet but rather are offset from each other along a longitudinal axis of the handle 100. The external diameter of the upper plate 402 may be approximately equal to the external diameter of the lower plate 404, and both diameters may be greater than the external diameter of the lip 406 but less than the external diameter of the skirt 408.

A sealing member 120d, such as a U-cup, may be positioned within the skirt 408 under the lower plate 404.

With reference to FIGS. 3-5B, 9A, 9B, and 13, a shuttle retainer 130 receives fluid flowing past the poppet assembly 136 when the handle 100 is in pause mode. The shuttle retainer 130 may be generally cylindrical with an open first end 290 and open second end 292. The shuttle retainer 130 may include an exterior wall 294 and a stepped interior wall 296 defining a cavity 298 that extends between the open first and second ends 290, 292. The open first end 290 may include a top surface 300 having a plurality of tabs 302 separated by notches around the perimeter 304 of the opening 306. The tabs 302 may define a broken circular edge with a circumference slightly larger than the circumference of the shuttle valve 134.

With reference to FIGS. 3-5B, 9A-10, and 14, the shuttle valve 134 interrupts fluid flow through the handle 100 when pause mode is selected. The shuttle valve 134 may include a cylindrical body 332 and a frustum-shaped base 334. The body 332 may be interrupted by a connector groove 336 positioned about midway along the length of the body 332. The external diameter of the base 334 may be greater than the external diameter of the body 332, which may in turn be greater than the external diameter of the connector groove 336. The shuttle valve 134 may also include a flow lumen 342 defined within the body 332 and a base cavity 348 defined within the base 334. An open first end 338 of the shuttle valve 134 is fluidically connected to an open second end 340 by the flow lumen 342 and the base cavity 348. The body 332 of the shuttle valve 134 may include a top surface 344 and the base 334 may include a bottom surface 346.

With reference to FIGS. 3-5B, 9A, 9B, and 15, a poppet assembly 136 is used to selectively disconnect fluid flow from the hose 108 to the valve cap 122. The poppet assembly 136 may include a generally circular cap 312 connected to a poppet support plate 316 by a cylindrical poppet neck 318. An annular platform 314 may encircle the neck 318 above the poppet support plate 316. The diameter of the platform 314 may be approximately equal to the diameter of the cap 312 and less than the widest diameter of the poppet support plate 316. The poppet support plate 316 includes a first surface 320, a second surface 322, and a plurality of sprockets 324 extending outwardly from the platform 314. Two adjacent sprockets 324 may be separated from each other to define a flow path 326 therebetween. A sealing member 120e may be seated around the poppet neck 318 between the cap 312 and platform 314.

Figure 16:
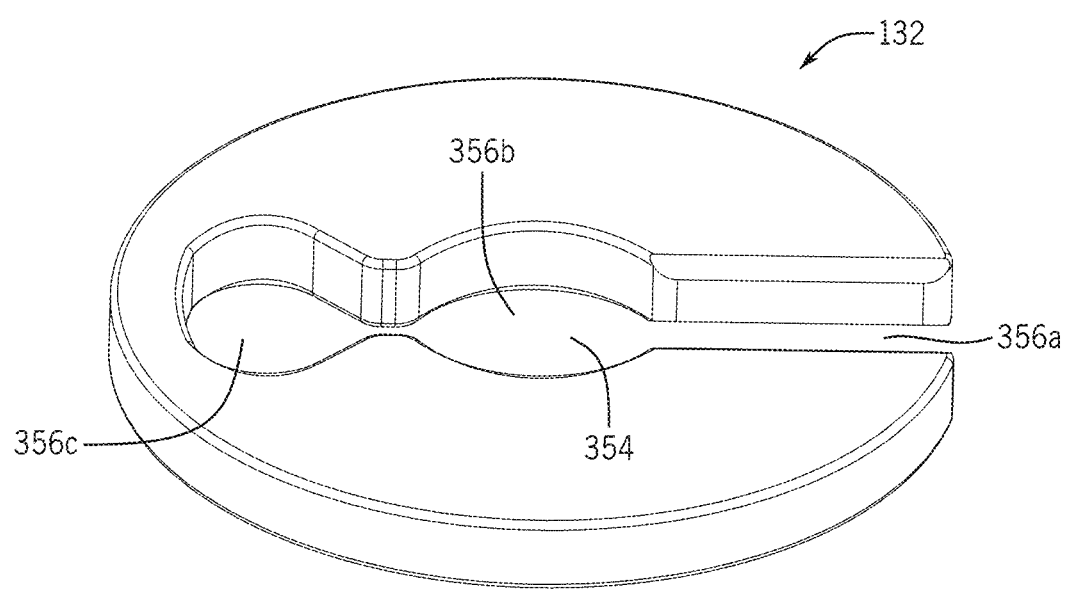
FIG. 16 is a front top isometric view of a retaining ring of the pause valve assembly of FIG. 9A.

As shown in FIGS. 3-5B, 9A, 9B, 10, and 16, a retaining ring 132 operably connects the pause actuator 112 to the shuttle valve 134. The retaining ring 132 may be disc-shaped and may include a keyhole cutout 354, which may include a plurality of forms. For example, and as shown in FIG. 16, the retaining ring may have a first slot 356a, a center aperture 356b, and a hinge aperture 356c. The center aperture 356b in the keyhole cutout 354 may be sized to fit around the connector groove 336 of the shuttle valve 134. In some embodiments, the retaining ring 132 may be a snap ring.

Figure 10:
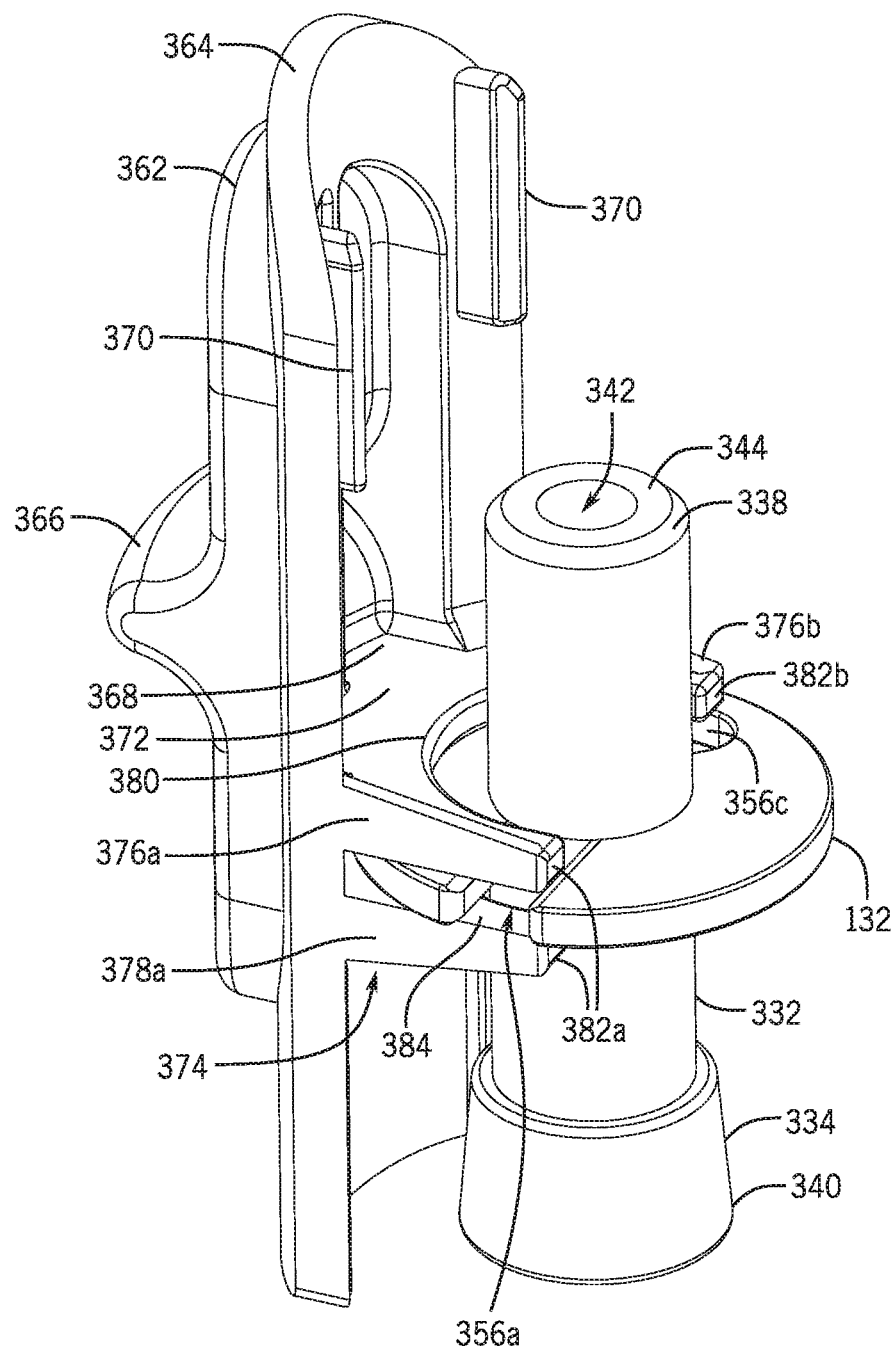
FIG. 10 is a right rear isometric view of a portion of the pause valve assembly of FIG. 9A.

With reference to FIGS. 2A, 2B, 3, 5A, 5B, 9A, 9B, and 10, the pause actuator 112 is moved by a user to place the handle in a pause or an irrigate mode. The pause actuator 112 may include an exterior slider plate 362 and an interior slider plate 364. The exterior slider plate 362 may include a grip portion 366 for aiding a user in gripping and moving the pause actuator 112. The interior slider plate 364 may have a concave shape and may include a concave or rear face 368 from which one or more walls 370 extend. For example, two walls 370 that are generally rectangular cuboids in shape are shown in FIG. 10. An upper shelf 372 and a lower shelf 374 may also extend parallel to each other from the rear face 368. A first upper prong 376a and a second upper prong 376b may extend from the upper shelf 372 away from the rear face 368. A first lower prong 378a and a second lower prong 378b may similarly extend from the lower shelf 374. The first prongs 376a, 378a are laterally spaced from the second prongs 376b, 378b and are connected by a shelf wall 380 that forms a semicircle from the terminus 382a of one prong 376a, 378a to the terminus 382b of the laterally opposed prong 376b, 378b. Each upper prong 376a, 376b may be separated from its proximal lower prong 378a, 378b by a retaining gap 384 between the upper and lower shelves 372, 374. Although shown as cuboidally shaped in FIG. 10, the prongs 376a, 376b, 378a, 378b may be any shape.

Swivel Assembly

With reference to FIGS. 3-5B and 17, the swivel assembly 143 will now be discussed in more detail. The swivel assembly 143 may help minimize or prevent translation of rotational movement of the handle 100 or the hose 108 relative to the other. The swivel assembly 143 may include a valve base 138 and a bushing 140. The valve base 138 is configured to be received within the stationary lower valve body 128. The valve base 138 may include an annular protruding rim 424, a cylindrical body 426, and an elongated barbed tip 428. The valve base 138 defines a flow cavity 430 from the barbed tip 428 through to the top surface 432 of the rim 424. The rim 424 may include one or more threads 434. Each thread 434 may extend approximately 360° around the rim 424 in an uneven plane such that the ends of the thread 434 do not meet but rather are offset from each other along a longitudinal axis of the handle 100. The threads 434, which may be complimentary to the tracks 418 of the inner skirt wall 416 of the skirt 408 of the lower valve body 128, may help to align or assemble the valve base 138 and lower valve body 128. The barbed tip 428 may include one or more gripping components 436 that enhance the connection between the valve base 138 and the hose 108.

With reference to FIGS. 3-5B, the swivel assembly 143 may also include a cylindrical bushing 140 defining a barb aperture 442 configured to receive the barbed tip 428 of the valve base 138. The bushing 140 may include a rim 444 and a body 446.

Assembly of the Oral Irrigator

An illustrative example of assembly of the handle 100 will now be discussed. It should be noted that the below description is meant as exemplary only and the handle 100 may be assembled in any manner and in any order. In one embodiment, the handle components of FIGS. 3-5B and 7A-17 may be assembled within the housing 102 as follows.

To assemble the tip eject mechanism 141, the upper end 223 of the body 226 of the valve cap 122 may be received in the valve cap cavity 476 of the latch 121. The perimeter of the interior lip 470 may directly align with or may be slightly offset from the tip cavity 222 of the valve cap 122. The upper end 223 of the body 226 of the valve cap 122 may not completely fill the volume of the valve cap cavity 122 such that lateral movement of the latch 121 toward or away from the tip eject button 110 is permitted. The nose 201 of the interior slider portion 200 of the tip eject button 110 may abut and interface with the chamfered wall 478 of the latch 121.

When the housing 102 is assembled, the top surface 466 of the latch 121 may be below and adjacent to the first ledge 150a, 150b, and the bottom of the latch body 452 may be adjacent to or rest upon the second ledge 152a, 152b.

When the housing is assembled, the exterior slider portion 196 of the tip eject button 110 may be positioned within the pocket 186 of the housing 102, the neck 202 may be received within the opening 194 within the pocket 186, and the interior slider portion 200 may be positioned against an interior wall 174 of the housing 102 opposite from the pocket 186. The upper surface 188 and lower surface 190 of the pocket 186 may extend beyond the length of the tip eject button 110 such that the pocket 186 is longer than the exterior and interior slider portions 196, 200 and the neck 202 is shorter than a longitudinal dimension of the opening 194 in the pocket 186. In this configuration, the tip eject button 110 is both retained within the opening 194 in the pocket 186 and can slide longitudinally within the pocket 186 as the exterior and interior slider portions 196, 200 travel on either side of the upper and lower surfaces 188, 190 of the pocket 186.

To assemble the pause valve assembly, the lip 406 of the lower valve body 128 may be received in the base 258 of the upper valve body 126 and may be positioned below and adjacent to the sealing member 120c positioned under the shelf wall 280 of the valve cavity 262.

The shuttle retainer 130 may be received in the skirt cavity 412 of the lower valve body 128. The exterior wall 294 of the shuttle retainer 130 may be positioned adjacent to the inner skirt wall 416 of the lower valve body 128. The second end 292 of the shuttle retainer 130 may be positioned adjacent to the first surface 320 of the poppet support plate 316. The top surface 300 of the shuttle retainer 130 may be positioned below and adjacent to the sealing member 120d positioned under the lower plate 404 of the lower valve body 128. The configuration of tabs 302 and notches in the top surface 300 of the shuttle retainer 130 may permit water to reach the sealing member 120d and press the sealing member 120d against the shuttle valve 134 and the lower plate 404 more uniformly, thereby creating a faster or stronger seal than in the absence of water.

The base 334 and a lower portion of the body 332 of the shuttle valve 134 may be received in the cavity 298 of the shuttle retainer 130. The first end 338 of the shuttle valve 134 may be received in the valve cavity 262 of the upper valve body 126. The arms 400 of the upper valve body 126 may flank a portion of the body 332 of the shuttle valve 134. A shuttle compartment 284 may be formed in the space between the bottom surface 282 of the floor 272 of the head 256 of the upper valve body 126 and the top surface 344 of the body 332 of the shuttle valve 134 when the handle 100 is in pause mode. The retaining ring 132 may be flexed at the hinge aperture 356c to widen the slot 356a and seat the center aperture 356b of the retaining ring 132 within the connector groove 336 of the shuttle valve 134.

The cap 312 and the sealing member 120e positioned around the poppet neck 318 of the poppet assembly 136 may be received in the base cavity 348 of the shuttle valve 134. The first surface 320 of the poppet support plate 316 may be positioned below and adjacent to the bottom surface 346 of the base 334 of the shuttle valve 134 and below and adjacent to the second end 292 of the shuttle retainer 130.

The interior slider plate 364 of the pause actuator 112 may extend from approximately the head 256 of the upper valve body 126 to the skirt 408 of the valve lower housing. The walls 370 on the rear face 368 of the interior slider plate 364 may be positioned adjacent to the head 256 of the upper valve body 126, at least when the pause mode is selected. The shelf wall 380 may face the body 332 of the shuttle valve 134. The retaining ring 132 may be captured in the gap 384 formed between the upper prongs 376a, 376b, and lower prongs 378a, 378b. One pair of upper and lower prongs 376a, 378a may traverse some or all of the slot 356a of the keyhole 354 of the retaining ring 132. Another pair of upper and lower prongs 376b, 378b may traverse some or all of the hinge aperture 356c.

The top surface 432 of the protruding rim 424 of the valve base 138 may be positioned below and adjacent to the second surface 322 of the poppet support plate 316. One or more of the threads 434 of the rim 424 may be mated with the one or more complementary tracks 418 on the interior skirt wall 416 of the lower valve body 128.

When the housing 102 is assembled, the base 258 of the upper valve body 126 is positioned adjacent to and below the fourth ledge 156a, 156b. Each arm 270 of the upper valve body 126 may extend perpendicularly to and be positioned between a vertical support wall 148a of the first shell 114 and a vertical support wall 148b of the second shell 116. The upper plate 402 of the lower valve body 128 may be positioned above the fifth ledge 158 and the skirt 408 of the lower valve body 128 may be positioned above and adjacent to the seventh ledge 162a, 162b.

When the housing 102 is assembled, the exterior slider plate 362 of the pause actuator 112 may be positioned within the pause actuator aperture 204 in the first shell 114 and the interior slider plate 364 may be positioned against an interior wall 174 of the first shell 114 opposite at least a portion of the pause actuator frame 390. The upper and lower portions of the aperture 204 extend beyond the length of the exterior slider plate 362 such that the aperture 204 is longer than the exterior slider plate 362 and shorter than the interior slider plate 364. In this configuration, the pause actuator 112 is both retained within the aperture 204 and can slide longitudinally within the aperture 204 as the exterior and interior slider plates 362, 364 travel on either side of the aperture 204 and frame 390.

To assemble the swivel assembly 143, the barbed tip 428 of the valve base 138 is received in the barb aperture 442 of the bushing 140. Eighth ledges 164a, 164b of the shells 114, 116 may be positioned beneath the rim 444 of the bushing 140. An end of the hose 108 may fit over the barbed tip 428. The hose 108 may exit the cavity 172 of the assembled housing 102 at the aperture 146.

To connect the tip eject mechanism 141 and the backflow valve 124, the lower end 224 of the valve cap 122 may be received in the upper portion 248 of the valve cavity 246 of the backflow valve body 124. The lower end 224 may be positioned above and adjacent to the sealing member 120b seated on the ledge 250 of the top end 230 of the backflow valve body 124. The rim 220 of the valve cap 122 may be captured between the underside of the second ledge 152a, 152b of the first and second shells 114, 116 and the top end 230 of the backflow valve body 124.

To connect the backflow valve 124 and pause valve assembly 142, the neck 234, rim 236, and bottom end 232 of the backflow valve body 124 may be received in the portion of the valve cavity 262 of the upper valve body 126 adjacent to the head 256. The rim 236 of the backflow valve body 124 may be positioned adjacent to the shelf 274 of the upper valve body 126 such that the keyed feature 240 of the bottom edge 238 of the backflow valve body 124 mates with the keyed feature 278 of the shelf 274 of the upper valve body 126. The sealing member 120a seated in the neck 234 of the backflow valve body 124 may be positioned in the valve cavity 262 of the head 256 of the upper valve body 126.

To connect the pause valve assembly 142 and the swivel assembly 143, the rim 424 of the valve base 138 is received in the skirt 408 of the lower valve body 128 and is positioned under the poppet support plate 316.

After the shells 114, 116 are assembled, the handle collar 118 may be positioned over the neck 180a, 180b and may be secured to the handle housing 102 by several arcuate tabs 212 extending radially inward from a sidewall of the handle collar 118 that capture the lip 208a, 208b of the neck 180a, 180b (see FIGS. 4, 5A, and 5B). The arcuate tabs 212 of the handle collar 118 may be separated from the bodies 192a, 192b of the first and second shell 114, 116 by a gap 214, the span of which may be decreased by depressing the handle collar 118 towards the bodies 192a, 192b.

Alternative Embodiment

FIGS. 18-27 depict another embodiment of a handle 500. Compared to the handle 100, similarly numbered features of the components of the handle 500 have similar designs, constructions, function, and operations as those of the components described above unless otherwise noted. The exterior of the handle 500 may appear the same as or similar to the handle 100 of FIGS. 1, 2A, and 2B. Compared to the handle 100, the handle 500 may not include either or both of a backflow valve body 124 and a bushing 140.

Figure 18:
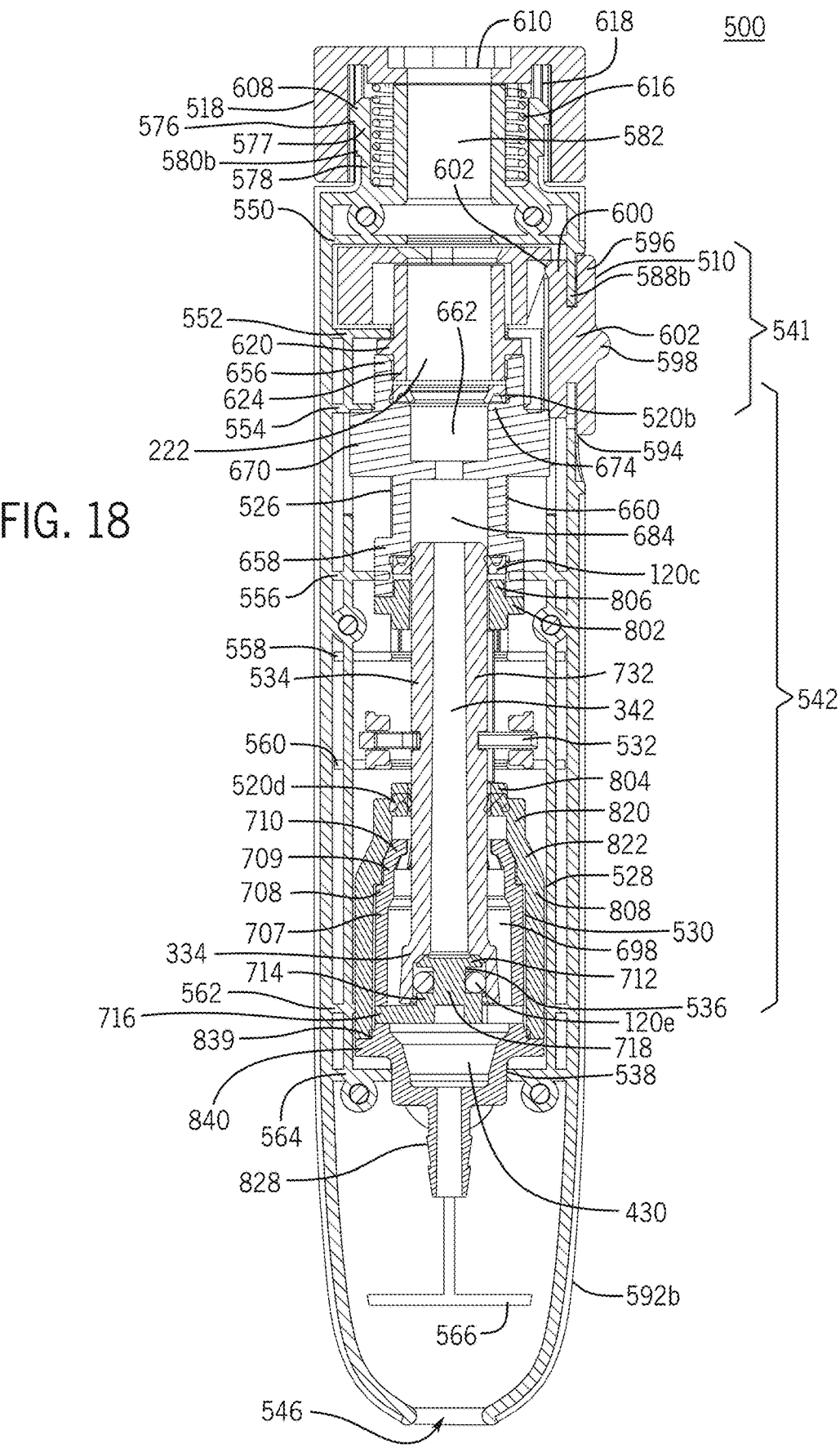
FIG. 18 is an elevation view in cross section of another embodiment of a handle.
Figure 19:
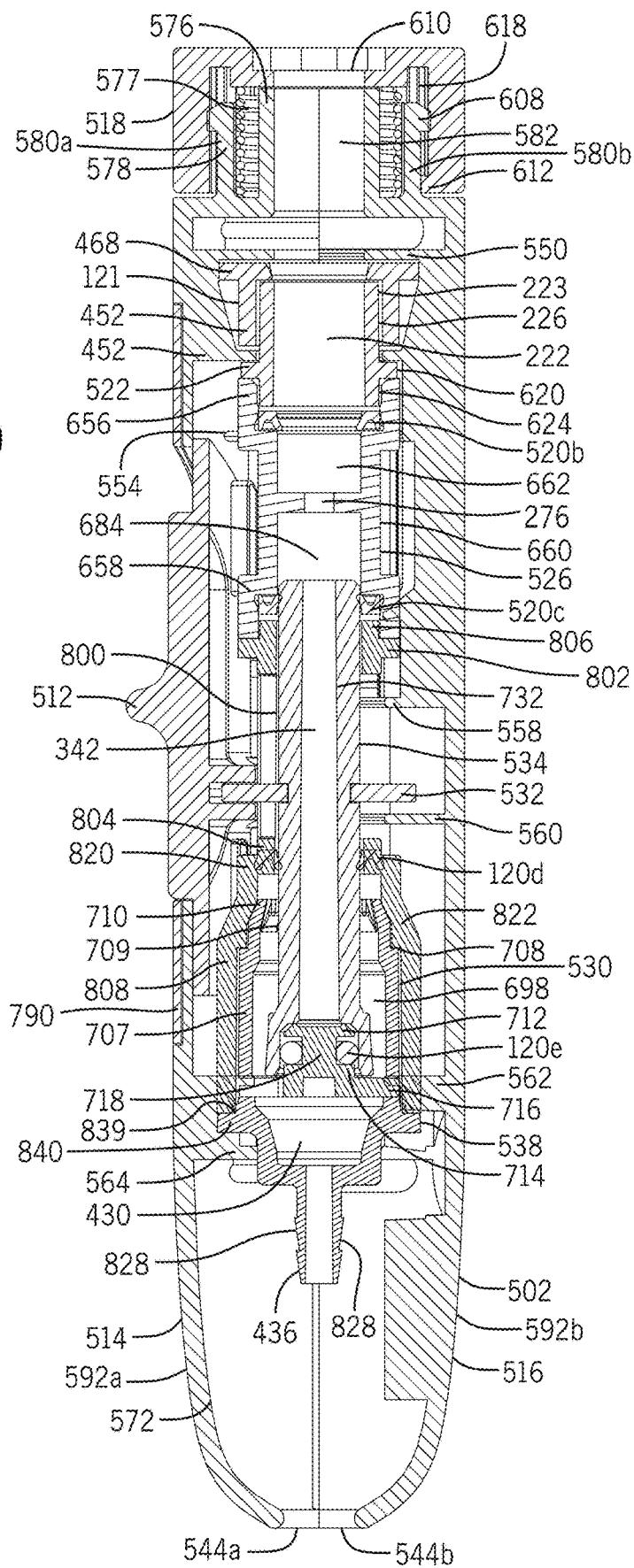
FIG. 19 is an elevation view in cross section of the handle of FIG. 18.
Figure 20B:
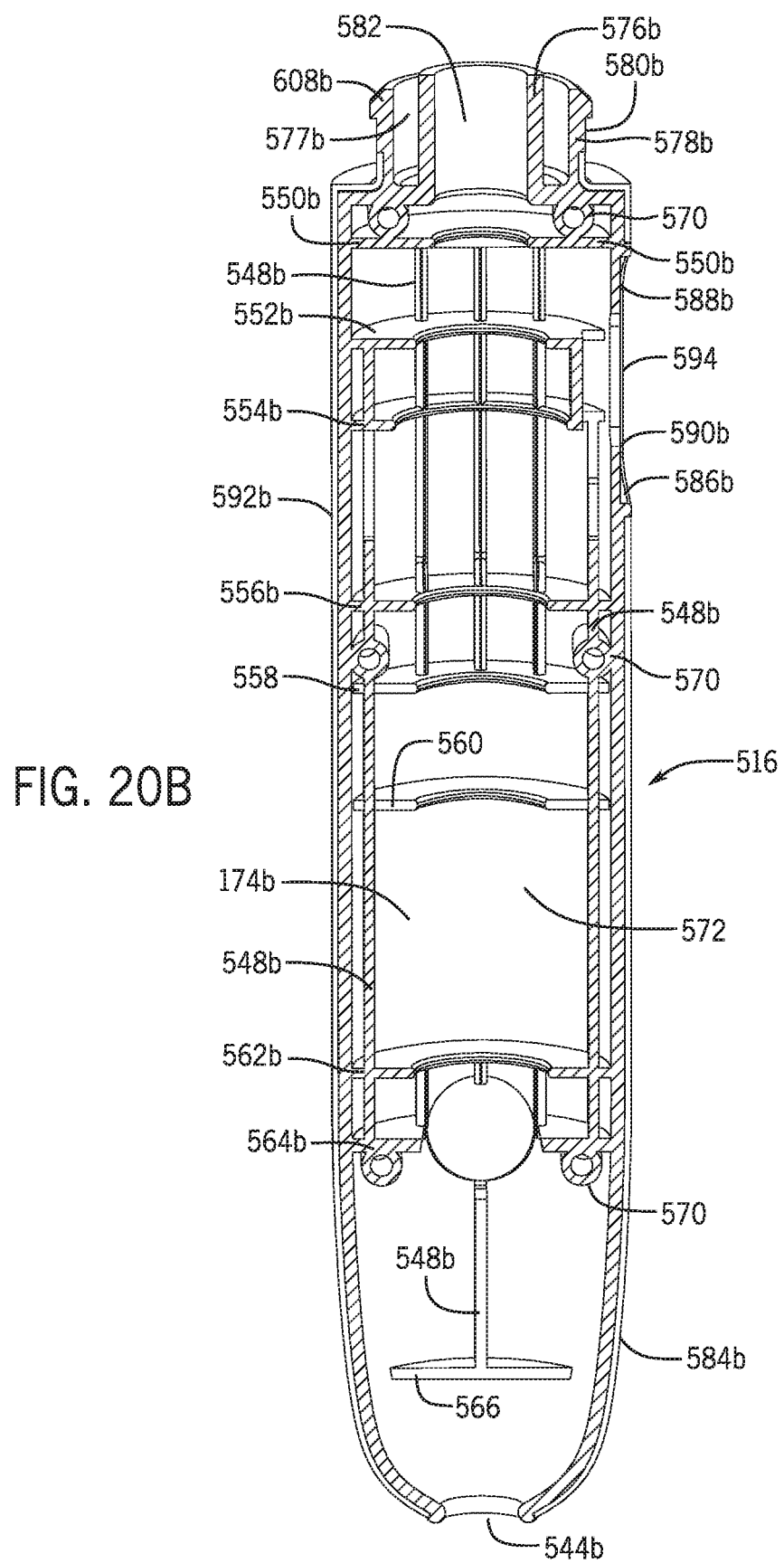
FIG. 20B is a front isometric view of a second shell of the handle of FIG. 18.

As with the handle 100 shown in FIGS. 1-17, the handle 500 of FIGS. 18-27 may include a first shell 514 and a second shell 516, each comprised of a neck 580a, 580b and shell body 592a, 592b (see FIGS. 20A and 20B). The bodies 592a, 592b of the first and second shells 514, 516, respectively, together define a handle cavity 572. The first shell 514 may include first, second, third, fourth, seventh, and eighth ledges 550a, 552a, 554a, 556a, 562a, and 564a, respectively, that are constructed similarly to the previously described ledges 150a, 152a, 154a, 156a, 162a, and 164a, respectively, and also have similar functions.

The second shell 516 may include first, second, third, fourth, fifth, sixth, seventh, eighth, and ninth ledges 550b, 552b, 554b, 556b, 558, 560, 562b, 564b, and 566, respectively, that are constructed similarly to the previously described ledges 150b, 152b, 154b, 156b, 158, 160, 162b, 164b, and 168, respectively, and also have similar functions.

The bodies 592a, 592b of the first and second shells 514, 516 may also include a plurality of vertical support walls 548a, 548b, pegs 569, and holes 570 similar to the corresponding features of the first-described embodiment.

With reference to FIGS. 18, 20A, and 20B, the outer surface of the exterior walls 584a, 584b of the first and second shells 514, 516 may each define a C-shaped depression 586a, 586b with respective upper surfaces 588a, 588b and lower surfaces 590a, 590b similar to the corresponding features described above. When the handle 500 is assembled, opposing depressions 586a, 586b define a pocket 586 surrounding an opening 594. An elongate tip eject button 510 may be formed with an exterior slider portion 596 and an interior slider portion 600 that are separated from each other by a neck 602. The exterior slider portion 596 may include a tab grip 598. The interior slider portion 600 may include a nose 601 that projects radially inward therefrom. The design and construction of the tip eject button 510, and its position relative the first and second shells 514, 516 may be the same as or similar to the tip eject button 110 of the first-described embodiment.

As described above for the first shell 114, the first shell 514 of the present embodiment may also include a pause actuator aperture 604 for receiving a pause actuator 512 and a recessed pause actuator frame 790. The pause actuator aperture 604 may have an upper portion 792 and a lower portion 794.

With reference again to FIGS. 20A and 20B, the body 592a, 592b of each of the first and second shell 514, 516 may terminate in a semicircular hose cut-out 544a, 544b. When the first and second shells 514, 516 are assembled, the cut-outs 544a, 544b together define a substantially circular aperture 546 through which a hose passes.

The neck 580a, 580b of each of the first and second shell 514, 516, respectively, includes an interior wall 576a, 576b, an exterior wall 578a, 578b, and an annular recess 577a, 577b substantially as described above. The exterior walls 578a, 578b may include a lip 608a, 608b and the interior walls 576a, 576b, when assembled into the handle 500, define a cylindrical tip cavity 582 configured to receive a tip 104.

The handle 500 may include a handle collar 518 having similar features and functions to the handle collar 118 described above. The handle collar 518 may include a tip-receiving aperture 610 for receiving the tip 104, an annular well 618 for receiving a spring 616, and arcuate tabs 612 for securing the collar 518 onto the first and second shells 514, 516 (see FIG. 18).

With reference to FIGS. 18 and 19, a tip eject mechanism 541 of the handle 500 may be substantially the same in its design and operation as the tip eject mechanism 141 described above.

With further reference to FIGS. 18 and 19, a pause valve assembly 542 of the handle 500 may include an upper valve body 526, a lower valve body 528, a shuttle valve 534, a shuttle retainer 530, a poppet assembly 536, and a pause actuator 512 operably connected to the shuttle valve 534 by a retaining ring 532 substantially the same as the pause valve assembly 142 described above with the following exceptions.

Figure 22A:
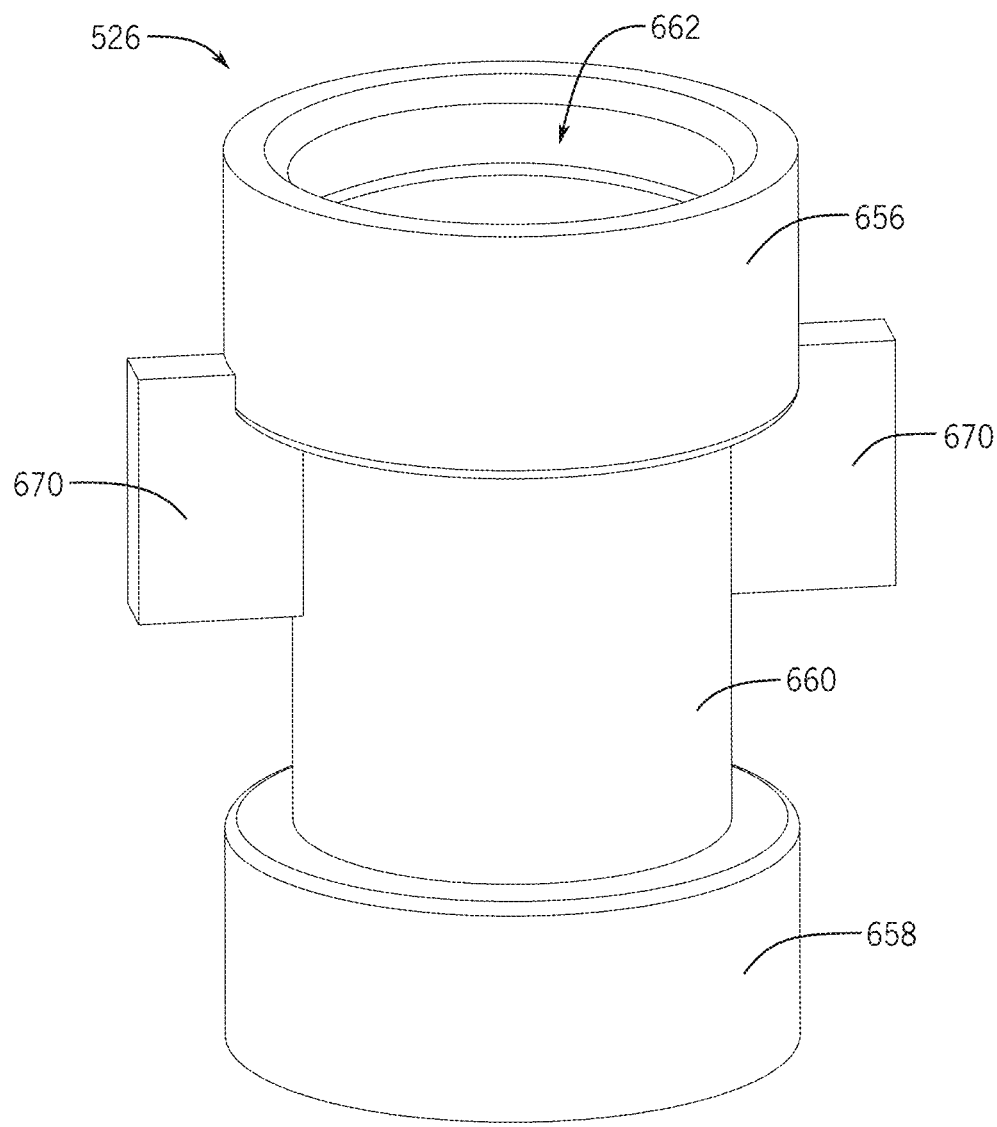
FIG. 22A is a front isometric view of an upper valve body of the pause valve assembly of FIG. 21.
Figure 22B:
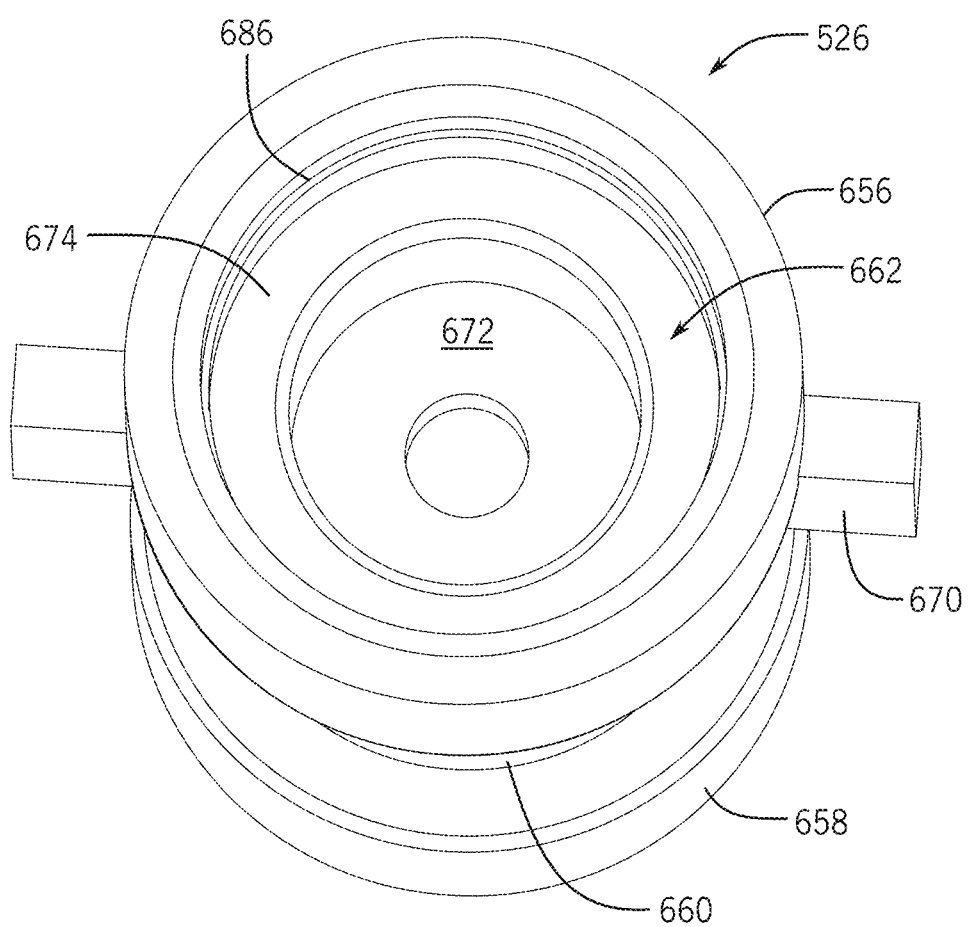
FIG. 22B is a front top isometric view of the upper valve body of FIG. 22A.
Figure 22C:
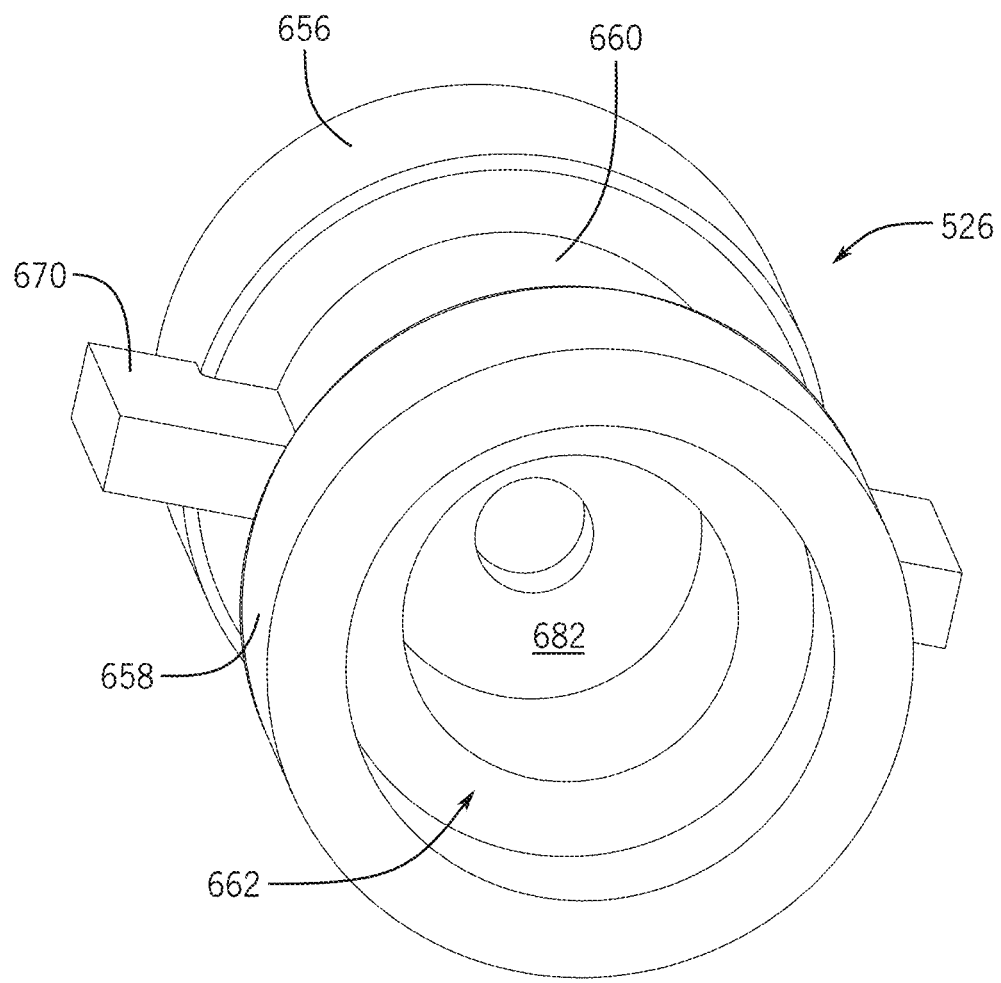
FIG. 22C is a bottom right isometric view of the upper valve body of FIG. 22A.
Figure 23A:
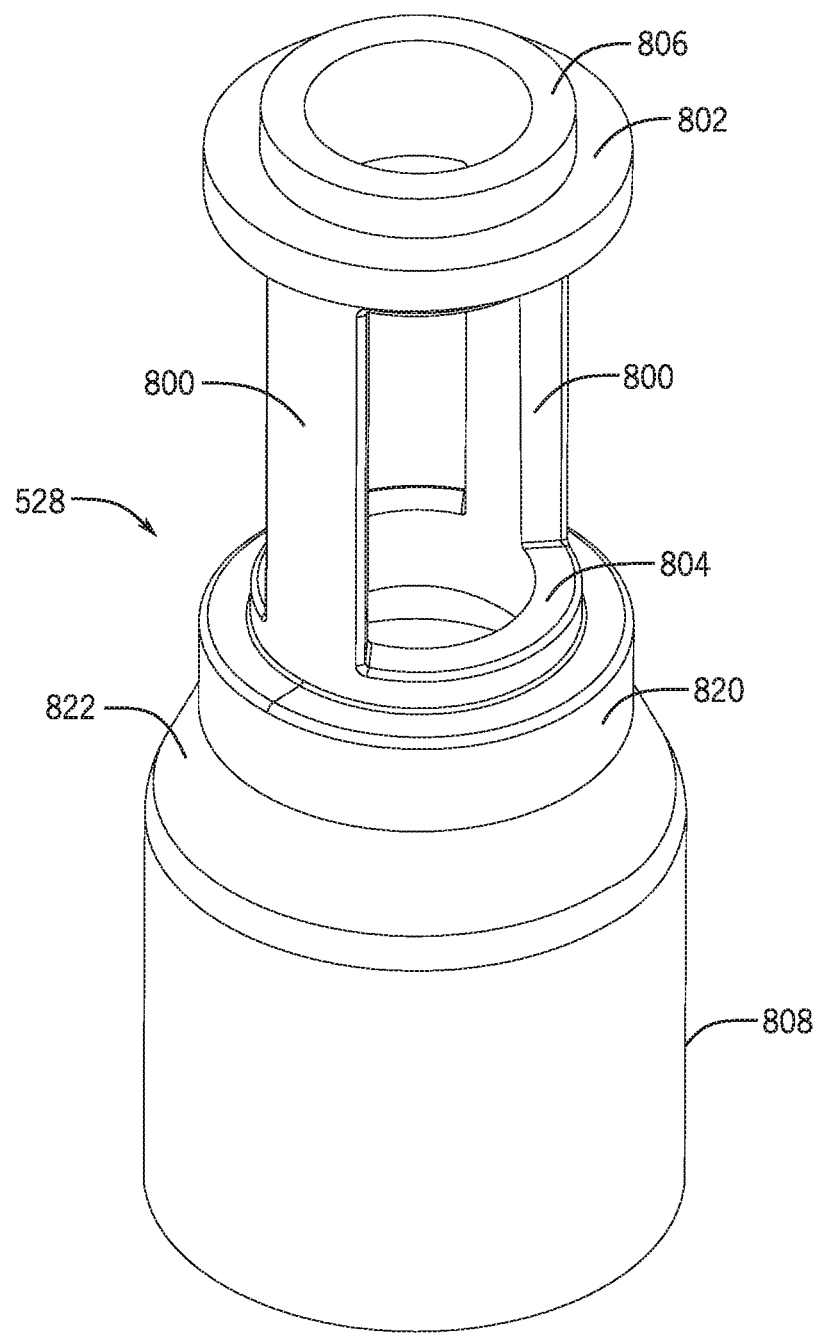
FIG. 23A is front top isometric view of a lower valve body of the pause valve assembly of FIG. 21.
Figure 23B:
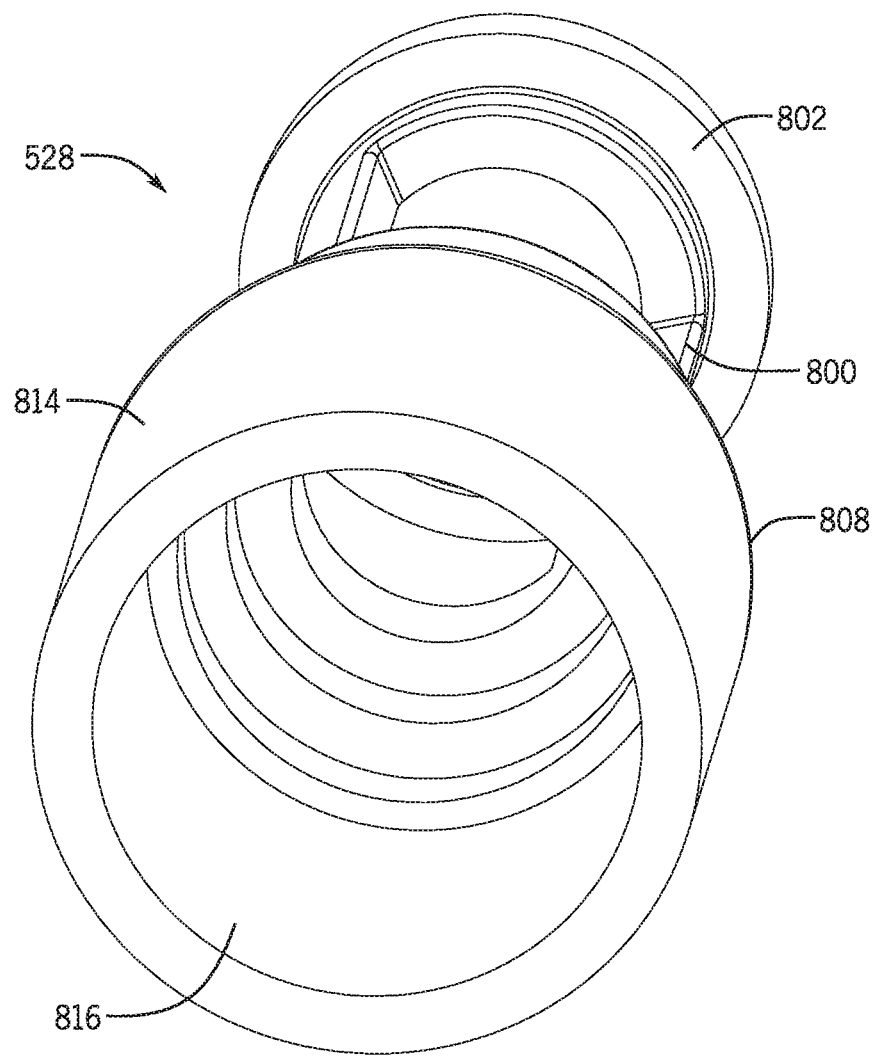
FIG. 23B is a front bottom isometric view of a lower valve body of the handle of FIG. 21.

With reference to FIGS. 18, 19, and 22A-C, an upper valve body 526 may be substantially the same as the upper valve body 126 described above. The portion of the valve cavity 662 adjacent to the head 656 may include a floor 672 and a ledge 686 and a shelf 674 positioned between the floor 672 and ledge 686. One or more arms 670 may extend laterally from the head 656 and neck 660. The arms 670 may be rectangular cuboids in shape as shown in FIG. 22A-C or may be other shapes. The external diameters of the head 656 and base 658 may be approximately equal and both may be greater than the external diameter of the neck 660.

In the example depicted in FIGS. 22A-C, and compared to the example depicted in FIGS. 11A-C, the head 656 may be shorter, the neck 660 may be longer, and the base 658 may be wider. The head 656 may not include separate upper and lower portions 264, 266. The head 656 may not include a chord segment 268 and the shelf 674 may not include a keyed feature 278.

With reference to FIGS. 18, 19, 23A, and 23B, a lower valve body 528 may be substantially the same as the lower valve body 128 described above. The lower valve body 528 includes an annular wall 820 positioned between a lower plate 804 and a skirt 808. An upper portion 822 of the skirt 808 may angle inward toward the annular wall 820. The external diameter of the upper plate 802 may be approximately equal to the external diameter of the annual wall 820, and both diameters may be greater than the external diameter of the lip 806 but less than the external diameter of the skirt 808. In the example depicted in FIGS. 23A and 23B, and compared to the example depicted in FIGS. 12A and 12B, the lip 806 may be taller, the arms 800 may be elongated, and the skirt 808 may be truncated. The inner skirt wall 816 may not include any tracks 418.

A sealing member 520d, such as a U-cup, may be positioned under the lower plate 804 adjacent the annual wall 820. The sealing member 520d may be overmolded into the lower plate 804 or the annual wall 820.

Figure 24:
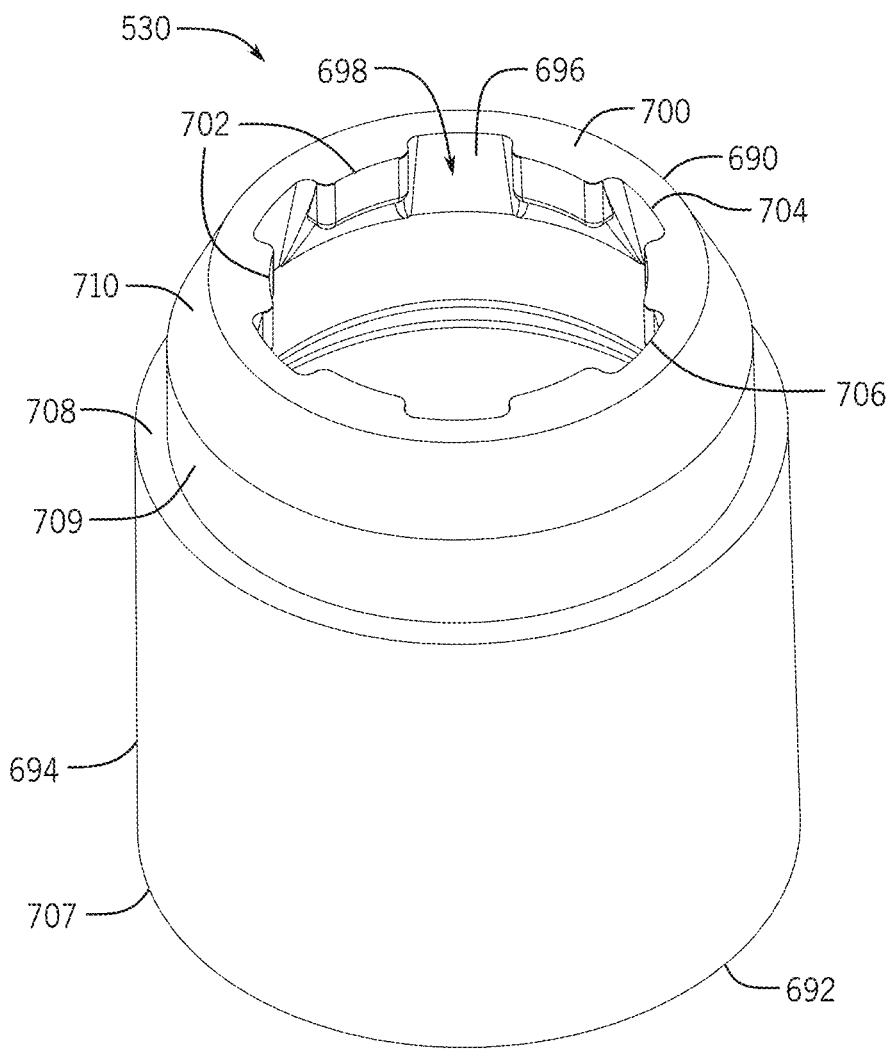
FIG. 24 is a front top isometric view of a shuttle retainer of the pause valve assembly of FIG. 21.

With reference to FIGS. 18, 19, and 24, a shuttle retainer 530 may include a cylindrical body 707 and a lip 709 that meet at a ledge 708. The shuttle retainer 530 may include an exterior wall 694 and a stepped interior wall 696 defining a cavity 698 that extends from an open first end 690 to an open second end 692. The open first end 690 may include a top surface 700 having a plurality of tabs 702 separated by notches around the perimeter 704 of the opening 706. The tabs 702 may define a broken circular edge with a circumference slightly larger than the circumference of the shuttle valve 534. The upper portion 710 of the lip may angle inwards towards the tabs 702 and opening 706.

Figure 25:
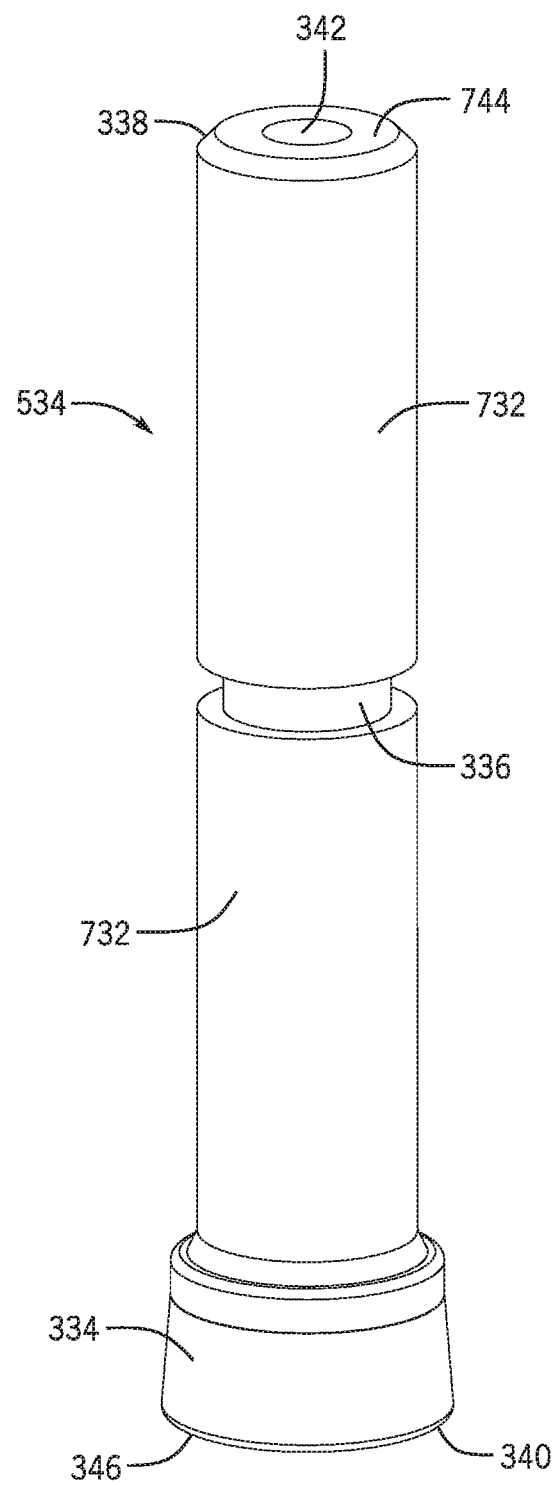
FIG. 25 is a front isometric view of a shuttle valve of the pause valve assembly of FIG. 21.

With reference to FIG. 25, the shuttle valve 534 may have substantially the same features as the shuttle valve 134 descripted above. In the example depicted in FIG. 21, the body 732 is elongated compared to the body 332 of the shuttle valve 134 depicted in FIG. 14.

Figure 26:
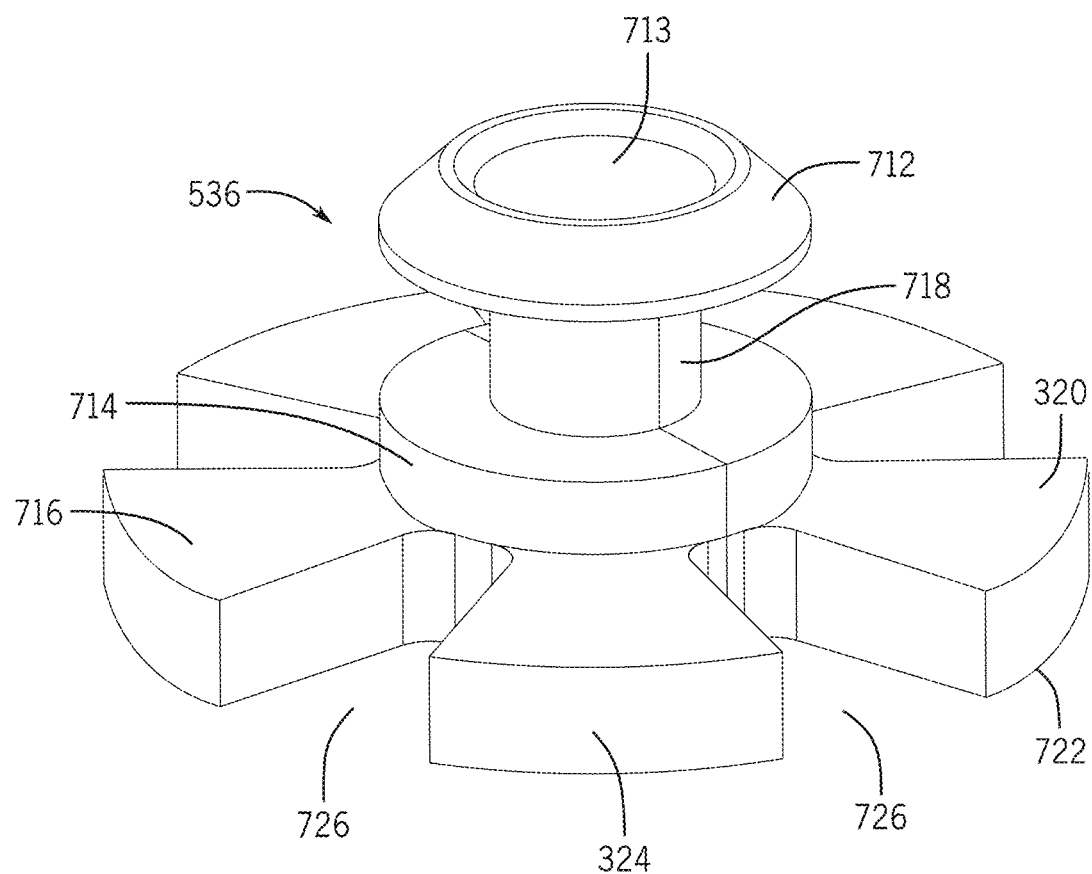
FIG. 26 is a front top isometric view of a poppet assembly of the pause valve assembly of FIG. 21.

With reference to FIG. 26, the poppet assembly 536 may be substantially the same in its design and operation as the poppet assembly 136 described above. In the example depicted in FIG. 26, and compared to the example depicted in FIG. 15, the cap 712 includes a recessed center portion 713, the poppet neck 718 is elongated compared to poppet neck 318, and the platform 714 is taller and its perimeter sits closer to the flow path 726 than the platform 314.

Figure 21:
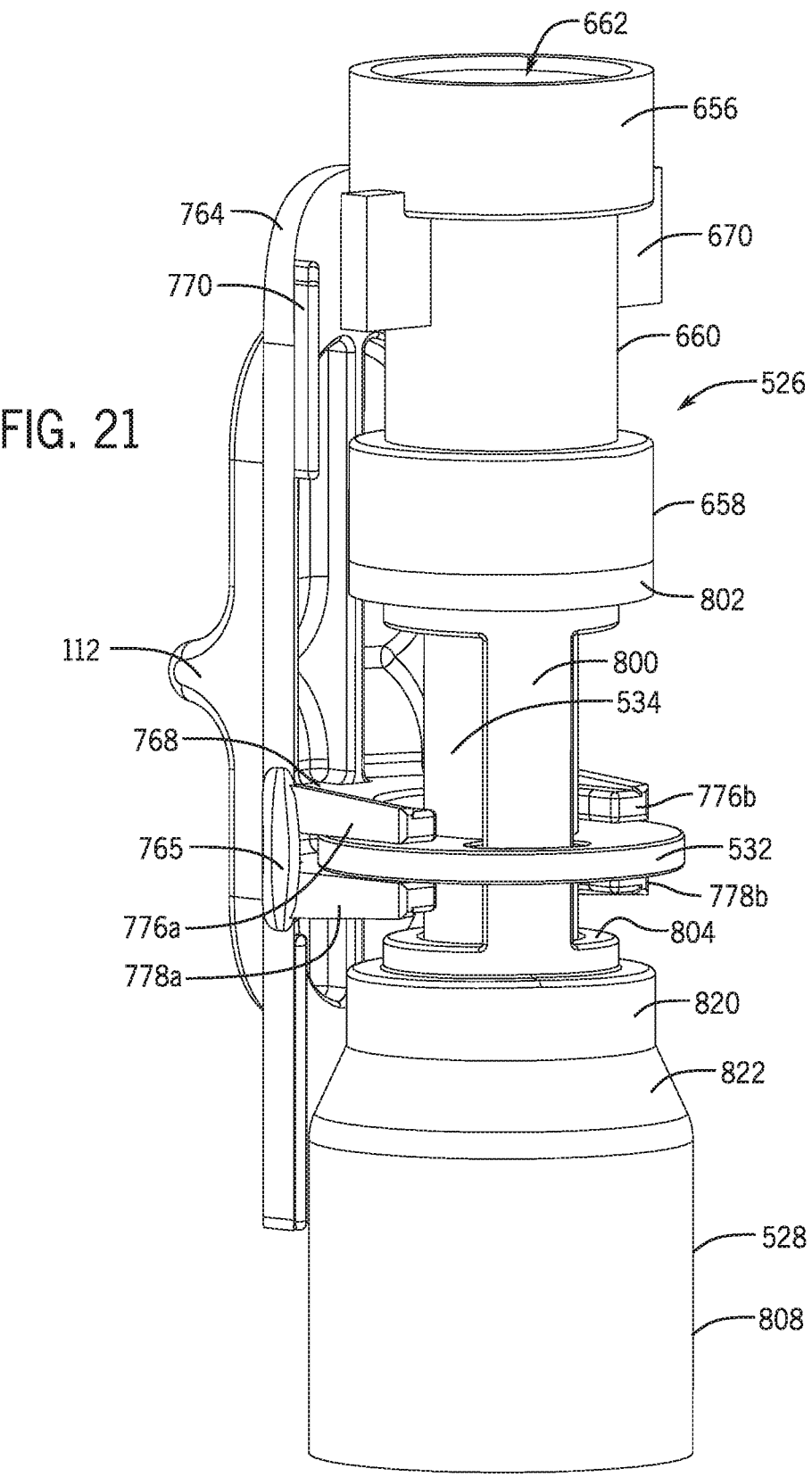
FIG. 21 is a right rear isometric view of a pause valve assembly of the handle of FIG. 18.

With reference to FIG. 21, a retaining ring 532 may be substantially the same in its design and operation as the retaining ring 132 described above.

With further reference to FIG. 21, a pause actuator 512 may be substantially the same in its design and operation as the pause actuator 112 described above. In the example depicted in FIG. 21, and compared to the example depicted in FIGS. 9-10, the interior slider plate 764 may include a lateral tab 765 on each lateral side of the plate 764 adjacent the first and second upper and lower prongs 776a, 776b, 778a, 778b.

Figure 27:
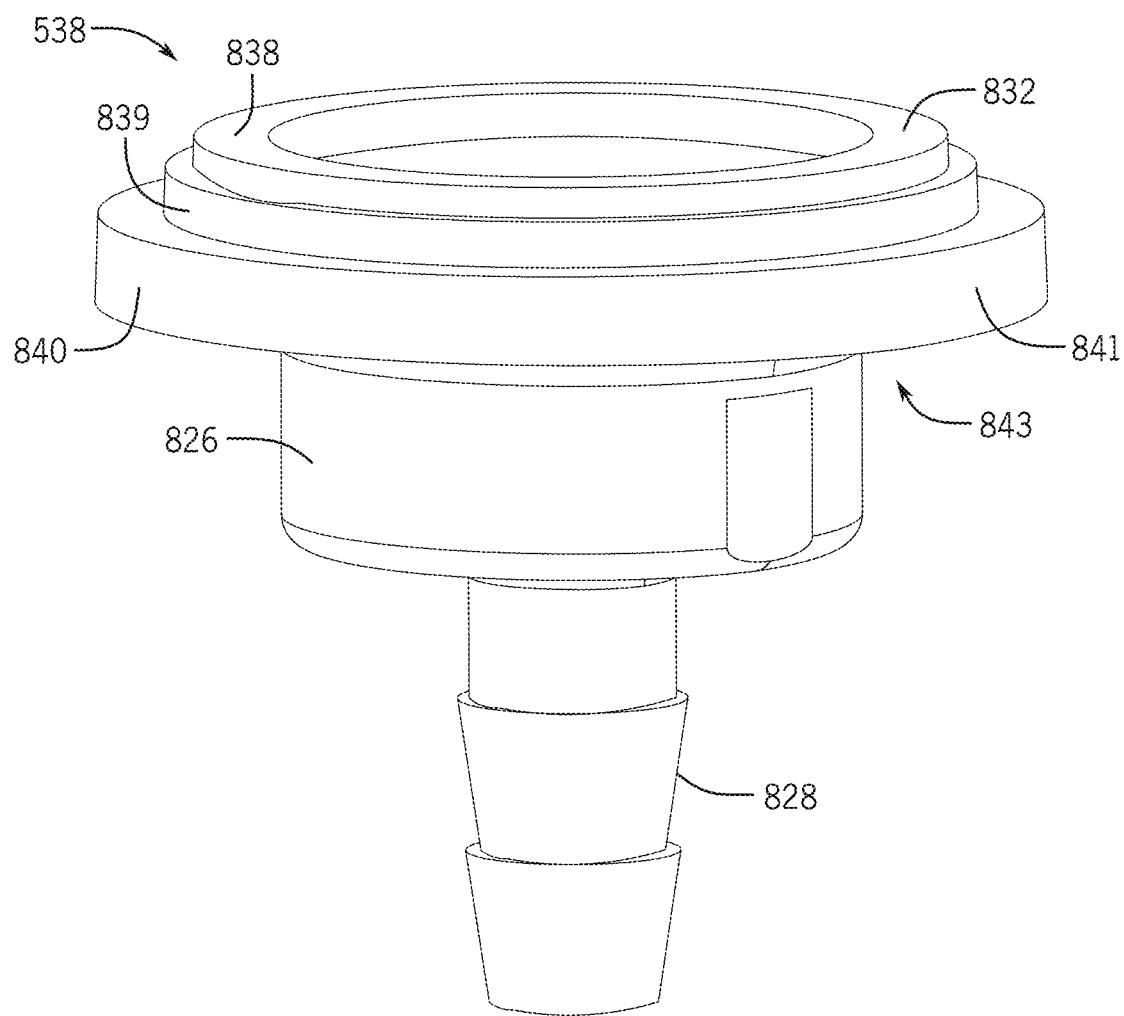
FIG. 27 is a front isometric view of a valve base of the handle of FIG. 18.

With reference to FIGS. 18, 19, and 27, a swivel assembly 843 may include a valve base 538. In the example depicted in FIG. 27, and compared to the example depicted in FIG. 17, the swivel assembly 843 may not include a bushing 140. Also in the example depicted in FIG. 27, and compared to the example depicted in FIG. 17, the valve base 538 may include a series of stacked, concentric, annular discs instead of an annular protruding rim 424. The top disc 838 may have the smallest diameter of the stack with the middle disc 839 having a diameter between the top disc 838 and the bottom disc 840. The thickness of each of the discs 838, 839, 840 may increase between each disc, with the top disc 838 having the smallest thickness, the middle disc 839 having a thickness between the two discs 838, 840, and the bottom disc 840 having the greatest thickness. Compared to the example depicted in FIG. 17, the example of FIG. 27 may not include any threads 434.

When the handle 500 is assembled, the handle components of FIGS. 18-27 may be assembled within the housing 502 similarly to how the handle 100 is assembled, except as described below.

Compared to the assembled components of FIGS. 3-5B and 7A-17 of handle 100, the assembled components of FIGS. 18-27 of handle 500 may occupy a greater portion of the cavity 572 as measured along a longitudinal axis of the handle 500. The barbed tip 828 may terminate lower in the cavity 572 than the barbed tip 428 of the first-described handle 100.

The rim 620 of the valve cap 522 may be captured between the underside of the second ledge 552a, 552b of the first and second shells 514, 516 and the top surface of the head 656 of the upper valve body 526. The lower end 624 of the valve cap 522 may be received in the portion of the valve cavity 662 of the upper valve body 526 adjacent the head 656. The lower end 624 may be positioned above and adjacent to a sealing member 520b seated on the shelf 674 of the upper valve body 526. The arms 670 may extend laterally to a vertical support wall 548a, 548b and be positioned adjacent to and under the third ledges 554a, 554b.

The exterior wall 694 of the shuttle retainer 530 may be positioned adjacent to the inner skirt wall 816 of the lower valve body 528 such that the stepped profile of the exterior wall 694 follows the stepped profile of the inner skirt wall 816. Compared to the assembly of the shuttle retainer 130 and the lower valve body 128 of the handle 100 of the first-described embodiment, the top surface 700 of the shuttle retainer 530 may be positioned adjacent to the upper portion 822 of the skirt 808 but may not extend to the annular wall 820 and may not extend to the sealing member 520d adjacent the annual wall 820 or lower plate 804.

Compared to the assembly of the shuttle retainer 130 and shuttle valve 134 of the handle 100, a greater portion of the body 732 of the shuttle valve 534 may be received in the cavity 698 of the shuttle retainer 530. The shuttle compartment 684 formed in the space between the bottom surface 682 of the floor 672 of the head 656 of the upper valve body 526 and the top surface 744 of the body 732 of the shuttle valve 534 when the handle 500 is in pause mode may be longer than or have a greater volume than the shuttle compartment 284 of the handle 100.

The walls 770 on the rear face 768 of the interior slider plate 764 of the pause actuator 512 may be positioned approximately level with the neck 660 of the upper valve body 526 when pause mode is selected and may be positioned near or adjacent the head 656 when irrigate mode is selected.

The top surface 832 of the top disc 838 of the valve base 538 may extend beneath and adjacent to the second surface 722 of the poppet support plate 716. The middle disc 839 may be positioned adjacent the inner skirt wall 816. The outer diameter of the bottom disc 840 may be approximately the same as the outer diameter of the skirt 808 of the lower valve body 528 such that when the bottom disc 840 is positioned under the skirt 808, the outer skirt wall 814 may be flush with the outer surface 841 of the bottom disc 840. When the housing 502 is assembled, the body 826 of the valve base 538 be surrounded by the eighth ledges 564a, 564b rather than by a bushing, as in the previously described handle 100.

Alternative Embodiment

FIGS. 28-36 depict another embodiment of a handle 1000. Compared to the handles 100 and 500, similarly numbered features of the components of the handle 1000 have similar designs, constructions, functions, and operations as those of the components described above unless otherwise noted. The exterior of the handle 1000 may appear the same as or similar to the handle 100 of FIGS. 1, 2A, and 2B. Compared to the handles 100, 500, in handle 1000 the poppet assembly may be integrated into the valve base to form an integrated valve base 1138. Additionally or alternatively, the handle 1000 may include a retaining clip 1130 and not include a shuttle retainer 130, 530.

Figure 28:
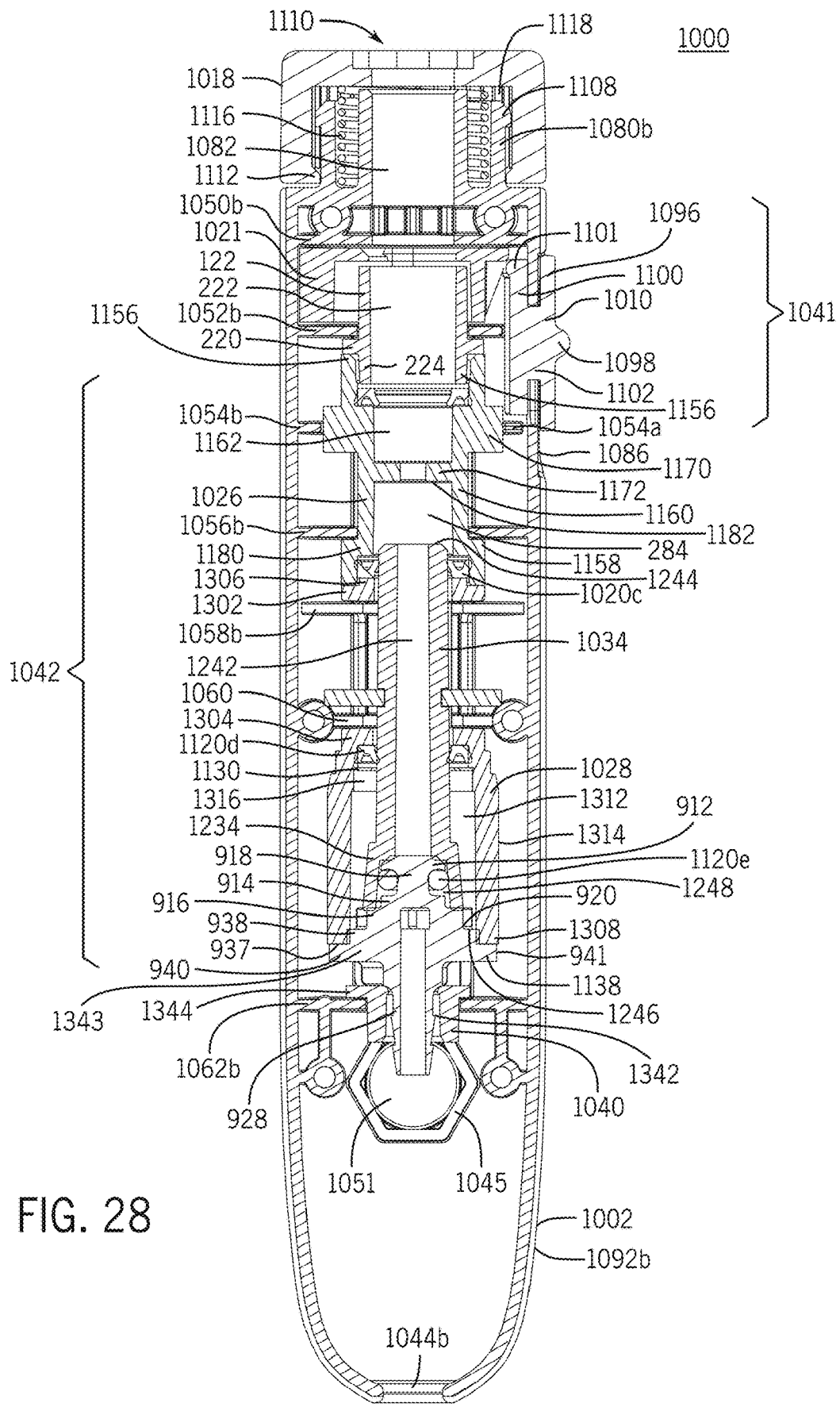
FIG. 28 is a left side elevation view in cross section of another embodiment of a handle.
Figure 29:
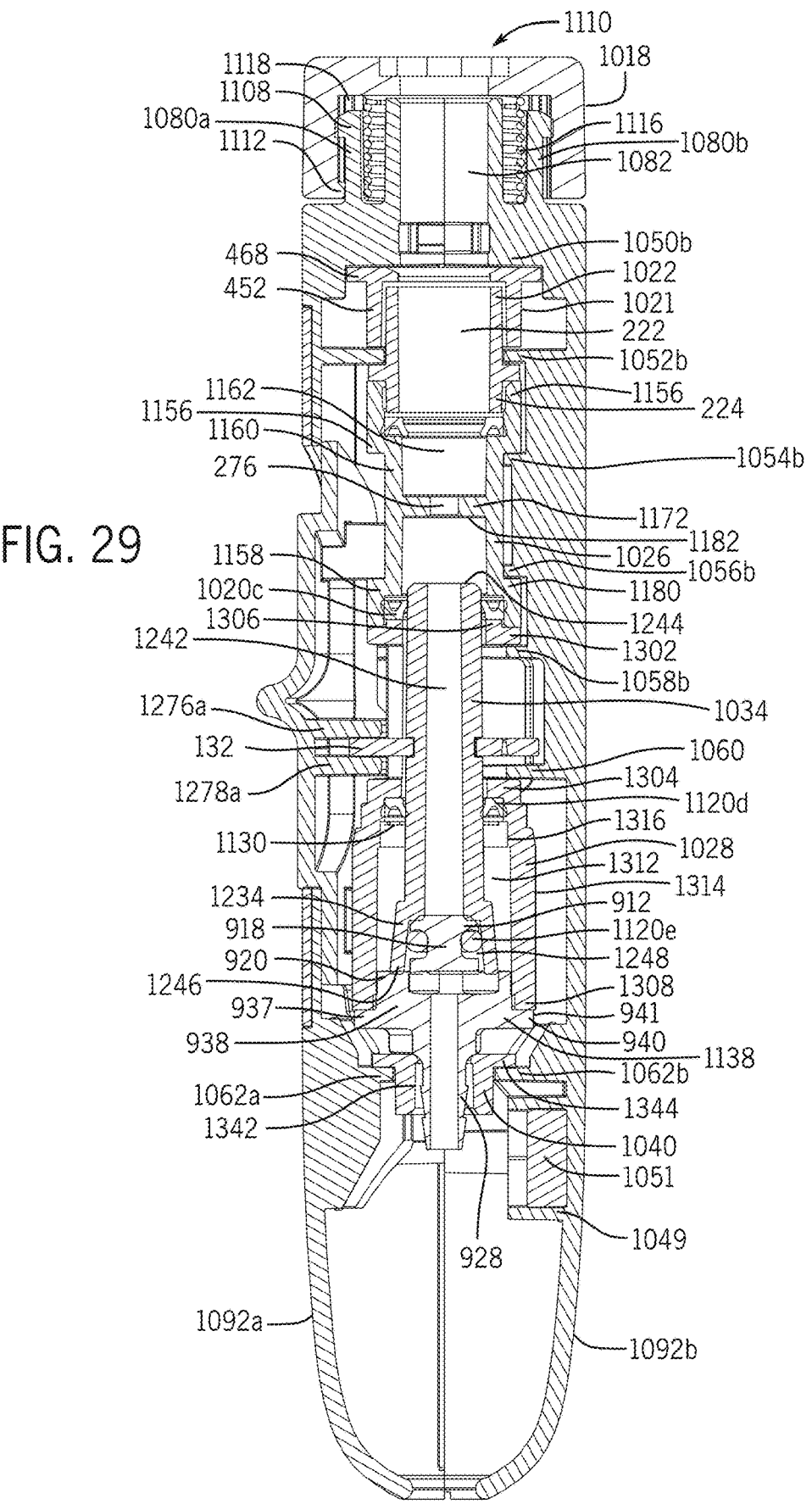
FIG. 29 is a front elevation view in cross section of the handle of FIG. 28.
Figure 30A:
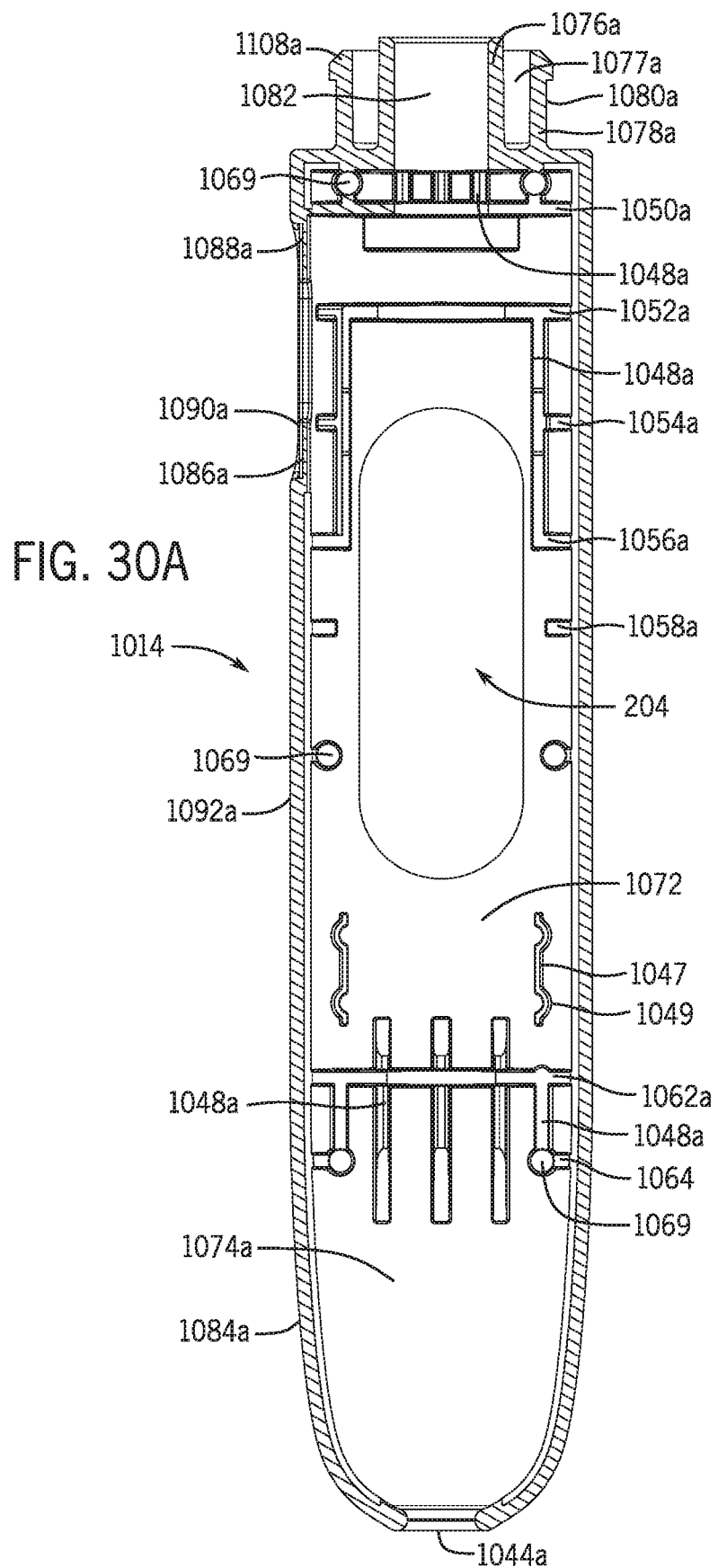
FIG. 30A is a rear elevation view of an interior of a first shell of the handle of FIG. 28.
Figure 30B:
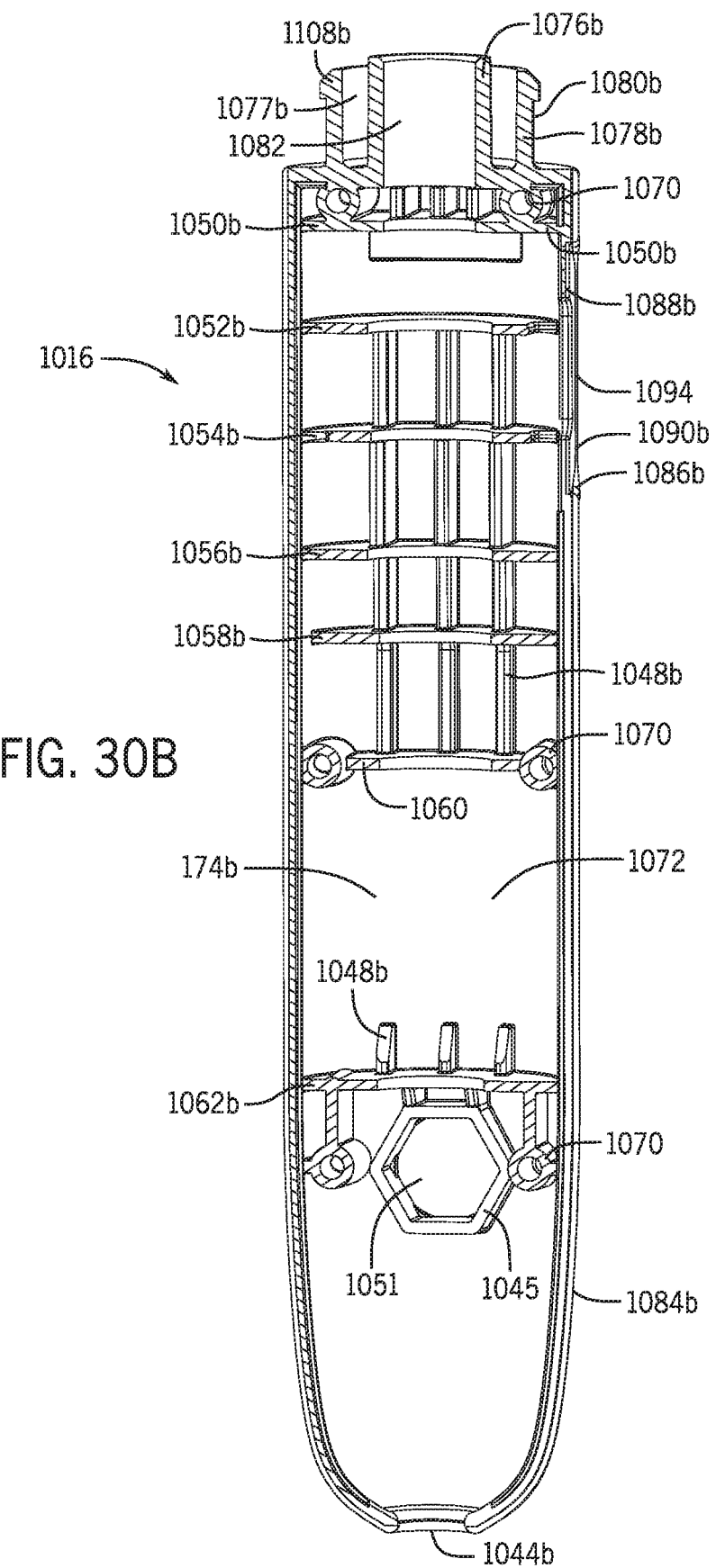
FIG. 30B is a front elevation view of an interior of a second shell of the handle of FIG. 28.

As with the handle 100 shown in FIGS. 1-17, the handle 1000 of FIGS. 28-36 may include a first shell 1014 and a second shell 1016, each comprised of a neck 1080a, 1080b and shell body 1092a, 1092b (see FIGS. 30A and 30B). The bodies 1092a, 1092b of the first and second shells 1014, 1016, respectively, together define a handle cavity 1072. The first shell 1014 may include first, second, third, fourth, fifth, seventh, and eighth ledges 1050a, 1052a, 1054a, 1056a, 1058a, 1062a, and 1064, respectively, that are constructed similarly to the previously described ledges 150a, 152a, 154a, 156a, 158a, 162a, and 164a and also have similar functions.

The first shell 1014 may also include one or more lateral brackets 1047 affixed to the interior wall 1074a that may help retain the pause actuator 1012 in the on/irrigate or paused position, as selected. Each lateral bracket 1047 may include a plurality of catches or detents 1049 that help to mechanically releasably capture the pause actuator 1012. The detents 1049 may be shaped complimentary to a portion of the pause actuator 1012. In the example depicted in FIG. 32, the detents 1049 may be semicircular in shape.

The second shell 1016 may include first, second, third, fourth, fifth, sixth, and seventh ledges 1050b, 1052b, 1054b, 1056b, 1058b, 1060, and 1062b, respectively, that are constructed similarly to the previously described ledges 150b, 152b, 154b, 156b, 158, 160, and 162b and also have similar functions.

The second shell 1016 may also include magnet 1051 and a magnet retainer 1045 for securing the magnet 1051. The magnet 1051 may help connect the handle 1000 to the base unit via a corresponding magnet in the base unit as described in U.S. patent application Ser. No. 15/843,911 entitled "Oral irrigator with magnetic attachment" filed contemporaneously herewith and which is incorporated by reference herein in its entirety.

The bodies 1092a, 1092b of the first and second shells 1014, 1016 may also include a plurality of vertical support walls 1048a, 1048b, pegs 1069, and holes 1070 similar to the corresponding features of the first-described embodiment.

With reference to FIGS. 28, 30A, and 30B, the outer surface of the exterior walls 1084a, 1084b of the first and second shells 1014, 1016 may each define a C-shaped depression 1086a, 1086b with respective upper surfaces 1088a, 1088b and lower surfaces 1090a, 1090b similar to the corresponding features described above. When the handle 1000 is assembled, opposing depressions 1086a, 1086b define a pocket 1086 surrounding an opening 1094. An elongate tip eject button 1010 may be formed with an exterior slider portion 1096 and an interior slider portion 1100 that are separated from each other by a neck 1102. The exterior slider portion 1096 may include a tab grip 1098. The interior slider portion 1100 may include a nose 1101 that projects radially inward therefrom. The design and construction of the tip eject button 1010, and its position relative the first and second shells 1014, 1016 may be the same as or similar to the tip eject button 110 of the first-described embodiment.

With reference again to FIGS. 30A and 30B, the body 1092a, 1092b of each of the first and second shell 1014, 1016 may terminate in a semicircular hose cut-out 1044a, 1044b. When the first and second shells 1014, 1016 are assembled, the cut-outs 1044a, 1044b together define a substantially circular aperture through which a hose passes.

The neck 1080a, 1080b of each of the first and second shells 1014, 1016, respectively, includes an interior wall 1076a, 1076b, an exterior wall 1078a, 1078b, and an annular recess 1077a, 1077b substantially as described above. The exterior walls 1078a, 1078b may include a lip 1108a, 1108b and the interior walls 1076a, 1076b, when assembled into the handle 1000, define a cylindrical tip cavity 1082 configured to receive a tip 104.

The handle 1000 may include a handle collar 1018 having similar features and functions to the handle collar 118 described above. The handle collar 1018 may include a tip-receiving aperture 1110 for receiving the tip 104, an annular well 1118 for receiving a spring 1116, and arcuate tabs 1112 for securing the collar 1018 onto the first and second shells 1014, 1016 (see FIG. 28).

With reference to FIGS. 28 and 29, a tip eject mechanism 1041 of the handle 1000 may be substantially the same in its design and operation as the tip eject mechanism 141 described above and may include a cylindrical valve cap 1022, a latch 1021, and a tip eject button 1010.

Figure 31:
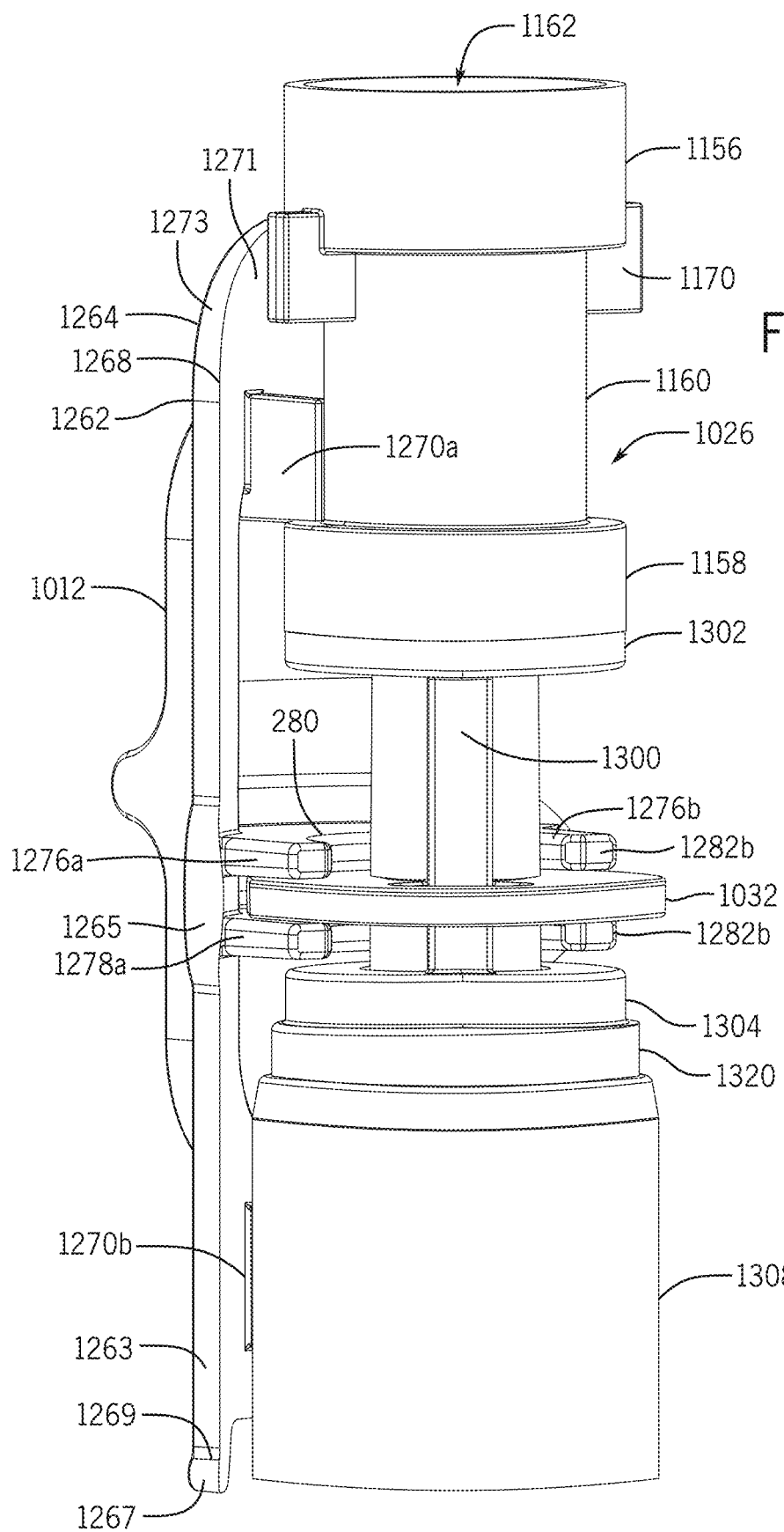
FIG. 31 is a right rear isometric view of a pause valve assembly of the handle of FIG. 28.

With reference to FIGS. 28, 29, and 31, a pause valve assembly 1042 of the handle 1000 may include an upper valve body 1026, a lower valve body 1028, a shuttle valve 1034, and a pause actuator 1012 operably connected to the shuttle valve 1034 by a retaining ring 1032 substantially the same as the pause valve assembly 142, 542 described above with the following exceptions. The pause valve assembly 1042 may include a retaining clip 1130 but not include a shuttle retainer 130. The pause valve assembly 1042 may include an integrated valve base 1138 having a poppet assembly 1136 connected to an elongated barbed tip 928.

With continued reference to FIGS. 28 and 29, an upper valve body 1026 may be substantially the same as the upper valve body 526 described above for handle 500.

Figure 33:
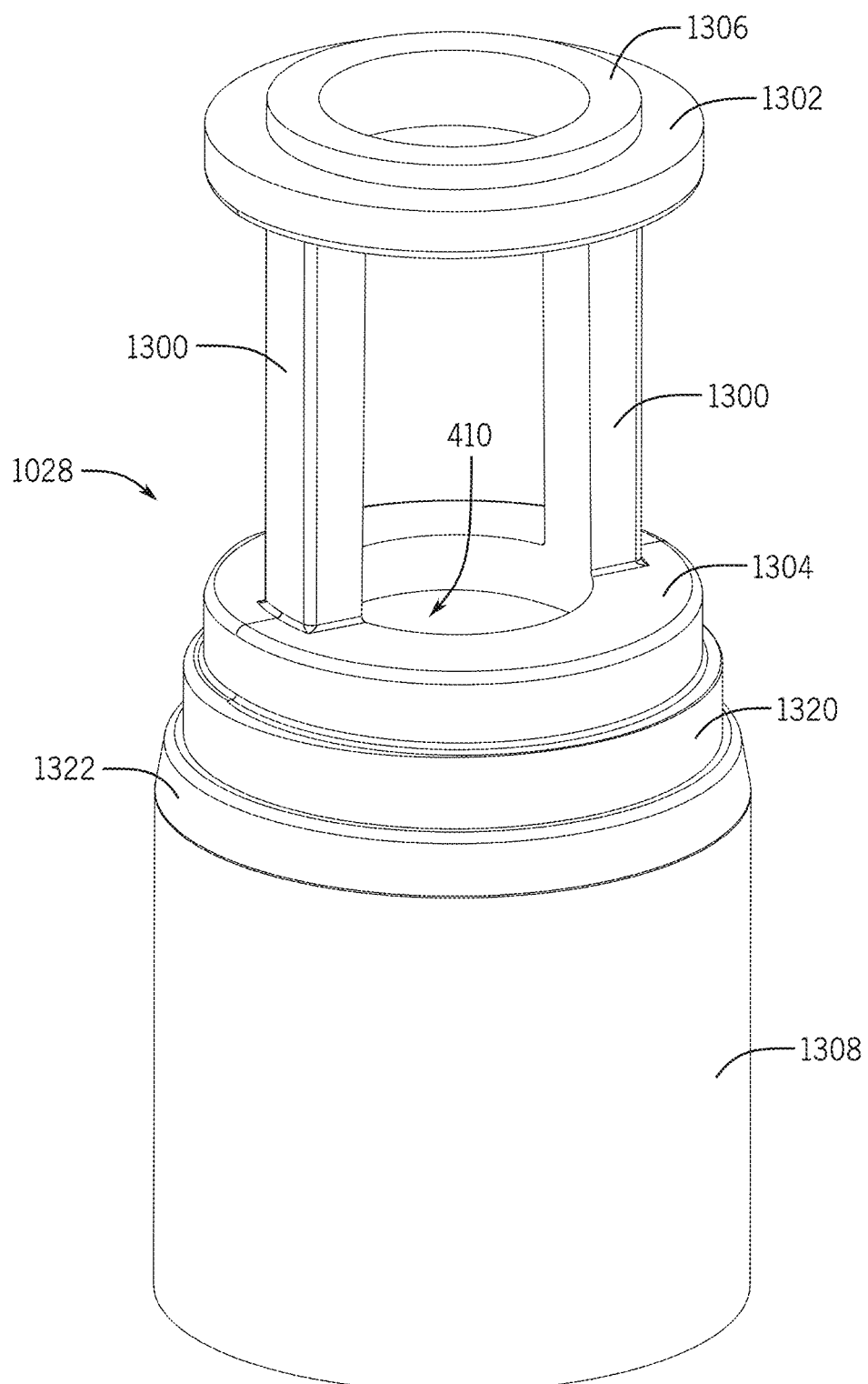
FIG. 33 is top front isometric view of a lower valve body of the pause valve assembly of FIG. 31.

With reference to FIGS. 28, 29, and 33, a lower valve body 1028 may be substantially the same as the lower valve body 128 described above. The lower valve body 1028 includes an annular wall 1320 positioned between the lower plate 1304 and the skirt 1308. The upper portion 1322 of the skirt 1308 may angle inwards towards the annular wall 1320. The external diameter of the upper plate 1302 may be approximately equal to the external diameter of the lower plate 1304, and both diameters may be greater than the external diameter of the lip 1306 but less than the external diameter of the annular wall 1320 and the skirt 1308. In the example depicted in FIG. 33, and compared to the example depicted in FIGS. 12A and 12B, the arms 1300 may be elongated, and the lower valve body 1028 may include an annular wall 1320 and an angled upper portion 1322 of the skirt 1308 may be truncated.

A sealing member 1120d, such as a U-cup, may be positioned under the lower plate 1304 adjacent the annual wall 1320. The sealing member 1120d may be overmolded into the lower plate 1304 or the annual wall 1320.

Figure 32:
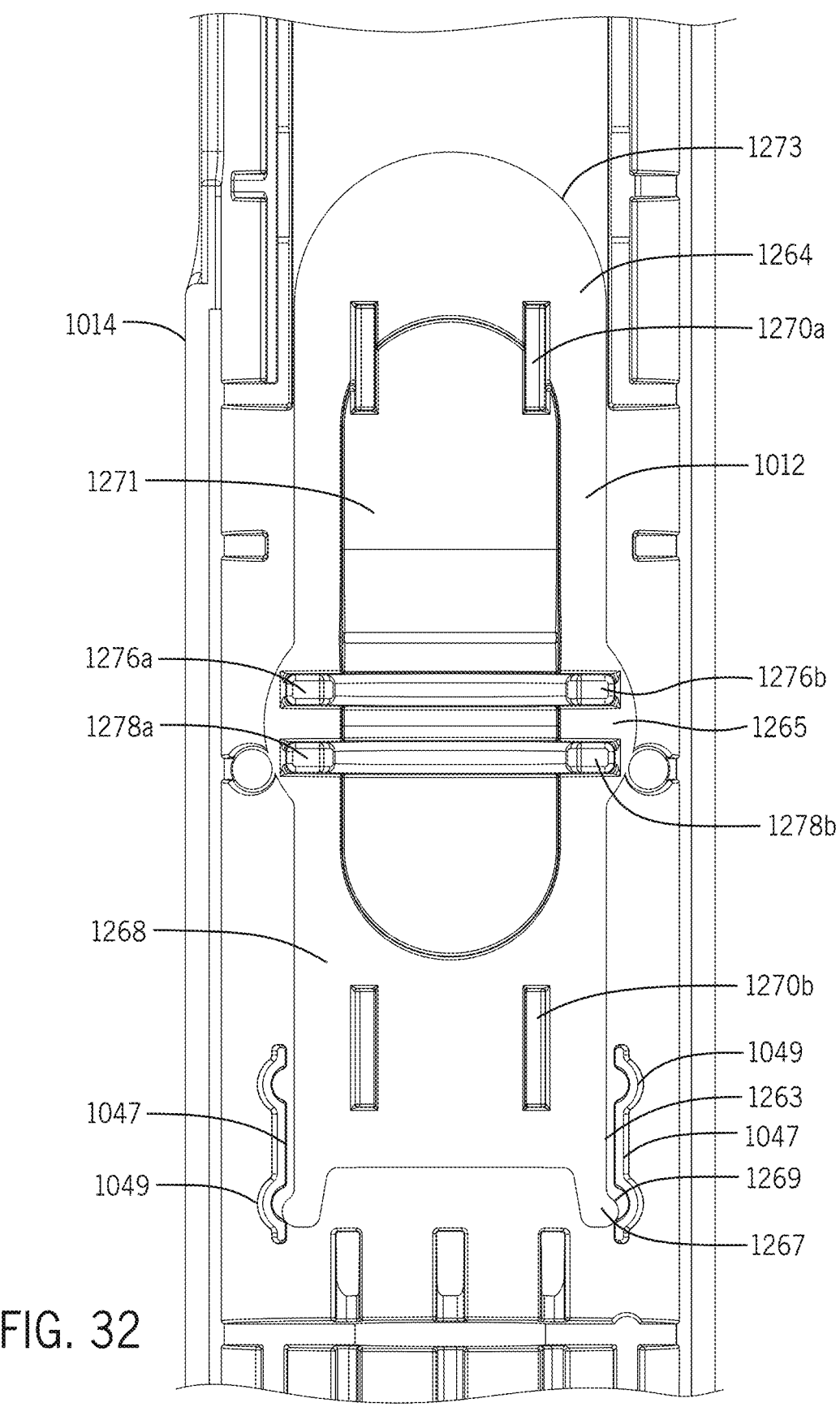
FIG. 32 is a rear isometric view of the first shell of the handle of FIG. 28 and a portion of the pause valve assembly of FIG. 31.

With reference to FIGS. 31 and 32, a pause actuator 1012 may be substantially the same in its design and operation as the pause actuators 112, 512 described above. In the example depicted in FIGS. 31 and 32, the interior slider plate 1264 may include a lateral tab 1265 on each lateral side of the plate 1264 adjacent the first and second upper and lower prongs 1276a, 1276b, 1278a, 1278b similar to the example depicted in FIG. 21.

Each lateral side of a lower end 1263 of the interior slider plate 1264 may terminate in a foot 1267 that may help the pause actuator 1012 be retained in the on/irrigate or paused position, as selected. Each foot 1267 may be received in a complimentarily shaped detent 1049 of the lateral bracket 1047 affixed to the interior wall 1074a of the first shell 1014. Each foot 1267 may include a sloped upper surface 1269 that helps the foot 1267 slide smoothly between detents 1049 as the pause actuator 1012 is moved between the irrigate and pause positions.

The interior slider plate 1264 may have a generally concave shape and may include a rear face 1268 that is contoured or molded to form an internal face 1271 of the exterior slider plate 1262. One or more walls 1270 may extend from the rear face 1268 and may help the pause actuator 1012 maintain a contact with and constant spacing from other components of the pause valve assembly 1042.

For example, two walls 1270a are shown positioned toward an upper end 1273 of the interior slider plate 1264 and two walls 1270b are shown positioned toward a lower end 1263. The upper walls 1270a may interface with the upper valve body 1026 and the lower walls 1270b may interface with the lower valve body 1028.

With reference to FIG. 31, a retaining ring 1032 may be substantially the same in its design and operation as the retaining ring 132 described above.

Figure 34:
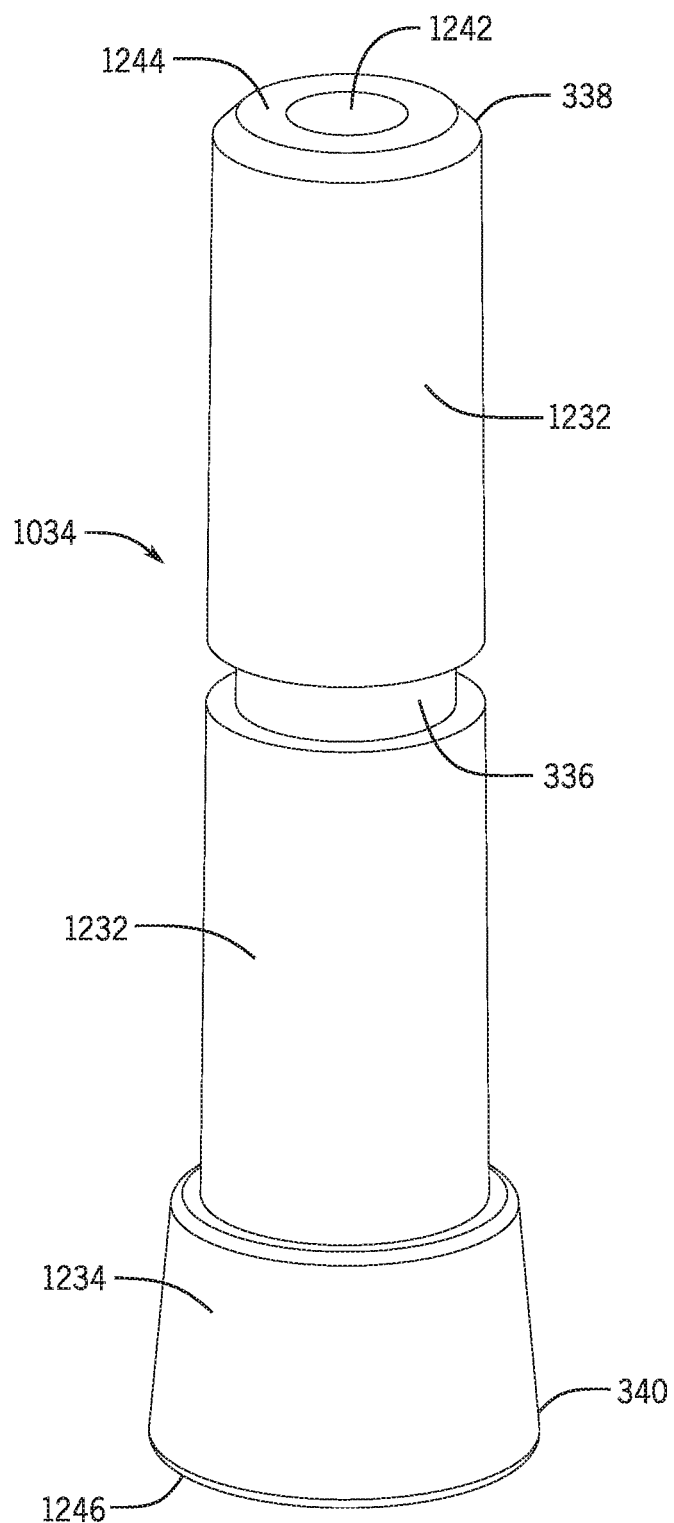
FIG. 34 is an isometric view of a shuttle valve of the pause valve assembly of FIG. 31.

With reference to FIG. 34, the shuttle valve 1034 may have substantially the same features as the shuttle valve 134 descripted above. In the example depicted in FIG. 34, the body 1232 is elongated compared to the body 332 of the shuttle valve 134 depicted in FIG. 14.

Figure 35:
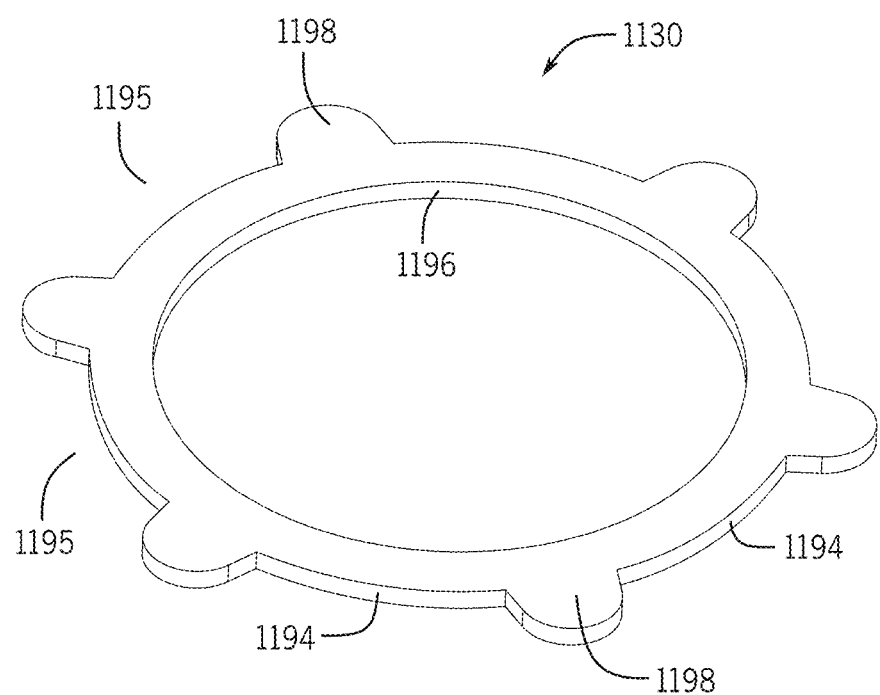
FIG. 35 is an isometric view of a retaining clip of the pause valve assembly of FIG. 31.

With reference to FIGS. 28, 29, and 35, the pause valve assembly 1042 may include a retaining clip 1130 and not include a shuttle retainer 130, 530. Compared to a shuttle retainer 130, 530 the retaining clip 1130 may permit a reduction in the size, including the diameter, of the lower valve body 1028 in which the clip 1130 is received. With reference to FIG. 35, the retaining clip 1130 may be annular in shape with an interior wall 1196 that defines an aperture and an exterior wall 1194 from which a plurality of spokes 1198 extend radially. In one example, the retaining clip 1130 is a star washer. The retaining clip 1130 frictionally engages the inner wall of the lower valve body 1028 and retains the sealing member 1120d in place within the shuttle valve 1034.

With reference to FIGS. 28 and 29, when the pause valve assembly 1042 is assembled, the retaining clip 1130 may be received in the skirt cavity 1312 of the lower valve body 1028 such that the spokes 1198 of the clip 1130 are adjacent the inner skirt wall 1316. The retaining clip 1130 may be positioned proximate to the annular wall 1320 of the lower valve body 1028 and below the sealing member 1120d positioned under the lower plate 1304 of the lower valve body 1028. The inner diameter of the retaining clip 1130 may be slightly larger than the outer diameter of the shuttle valve 1034 to permit the shuttle valve 1034 to travel axially within the aperture of the retaining clip 1130. Water may reach the sealing member 1120d through both the inner diameter of the retaining clip 1130 and the fluid flow path 1195 between spokes 1198 and the inner diameter of the annular wall 1320 of the lower valve body 1028 and press the sealing member 1120d against the shuttle valve 1034 and the lower plate 1304 more uniformly, thereby creating a faster or stronger seal against the shuttle valve 1034 than in the absence of water.

Compared to embodiments that include a shuttle retainer 130, 530, when the pause valve assembly 1042 includes a retaining clip 1130, the base 1234 and a lower portion of the body 1232 of the shuttle valve 1034 may be received in the skirt cavity 1312 of the lower valve body 1028 instead of in the cavity 298, 698 of the shuttle retainer 130, 530. When fluid flows into the handle 1000 during either irrigate mode or pause mode, it flows into the skirt cavity 1312 of the lower valve body 1028 instead of the cavity 298, 698 of the shuttle retainer 130, 530.

During irrigate mode, when the pause valve assembly 1042 is placed in an on or open position and the shuttle valve 1034 is positioned towards the handle collar 1018, the shuttle valve 1034 may be blocked from advancing too far by contact between the top surface 1244 of the shuttle valve 1034 and the bottom surface 1182 of the floor 1172 of the head 1156 of upper valve body 1026.

Figure 15:
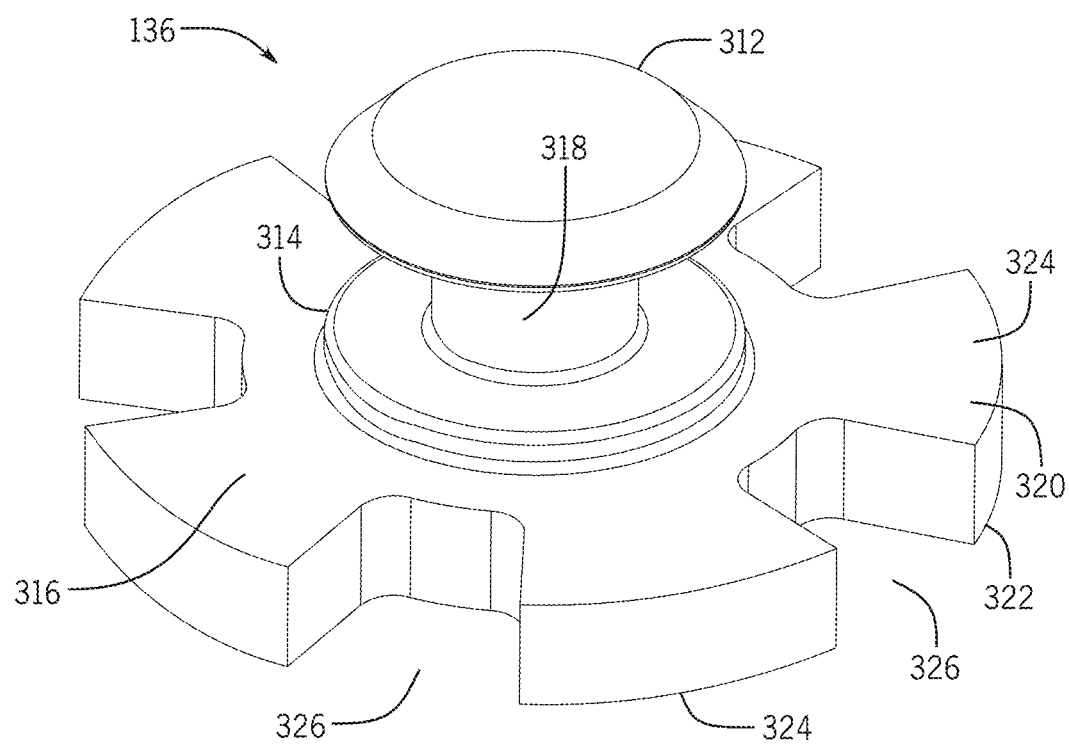
FIG. 15 is a front top isometric view of a poppet assembly of the pause valve assembly of FIG. 9A.
Figure 17:
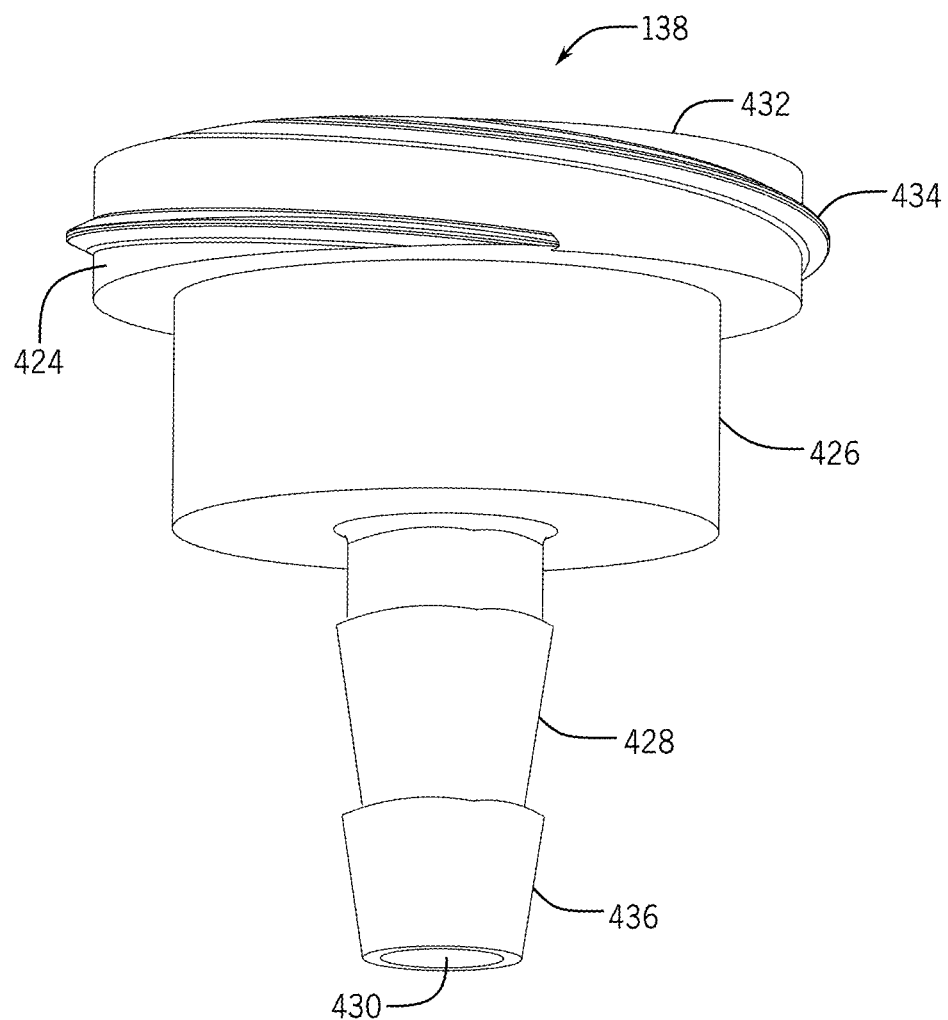
FIG. 17 is a front isometric view of a valve base of the handle of FIG. 4.
Figure 36A:
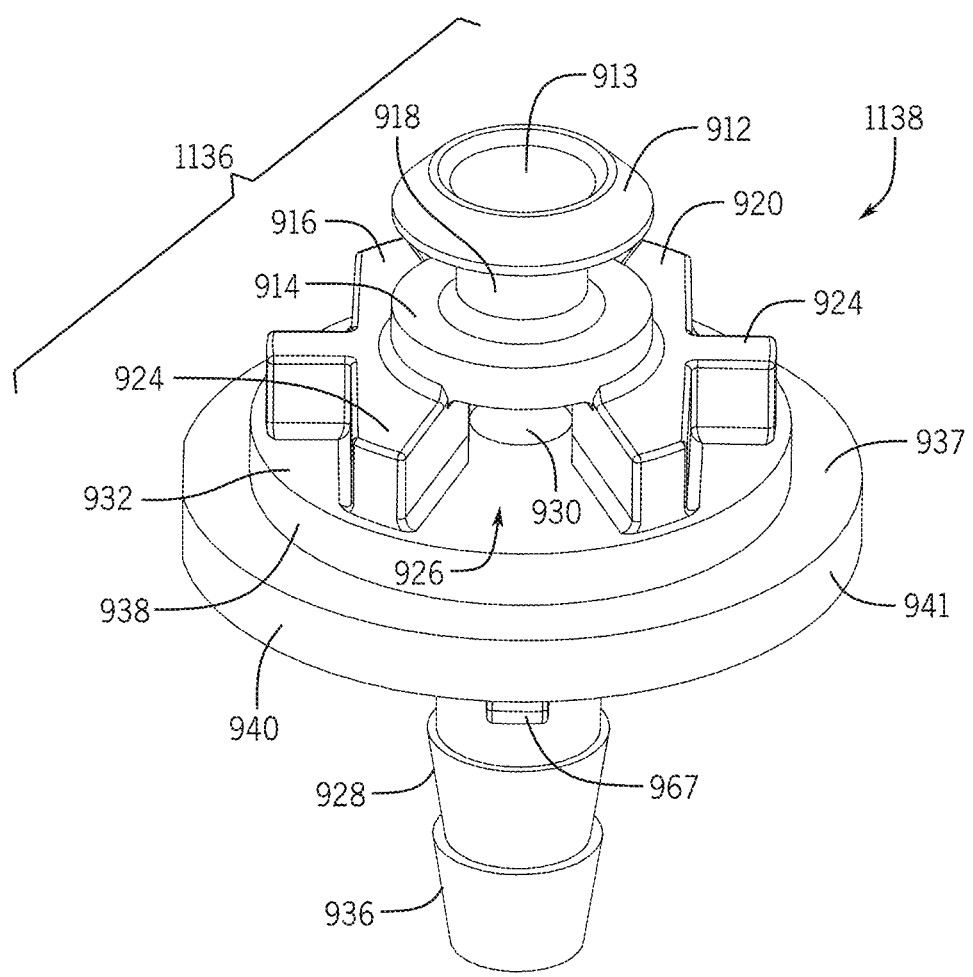
FIG. 36A is front top isometric view of an integrated valve base of the handle of FIG. 28.
Figure 36B:
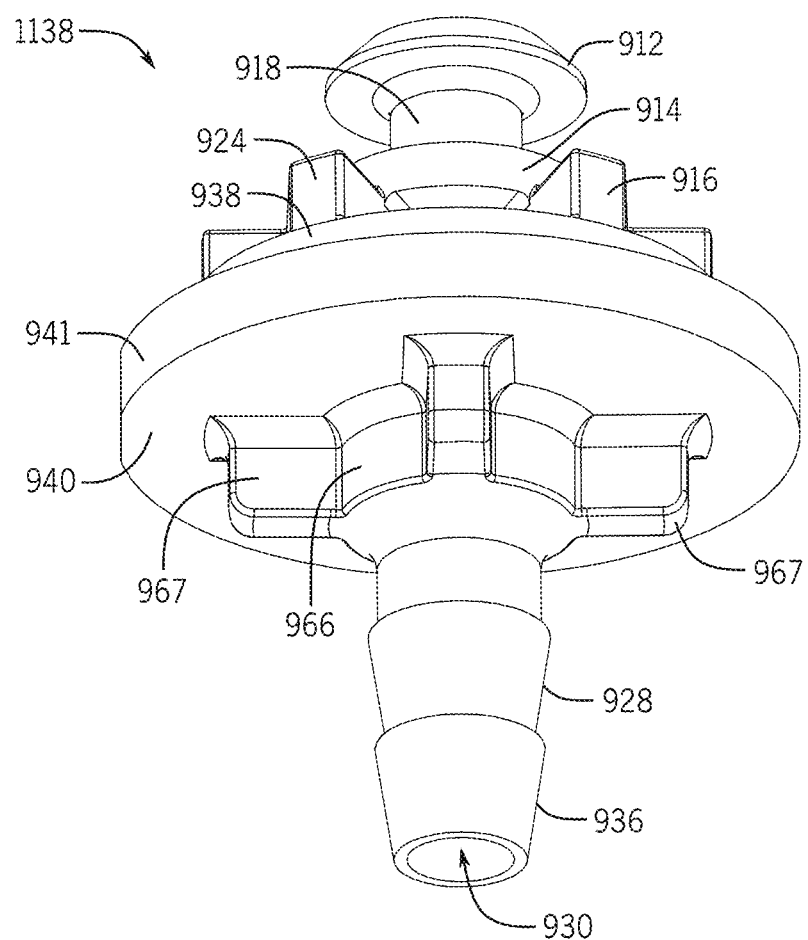
FIG. 36B is front bottom isometric view of the integrated valve base of FIG. 36A.

Compared to the poppet assembly 136 and valve base 138 of FIGS. 15 and 17, and with reference to FIGS. 36A and 36B, the poppet assembly is incorporated into the valve base to form an integrated valve base 1138, which may help decrease handle 1000 manufacturing costs and/or assembly time by reducing the number of component parts. Handles 1000 that include an integrated valve base 1138 have a similar design, construction, function, assembly, and operation as those described above with the following exceptions.

The integrated valve base 1138 is configured to selectively disconnect fluid flow from the hose 108 to the tip 104. The integrated valve base 1138 may include a poppet assembly 1136 connected to an elongated barbed tip 928 by stacked concentric upper and bottom discs 938, 940. The poppet assembly 1136 may include a cap 912, including a recessed center portion 913, connected to a poppet support plate 916 by a poppet neck 918. An annular platform 914 may encircle the neck 918 above the poppet support plate 916. The cap 912 and annular platform 914 are generally sized and shaped to be received in the shuttle valve 1034. The poppet support plate 916 includes an upper surface 920 and a plurality of support features 924 extending outwardly from the platform 914. A flow path 926 may be defined between two adjacent but spatially separated support features 924. A sealing member 1120e may be seated around the poppet neck 918 between the cap 912 and platform 914.

The upper disc 938 may have a smaller diameter than the bottom disc 940 such that a first surface 937 of the bottom disc 940 is exposed and is available to interface with the skirt 1308 of the lower valve body 1028.

A reinforced base 966 positioned between the bottom disc 940 and the barbed tip 928 may include a plurality of radially extending arms 967 for stability when seated against the bushing 1040. The barb aperture 1342 defined within the bushing 1040 is of larger diameter than the barbed tip 928 of the integrated valve base 1138, allowing the hose to fit thereon.

The integrated valve base 1138 defines a flow cavity 930 from the barbed tip 928 through to the top surface 932 of the upper disc 938. The barbed tip 928 may include one or more gripping components 936 that enhance the connection between the integrated valve base 1138 and the hose 108.

During irrigate mode, fluid can flow from the hose 108 through the flow cavity 930 in the integrated valve base 1138, through the flow path 926 between support features 924 of the poppet support plate 916, into the skirt cavity 1312 of the lower valve body 1028, into the base cavity 1248 of the shuttle valve 1034, and into the flow lumen 1242 of the shuttle valve 1034.

When the handle 1000 is assembled, the handle components of FIGS. 28-36 may be assembled within the housing 1002 similarly to how the handle 500 is assembled, except as described below.

With reference to FIG. 28, and compared to the example in FIG. 18, the arms 1170 of the valve cap 1022 may be positioned adjacent to the third ledges 1054a, 1054b rather than under the third ledges 554a, 554b.

With further reference to FIG. 28, and compared to the example in FIG. 18, the lip 1180 of upper valve body 1026 may be positioned under the fourth ledge 1056a, 1056b rather than above the fourth ledge 556a, 556b. The sealing member 1020c may be positioned under the lip 1180, adjacent to the base 1158 of the upper valve body 1026, and above the lip 1306 of the lower valve body 1028. The upper plate 1302 of the lower valve body 1028 may be positioned above and adjacent the fifth ledge 1058a, 1058b.

As described above, and with reference to FIGS. 28 and 29, the retaining clip 1130 may be positioned proximate to the annular wall 1320 of the lower valve body 1028 and below the sealing member 1120*d* positioned under the lower plate 1304 of the lower valve body 1028.

As shown in FIGS. 28 and 29, and similarly to FIGS. 4-5B for handle 100, the barbed tip 928 of the integrated valve base 1138 is received in the barb aperture 1342 of the bushing 1040. The rim 1344 of the bushing 1040 may be positioned on top of the seventh ledges 1062*a*, 1062*b*.

The walls 1270*a* on the rear face 1268 of the interior slider plate 1264 of the pause actuator 1012 may be positioned near the interface between the neck 1160 and base 1158 of the upper valve body 1026 when pause mode is selected and may be positioned near or adjacent the head 1156 when irrigate mode is selected.

When the handle 1000 is assembled, the cap 912, poppet neck 918, and annular platform 914 of the poppet assembly 1136 and the sealing member 1120*e* positioned around the poppet neck 918 may be received in the base cavity 1248 of the shuttle valve 1034. The first surface 920 of the poppet support plate 916 may be positioned below and adjacent to the bottom surface 1246 of the base 1234 of the shuttle valve 1034.

The poppet support plate 916 and upper disc 938 of the integrated valve base 1138 are received in the skirt cavity 1312 of the lower valve body 1028. The outer diameter of the bottom disc 940 of the integrated valve base 1138 may be approximately the same as the outer diameter of the skirt 1308 of the lower valve body 1028 such that when the first surface 937 of the bottom disc 940 is positioned under the skirt 1308, the outer skirt wall 1314 may be flush with an outer surface 941 of the bottom disc 940.

To connect the pause valve assembly 1042 and the swivel assembly 1343, the barbed tip 928 of the integrated valve base 1138 is received in the barb aperture 1342 of the bushing 1040. A rim 1344 of the bushing 1040 may rest on the seventh ledges 1062*a*, 1062*b*. The bushing 1040 may freely rotate on the seventh ledges 1062*a*, 1062*b* to allow the integrated valve base 1138 and connected valve assembly to freely rotate or swivel within the handle 1000.

Insertion and Ejection of a Tip

A user may insert a tip 104 into, and eject a tip 104 from, the handle 100 of FIGS. 1-17 according to the following procedures. Insertion and ejection of a tip 104 from the handle 500 of FIGS. 18-27 and from the handle 1000 of FIGS. 28-36 follows a similar procedure. The procedures are substantially the same as those described in U.S. patent application Ser. No. 14/555,339, which is incorporated by reference in its entirety herein.

A tip 104 is inserted into the handle 100 by passing an end of the tip 104 opposite the tip outlet 105 through the tip-receiving aperture 210 of the handle collar 118, through the tip receiving cavity 182 defined by the interior walls 174*a*, 174*b* of the first and second shells 114, 116, and into the tip-receiving aperture 474 of the latch body 452. Before the tip 104 enters the handle 100, the tip-receiving aperture 474 of the latch body 452 is partially offset from the tip cavity 222 of the valve cap 122, which is positioned below the tip-receiving aperture 474. The tip 104 engages the latch body 452 and pushes the interior lip 470 of the latch body 452 laterally in the direction of the spring legs 454 until the tip-receiving aperture 474 of the latch body 452 and the tip cavity 222 of the valve cap 122 vertically align. The spring legs 454 are compressed, and the feet 462 are positioned adjacent to the interior wall 174*a*, 174*b* of the first and second shells 114, 116.

The inserted end of the tip 104 can then proceed through the tip cavity 222 of the valve cap 122, past the sealing member 120*b*, and into the valve cavity 246 of the backflow valve body 124 or the valve cavity 662 of the upper valve body 526. A tip collar 106 on the tip 104 may be biased against the handle collar 118 when the tip 104 is fully inserted into the handle 100. The outer diameter of the inserted end of the tip 104 is slightly larger than the inner diameter of the sealing member 120*b*, thereby creating a fluid-tight seal between the sealing member 120*b* and the tip 104. The D-shape of the perimeter of the interior lip 470 of the latch body 452, which may be complimentary or keyed to the D-shape of the inserted end of the tip 104, help to align the tip 104 in the handle 100. The tip 104 may be coupled to the latch 121 by capturing the interior lip 470 of the latch body 452 within an annular recess (not shown) of the tip 104.

The handle collar 118 of the handle 100 is depressed toward the bodies 192*a*, 192*b* of the first and second shells 114, 116 when the tip 104 is coupled with the latch 121. As the handle collar 118 is depressed, the arcuate tabs 212 of the handle collar 118 move along the necks 180*a*, 180*b* of the first and second shells 114, 116 toward the bodies 192*a*, 192*b*, which decreases the height of the gap 214, and the spring 216 is compressed. The compressed spring 216 exerts an upward force, which will return the handle collar 118 back to its original position (i.e., separated from the bodies 192*a*, 192*b* by a gap 214) in the absence of another force opposing this upward force. When the tip 104 is coupled with the latch 121, this upward force will be opposed by a flange (not shown) on the tip 104 that holds the handle collar 118 down, thereby maintaining the handle collar 118 in a position adjacent to the handle housing 102.

An audible click or other similar noise may occur when the latch 121 captures the annular recess of the tip 104, thereby providing an audible indication that the tip 104 is attached to the handle 100. The noise may be mechanically produced (for example, a click resulting from a portion of the tip 104 impacting a portion of the handle 100, or a click resulting from a portion of the tip 104 springing outward or mechanically deforming).

In another example of inserting a tip 104, a user slides the exterior slider portion 196 of the tip eject button 110 upward toward the handle collar 118 of the handle 100, and maintains the exterior slider portion 196 in that position while inserting a tip 104 into the handle 100 as described above. Sliding the exterior slider portion 196 upward along the longitudinal axis of the handle housing also slides the interior slider portion 200 upwards via the connection between the exterior and interior slider portions 196, 200 at the neck 202. As the nose 201 of the interior slider portion 200 slides upward along the chamfered wall 478 of the latch body 452, the nose 201 forces the latch 121 to move laterally in the direction of the spring legs 454. The tip-receiving aperture 474 of the latch body 452 is thus aligned over the tip cavity 222 of the valve cap 122 before the tip 104 is inserted. The inserted tip 104 can then proceed into the valve cavity 246 of the backflow valve body 124 or the valve cavity 662 of the upper valve body 526 as described above.

A user ejects a tip 104 by sliding the exterior slider portion 196 of the tip eject button 110 upward toward the handle collar 118. As the nose 201 of the interior slider portion 200 slides upward along the chamfered wall 478 of the latch body 452, the nose 201 forces the latch 121 to move laterally in the direction of the spring legs 454. In other words, the latch 121 moves substantially normal or perpendicular to the movement of the tip eject button 110. The interior lip 470 disengages from the annular recess in the tip 104 and the tip 104 is decoupled. The spring force of the spring 216 on the handle collar 118 helps to eject the tip 104 by forcing the handle collar 118 upward against the flange of the tip 104.

As noted, when the tip 104 is decoupled, the force opposing the upward force exerted by the spring 216 is removed, thereby allowing the spring 216 to move the handle collar 118 back to its original position. This movement of the handle collar 118 from a position adjacent to the bodies 192a, 192b to its original position provides a visual indication that the tip 104 has been decoupled from the latch 121.

Operation of the Handle

A user may use the handle 100 of FIGS. 1-17, the handle 500 of FIGS. 18-27, or the handle 1000 of FIGS. 28-36 and the oral irrigator to which it is fluidically connected for oral irrigation and/or cleaning of the teeth, gums, and tongue according to the following procedure.

Once a tip 104 is connected to the handle 100 as described above, and the handle 100 is fluidically connected to a fluid source, such as a reservoir of an oral irrigator, and power is supplied to the oral irrigator, the handle 100 is ready to use. Fluid flows through the hose 108 into the flow cavity 430 in the valve base 138 and into the cavity 298 of the shuttle retainer 130.

When the shuttle valve 134 is in the open position (see FIG. 5B), fluid flows from the cavity 298 of the shuttle retainer 130 (or the skirt cavity 1312 of the lower valve body 1028 in embodiments having a retaining clip 1130) into the flow lumen 342 of the shuttle valve 134. Fluid passes through the flow aperture 276 in the upper valve body 126 and, if present, into the lower portion 249 of the valve cavity 246 of the backflow valve body 124. Fluid can then enter the tip 104, which is positioned in the valve cavity 246 of the backflow valve body 124 or in the valve cavity 662, 1162 of the upper valve body 526, 1026, and exit the tip outlet 105 into the user's mouth.

Irrigate Mode and Pause Mode

During irrigate mode, fluid flows to the tip 104 as described above when the pause valve assembly 142 is placed in an open position as follows (see FIG. 5B). When the pause actuator 112 is positioned toward the handle collar 118 (i.e., in the up or on position), the shuttle valve 134, which is operably connected to the pause actuator 112 via the retaining ring 132, is moved into the shuttle compartment 284 of the upper valve body 126. The top surface 344 of the body 332 of the shuttle valve 134 approaches or contacts the bottom surface 282 of the floor 272 of the head 256 of upper valve body 126.

A flow gap 350 is simultaneously created between the bottom surface 346 of the base 334 of the shuttle valve 134 and the first surface 320 of the poppet support plate 316 of the poppet assembly 136. In this position of the shuttle valve 134, the cap 312, poppet neck 318, and sealing member 120e of the poppet assembly 136 are positioned below, not seated inside, the base cavity 348 of the shuttle valve 134. Fluid can flow from the hose 108 through the flow cavity 430 in the valve base 138, through the flow path 326 between the sprockets 324 of the poppet support plate 316, into the cavity 298 of the shuttle retainer 130, into the base cavity 348 of the shuttle valve 134, and into the flow lumen 342 of the shuttle valve 134.

During pause mode, no fluid flows into or out of the tip 104. To initiate pause mode without turning off power to the oral irrigator to which the handle 100 is connected, the pause valve assembly 142 must be moved to a closed position as follows (see FIGS. 4 and 5A). A user manually slides the pause actuator 112 downward relative to the housing 102, such as by grasping the grip portion 366 and moving it away from the handle collar 118 (i.e., in the down or off position) and substantially along a longitudinal axis of the housing 102. This translational movement of the pause actuator 112 also slides the coupled retaining ring 132 downward, which in turn slides the operably connected shuttle valve 134 downward. The flow gap 350 between the base 334 of the shuttle valve 134 and the poppet support plate 316, created during irrigate mode, is closed. The base 334 of the shuttle valve 134 contacts and seals against the first surface 320 of the poppet support plate 316 such that the cap 312, poppet neck 318, and sealing member 120e are received inside the base cavity 348 of the shuttle valve 134. The sealing member 120e helps provide a seal with the base cavity 348 and fluid is partially or completely prevented from entering the base cavity 348. Fluid can flow from the hose 108 through the valve base 138 through the flow path 326 of the poppet support plate 316 and into the cavity 298 of the shuttle retainer 130. But fluid cannot pass into the flow lumen 342 of the shuttle valve 134. Fluid flow is thereby paused or stopped through the shuttle valve 134 to the tip 104.

The pause mode is implemented by mechanical, not electrical, operation of the pause actuator 112. A mechanically actuated pause mode avoids the need for electrical circuitry in the handle 100, which thereby helps improve the safety of the handle 100 and the oral irrigator to which the handle is fluidically connected because electrical circuits are not in close physical proximity to fluid conduits. A mechanically-controlled instead of an electrically-controlled pause mode also decreases the manufacturing cost of the handle 100 and the oral irrigator. No separate battery is required in the handle 100 to power such circuits. Alternatively, the handle 100 need not be electrically wired to the oral irrigator. Thus, an easily accessible and selectable pause mode is provided to the user with significantly less manufacturing cost and greater safety.

Hose Swivel

During use, as the user moves the handle 100 into different angles and positions to access different areas of the mouth, the hose 108 can rotate freely relative to the handle 100 to remain free from tangles, bends, or kinks while maintaining a desired handle 100 orientation. In particular, as the user moves the handle 100 to different orientations, the hose 108 can rotate at its connection to the handle 100 as components of the handle 100 rotate within and relative to the housing 102. For example, the valve base 138 may be ultrasonically welded to the skirt 408 of the lower valve body 128 such that rotation of the hose 108 attached to the barbed tip 428 of the valve base 138 rotates the valve base 138, poppet assembly 136, shuttle valve 134, retaining ring 132, and lower valve body 128 within and relative to the housing 102. In some embodiments, the materials of some or all of the bushing 140, valve base 138, shuttle valve 134, retaining ring 132, and lower valve body 128 are selected to be low-friction so as to introduce minimal to no drag.

All directional references (e.g., upper, lower, upward, downward, left, right, leftward, rightward, top, bottom, above, below, vertical, horizontal, clockwise, and counterclockwise) are only used for identification purposes to aid the reader's understanding of the embodiments of the present invention, and do not create limitations, particularly as to the position, orientation, or use of the invention unless specifically set forth in the claims. Joinder references (e.g., attached, coupled, connected, joined, and the like) are to be construed broadly and may include intermediate members between a connection of elements and relative movement between elements. As such, joinder references do not necessarily infer that two elements are directly connected and in fixed relation to each other.

The above specification, examples and data provide a complete description of the structure and use of exemplary embodiments of the invention as defined in the claims. Although various embodiments of the claimed invention have been described above with a certain degree of particularity, or with reference to one or more individual embodiments, those skilled in the art could make numerous alterations to the disclosed embodiments without departing from the spirit or scope of the claimed invention. Other embodiments are therefore contemplated. It is intended that all matter contained in the above description and shown in the accompanying drawings shall be interpreted as illustrative only of particular embodiments and not limiting. Changes in detail or structure may be made without departing from the basic elements of the invention as defined in the following claims.

What is claimed is:

1. An oral irrigator handle comprising
a housing;
a fluid inlet into the housing;
a fluid outlet from the housing;
a movable shuttle valve positioned between the fluid inlet and the fluid outlet, the shuttle valve comprising a valve body defining a flow lumen therethrough in fluid communication with the fluid outlet; and
a sealing member positioned between the fluid inlet and the shuttle valve; and
a pause actuator operably connected to the shuttle valve, wherein mechanical actuation of the pause actuator moves the shuttle valve from an open position where the valve body is separated from the sealing member and the fluid inlet is fluidly connected to the flow lumen to a closed position where the valve body is positioned over the sealing member such that the sealing member seals against an inner surface of the valve body and the fluid inlet is fluidly disconnected from the flow lumen to interrupt fluid flow through the handle.

2. The oral irrigator handle of claim 1, wherein the pause actuator is movable along a longitudinal axis of the handle.

3. The oral irrigator handle of claim 1, wherein the shuttle valve is connected to the pause actuator by a retaining ring.

4. The oral irrigator handle of claim 1, further comprising an upper valve body configured to receive a distal end of the valve body of the shuttle valve in a cavity defined within the upper valve body.

5. The oral irrigator handle of claim 4, wherein the distal end of the shuttle valve occupies the cavity in the open position but not in the closed position.

6. The oral irrigator handle of claim 1, further comprising a swivel assembly connected to the valve body, wherein
the fluid inlet into the housing comprises a hose connected to the swivel assembly; and
the swivel assembly minimizes translation of rotational movement of the handle and the hose relative to each other.

7. The oral irrigator handle of claim 6, wherein
the swivel assembly comprises a valve base and a hose connector fluidly connected with the hose; and
the swivel assembly is rotatable relative to the handle housing.

8. The oral irrigator handle of claim 7, wherein the swivel assembly is configured to rotate 360 degrees relative to the handle housing.

9. The oral irrigator handle of claim 7 further comprising a bushing interposed between the valve base and the handle housing, wherein the swivel assembly rotates with respect to the bushing.

10. The oral irrigator handle of claim 7, wherein the valve base, the seal, the shuttle valve, and the valve body all rotate with the swivel assembly and relative to the handle housing.

11. An oral irrigator handle comprising
a housing;
a fluid inlet into the housing;
a fluid outlet from the housing;
a swivel assembly received within the housing and rotatable with respect thereto and fluidly coupled to the fluid inlet comprising
a valve base; and
a hose connector extending from the valve base;
a movable valve body positioned between the swivel assembly and the fluid outlet and defining a fluid lumen therethrough in fluid communication with the fluid outlet and movable between a paused position and a flow position; and
a sealing member positioned between the movable valve body and the swivel assembly, wherein:
in the paused position, the movable valve body is positioned over and encloses the sealing member such that the sealing member prevents fluid communication between the swivel assembly and the fluid lumen of the movable valve body; and
in the flow position, the movable valve body is separated from the sealing member such that the sealing member does not prevent fluid communication between the swivel assembly and the fluid lumen of the movable valve body.

12. The oral irrigator handle of claim 11, wherein the swivel assembly is configured to rotate 360 degrees relative to the handle housing.

13. The oral irrigator handle of claim 11, wherein the fluid inlet into the housing comprises a hose and the hose connector is mechanically and fluidly connected to the hose.

14. The oral irrigator handle of claim 11, further comprising
a pause actuator operably coupled to the movable valve body, wherein
mechanical actuation of the pause actuator moves the movable valve body from the flow position to the paused position to interrupt fluid flow through the handle.

15. An oral irrigator handle comprising
a housing having a longitudinal axis;
a fluid inlet into the housing;
a fluid outlet from the housing;
a valve seal;
a shuttle valve positioned between the fluid inlet and the fluid outlet and having a proximal end configured to receive a portion of the valve seal, the shuttle valve defining a flow lumen therethrough in fluid communication with the fluid outlet;
a lower valve body configured to receive the proximal end of the shuttle valve and the valve seal;
a pause actuator operably connected to the shuttle valve by a retaining ring; and
a swivel assembly comprising a valve base secured to the valve body, wherein
the swivel assembly permits rotation of the valve base, the retaining ring, the valve seal, the shuttle valve, and the valve body relative to the handle housing and around the longitudinal axis of the handle;

mechanical actuation of the pause actuator moves the shuttle valve and retaining ring along the longitudinal axis to move the shuttle valve between an open position where the shuttle valve is separated from the valve seal and the fluid inlet is fluidly connected to the flow lumen and a closed position where the shuttle valve is positioned over and partially encloses the valve seal and the fluid inlet is fluidly disconnected from the flow lumen to interrupt fluid flow through the handle.

16. The oral irrigator handle of claim 15, wherein the swivel assembly and pause actuator are operable simultaneously.

* * * * *